(12) United States Patent
Turano

(10) Patent No.: US 11,078,547 B2
(45) Date of Patent: Aug. 3, 2021

(54) ALGAL AND FUNGAL GENES AND THEIR USES FOR TAURINE BIOSYNTHESIS IN CELLS

(71) Applicant: PLANT SENSORY SYSTEMS, LLC, Baltimore, MD (US)

(72) Inventor: Frank J. Turano, Baltimore, MD (US)

(73) Assignee: PLANT SENSORY SYSTEMS, LLC, Baltimore, MD (US)

( * ) Notice: Subject to any disclaimer, the term of this patent is extended or adjusted under 35 U.S.C. 154(b) by 127 days.

(21) Appl. No.: 16/091,753

(22) PCT Filed: Apr. 7, 2016

(86) PCT No.: PCT/US2016/026465
§ 371 (c)(1),
(2) Date: Oct. 5, 2018

(87) PCT Pub. No.: WO2017/176277
PCT Pub. Date: Oct. 12, 2017

(65) Prior Publication Data
US 2019/0153463 A1    May 23, 2019

(51) Int. Cl.
*C12N 9/10* (2006.01)
*C12N 9/02* (2006.01)
*C12N 15/74* (2006.01)
*C12N 15/82* (2006.01)
*A23K 50/80* (2016.01)
*C12N 15/52* (2006.01)

(52) U.S. Cl.
CPC ......... *C12Y 113/1102* (2013.01); *A23K 50/80* (2016.05); *C12N 9/0069* (2013.01); *C12N 9/1085* (2013.01); *C12N 15/52* (2013.01); *C12N 15/74* (2013.01); *C12N 15/8257* (2013.01); *A23V 2250/0644* (2013.01); *C12Y 205/01047* (2013.01)

(58) Field of Classification Search
None
See application file for complete search history.

(56) References Cited

U.S. PATENT DOCUMENTS

2012/0222148 A1* 8/2012 Turano .............. C12N 15/8253
800/260
2013/0333068 A1  12/2013 Coffin
2014/0068812 A1* 3/2014 Turano .............. C12N 15/8223
800/278

FOREIGN PATENT DOCUMENTS

WO   2016028508 A1   2/2016

OTHER PUBLICATIONS

Tevatia et al. The taurine biosynthetic pathway of microalgae. (2015) Algal Research; vol. 9; pp. 21-26 (Year: 2015).*
Cystein dioxygenase. UniProtKB Accession A8IE68 (2007); pp. 1-7 (Year: 2007).*
Cysteine synthetase/pyridoxal dependent. UniProtKB C1MMR1 (2009); pp. 1-7 (Year: 2009).*
International Search Report and Written Opinion dated Jul. 26, 2016 issued in International Application No. PCT/US2016/026465. (6 pages).
Honjoh et al., "Enhancement of menadione stress tolerance in yeast by accumulation of hypotaurine and taurine: co-expression of cDNA clones, from Cyprinus carpio, for cysteine dioxygenase and cysteine sulfinate decarboxylase in *Saccharomyces cerevisiae*", Amino Acids, Jul. 26, 2009, 38 (4), pp. 1173-1183.
Yew et al., "The genome of newly classified Ochroconis mirabilis: Insights into fungal adaptation to different living conditions", BMC Genomics, Feb. 3, 2016, vol. 17, pp. 1-17.
Youssefian et al., "Increased Cysteine Biosynthesis Capacity of Transgenic Tobacco Overexpressing an O-Acetylserine(thiol) Lyase Modifies Plant Responses to Oxidative Stress", Plant Physiologhy, Jul. 1, 2001, 126(3), pp. 1001-1011.

* cited by examiner

*Primary Examiner* — Cathy Kingdon Worley
(74) *Attorney, Agent, or Firm* — Rothwell, Figg, Ernst & Manbeck, P.C.

(57) ABSTRACT

The present invention describes an approach to produce taurine or increase hypotaurine or taurine production in prokaryotes or eukaryotes. More particularly, the invention relates to genetic transformation of organisms with algal, microalgal or fungal genes that encode proteins that pool catalyze the conversion of sulfur-containing compounds such as sulfate or cysteine to taurine. The invention describes methods for the use of polynucleotides for cysteine dioxygenase-like (CDOL), sulfinoalanine decarboxylase-like (SADL), cysteine sulfate/decarboxylase or a portion of the cysteine synthetase/PLP decarboxylase (partCS/PLP-DC) polypeptide in bacteria, alga, yeast, or plants to produce taurine or increase hypotaurine or taurine. The preferred embodiment of the invention is in plants but other organisms may be used. Taurine production or increased levels of hypoataurine or taurine in plants could be used as nutraceutical, pharmaceutical, or therapeutic compounds or as a supplement in animal feed or for animal feed or as an enhancer for plant growth or yield.

20 Claims, 2 Drawing Sheets
Specification includes a Sequence Listing.

ALGAL AND FUNGAL GENES AND THEIR USES FOR TAURINE BIOSYNTHESIS IN CELLS

CROSS-REFERENCE TO RELATED APPLICATION

This application is a 35 U.S.C. § 371 National Stage of International Patent Application No. PCT/US2016/026465, filed 7 Apr. 2016, designating the United States, which is incorporated herein by reference in its entirety.

SEQUENCE SUBMISSION

The present application is being filed along with a Sequence Listing in electronic format. The Sequence Listing is 3834117PCT SequenceListing.txt, created on 5 Apr. 2016 and is 69 kb in size. The information in the electronic format of the Sequence Listing is incorporated herein by reference in their entirety

FIELD OF THE INVENTION

The present invention is in the field of recombinant production of taurine. The present invention includes the production of taurine in bacteria, microbes, yeast, fungi, plants and animals to increase taurine levels. The invention also relates to methods to increase taurine levels in the cells and to use the said cells or extracts, the plant or plant organs that contain the invention, or the bacteria or yeast that contain the invention to produce plant growth enhancers, food, animal feed, aquafeed, food or drink supplements, animal-feed supplements, dietary supplements, or health supplements.

BACKGROUND OF THE INVENTION

Taurine is an Essential Compound for Animals

Taurine is essential for human neonatal development (2) and plays an important role in brain development (3, 4). Taurine is involved in the modulation of intracellular calcium homeostasis (5, 6) and may balance glutamate activity, protecting neurons against glutamate excitotoxicity (7, 8). Taurine is also an osmoregulator (9). Taurine is essential for heart function (10), protects the integrity of hepatic tissue (11), and plays a role in photoprotection (12).

Taurine as a Dietary Supplement

Taurine is biosynthesized in most animals and can be found in meat and seafood. Those who do not produce sufficient levels of taurine must acquire it through dietary supplement. Dietary taurine is required for the normal development and growth of cats, (13, 14) human infants, (15) and carnivorous fish. (16-24) Taurine also improves the health and/or growth of other fish species(25-28) and shrimp. (29) Taurine is a feed attractant for fish.(21, 30)

Taurine as a Pharmaceutical or Therapeutic

Taurine is used as a pharmaceutical and therapeutic. Taurine has been used in the treatment of cardiovascular diseases (31, 32), elevated blood pressure (33), seizure disorders (34), hepatic disorders (35), and alcoholism (36) and may be useful in the treatment of diabetes (37), Alzheimer's disease (38), and ocular disorders (39). Taurine has been shown to prevent obesity (40) and control cholesterol (41, 42). Taurine acts as an antioxidant and protects against toxicity of various substances (43-45). Taurine has been shown to prevent oxidative stress induced by exercise (46), and is used in energy drinks to improve performance (47). Taurine can also be used in topical applications to treat dermatological conditions (48).

Taurine as a Plant Growth Stimulator

Exogenous application of taurine has been reported to increase crop harvest, yield, and biomass (49). Applications of taurine by foliar spray, soil and roots application, and seed immersion increase crop production and seedling growth (49). Exogenous applications of taurine have also been shown to increase photosynthetic capacity of isolated plant cells (protoplasts and chloroplasts) (49).

Metabolic Pathways that Synthesize Taurine

Several metabolic pathways that synthesize taurine and hypotaurine have been identified in animals and bacteria (FIG. 1). These genes and their corresponding gene products have been described in the literature (50-52). A recent study has shown that several algal and microalgal species can synthesize taurine (53). The authors suggest that these organisms may contain the genes for taurine synthesis. However, they never disclose the sequences of the genes or the sequences of the corresponding peptides. Nor do they provide validation through genetic (knock-out or complementation) or biochemical means of the function of the genes or their corresponding peptides.

This invention describes the use of algal, microalgal, fungal (yeast), diatom and unicellular organism genes and their corresponding peptides for taurine synthesis in cells. The genes include cysteine dioxygenase-like (CDOL), sulfinoalanine decarboxylase-like (SADL), cysteine synthetase/PLP decarboxylase (CS/PLP-DC) or a portion of the cysteine synthetase/PLP decarboxylase (partCS/PLP-DC). The invention also describes how to use the cells, fractions of the cells, or extracts from the cells for a variety of purposes, including as an additive, feed ingredient, extract or meal. This invention describes the use of polynucleotides and their corresponding polypeptides not derived from vertebrates, invertebrates or bacteria. This invention does not include genes or peptides from animals or bacterial, which are described in the prior art (50-52) and include cysteine dioxygenase (CDO), sulfinoalanine decarboxylase (SAD), glutamate decarboxylase (GAD), hypotaurine dehydrogenase (HTDeHase), cysteamine dioxygenase (ADO), cysteine lyase (cysteine sulfite lyase or cysteine hydrogen-sulfide-lyase), sulfoacetaldehyde acetyltransferase (SA), taurine-pyruvate aminotransferase (TPAT) and taurine dioxygenase (TDO).

SUMMARY OF THE INVENTION

The invention provides methods and compositions for taurine production in organisms. More particularly, the invention encompasses the use of polynucleotides from algal sources that can be used in bacteria, fungi (yeast) or plants. The invention provides methods for transforming plants and constructing vector constructs and other nucleic acid molecules for use therein. The invention also provides methods for transforming bacteria, yeast, fungi, and unicellular algae and constructing vector constructs and other nucleic acid molecules for use therein. The transgenic plants, bacteria, yeast, fungi, or unicellular algae will have increased levels of taurine for use as animal feed, food, or as a supplement in animal feed or food or to enhance plant growth or yield.

The invention provides isolated cells comprising exogenous DNA which expresses enzymes of taurine biosynthetic pathways. In one embodiment, an isolated cell comprises two separate expression cassettes. A first expression cassette comprises a first promoter operably linked to a first polynucleotide, and a second expression cassette comprises a second promoter operably linked to a second polynucleotide. In some embodiments, the first polynucleotide encodes cysteine dioxygenase-like (CDOL) and the second polynucleotide encodes sulfinoalanine decarboxylase-like (SADL). In other embodiments the first polynucleotide encodes CDOL and the second polynucleotide encodes cysteine synthetase/PLP decarboxylase (CS/PLP-DC) or a portion of the cysteine synthetase/PLP decarboxylase (partCS/PLP-DC).

Some isolated cells of the invention comprise exogenous DNA which comprises a single expression cassette. The single expression cassette comprises a promoter operably linked to a polynucleotide which encodes (i) CS/PLP-DC; (ii) SADL; (iii) partCS/PLP-DC; (iv) CDOL operably linked to SADL; (v) CDOL operably linked to CS/PLP-DC; or (vi) CDOL operably linked to partCS/PLP-DC.

The invention also provides plant storage organs comprising isolated cells of the invention; transgenic seeds with a genome comprising exogenous DNA-encoding one or more of (i) CS/PLP-DC; (ii) SADL; (iii) partCS/PLP-DC; (iv) CDOL and SADL; (v) CDOL and CS/PLP-DC; or (vi) CDOL and partCS/PLP-DC, and transgenic plants grown from the transgenic seeds.

The invention provides methods of altering a property of a transgenic plant of the invention by contacting the transgenic plant with an agent which increases sulfur or nitrogen concentration in cells of the transgenic plant.

The invention also provides nutritional supplements, feed supplements, and pharmaceutical compositions comprising an extract or meal from a transgenic plant of the invention, or comprising a component, which can be one or more of the plant storage organs, transgenic seeds, and transgenic plants of the invention.

In one embodiment of the invention polynucleotides encoding functional (i) CS/PLP-DC; (ii) SADL; (iii) partCS/PLP-DC; (iv) CDOL and SADL; (v) CDOL and CS/PLP-DC; or (vi) CDOL and partCS/PLP-DC enzymes are used to transform yeast, fungal, bacterial or algal cells. Inventive methods produce cells that have taurine production for nutritional, pharmaceutical, or therapeutic value, feed, food or drink. Cells are genetically modified in accordance with the invention to include polynucleotides that encode a CDOL, SADL, partCS/PLP-DC, or CS/PLP-DC enzyme that functions in the formation of hypotaurine or taurine in the cell.

Another embodiment of the invention describes the use of polynucleotides that encode polypeptides for functional (i) CS/PLP-DC; (ii) SADL; (iii) partCS/PLP-DC; (iv) CDOL and SADL; (v) CDOL and CS/PLP-DC; or (vi) CDOL and partCS/PLP-DC expressed in eukaryotes or prokaryotes or in eukaryotic or prokaryotic cells, for hypotaurine or taurine production.

The inventive methods produce plants that have the advantage of increased levels of sulfur-containing compounds, specifically taurine, resulting in algae or plants with increased nutritional value or algae or plant material with improved characteristics for food or feed production, including hypotaurine or taurine production, higher levels of taurine, lower taurine leaching rates, and increased bioavailability of taurine.

DETAILED DESCRIPTION OF THE INVENTION

Figure 1:
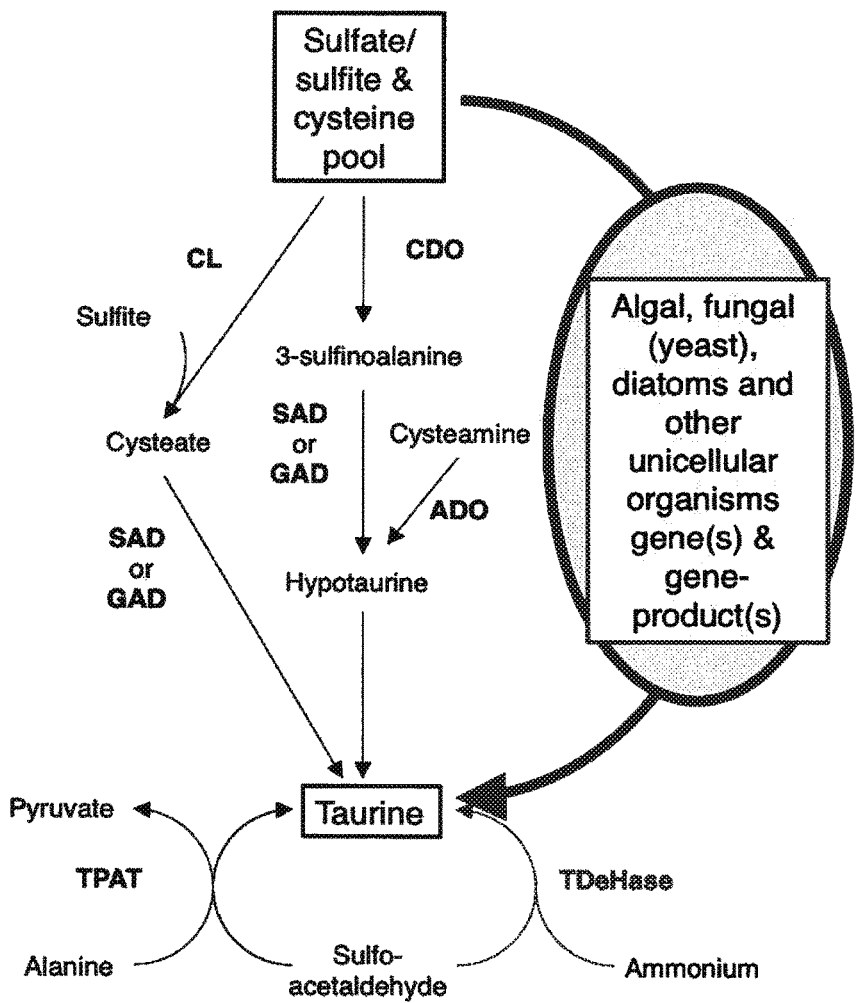
FIG. 1 shows the novel algal, fungi (yeast), diatom and other unicellular organism genes and their corresponding proteins (CDOL, SADL, partCS/PLP-DC, or CS/PLP-DC) in relation to the known animal and bacterial taurine biosynthetic pathways. In animals, cysteine and oxygen are converted into 3-sulfinoalanine by cysteine dioxygenase (CDO). 3-sulfinoalanine is converted into hypotaurine by sulfinoalanine decarboxylase (SAD) or glutamate decarboxylase (GAD). Hypotaurine is converted into taurine either by the activity of hypotaurine dehydrogenase (HTDeHase) or by a spontaneous conversion. Cysteamine (2-aminoethanethiol) and oxygen are converted into hypotaurine by cysteamine dioxygenase (ADO), and hypotaurine is converted into taurine. Alternatively cysteine and sulfite are converted into cysteate and hydrogen sulfide by cysteine lyase (cysteine sulfite lyase or cysteine hydrogen-sulfide-lyase). Cysteate is converted into taurine by SAD or GAD. In bacteria, the compound 2-sulfoacetaldehyde is synthesized from acetyl phosphate and sulfite by sulfoacetaldehyde acetyltransferase (SA). Alanine and 2-sulfoacetaldehyde are converted into taurine and pyruvate by taurine-pyruvate aminotransferase (TPAT). In addition, sulfoacetaldehyde and ammonia (or ammonium) are converted into taurine and water in the presence of ferrocytochrome C by taurine dehydrogenase. Sulfite, aminoacetaldehyde, carbon dioxide and succinate are converted into taurine, 2-oxoglutarate and oxygen by taurine dioxygenase (TDO).

The present invention provides methods and materials for the production of taurine (2-aminoethanesulfonic acid) in cells and living organisms. In preferred embodiments, the invention provides methods for the genetic transformation of organisms, preferably plants, with genes that encode proteins that catalyze the conversion of sulfur-compounds such as sulfate or cysteine to taurine. The invention also provides methods of using plants, bacteria, fungi or yeast bacteria, yeast, fungi, or unicellular algae with increased levels of endogenous taurine or taurine derivatives such as hypotaurine as a food- or feed-supplement, dietary supplement, as a component of a health supplement or therapy or for plant growth or yield.

The present invention describes the methods for the synthesis of DNA constructs for taurine production from polynucleotides and vectors and the methods for making transformed organisms including plants, photosynthetic organisms, microbes, invertebrates, and vertebrates. The present invention is unique in that it describes a method to produce plants that have advantages of enhanced taurine production or hypotaurine and that result in plants with increased nutritional, pharmaceutical, or therapeutic value or with enhanced plant growth characteristics.

The present invention describes the insertion of the taurine biosynthetic pathway in organisms where the pathway does not exist or has not clearly been identified. The invention describes methods for the use of polynucleotides that encode functional CDOL, SADL, partCS/PLP-DC, or CS/PLP-DC in plants. The preferred embodiment of the invention is in plants but other organisms may be used.

Enzymes of Taurine Biosynthetic Pathways

Examples of amino acid sequences of enzymes of algal and fungal taurine biosynthetic pathways are provided in the sequence listing: SEQ ID NO:5, SEQ ID NO:6, SEQ ID NO:7, and SEQ ID NO:8 (CDOL); SEQ ID NO:15 and SEQ ID NO:16 (CS/PLP-DC); SEQ ID NO:17, SEQ ID NO:18, SEQ ID NO:19 and SEQ ID NO:20 (SADL). The invention is not limited to the use of these amino acid sequences. Those of ordinary skill in the art know that organisms of a wide variety of species commonly express and utilize homologous proteins, which include the insertions, substitutions and/or deletions discussed above, and effectively provide similar function. For example, the amino acid sequences for CDOL from *Chlamydomonas reinhardtii* or *Fragilariopsis cylindrus*, SADL from Guillardia *theta* or *Cyanidioschyzon merolae*, or CS/PLP-DC from *Micromonas pusilla* or Ostreococcus *tauri* may differ to a certain degree from the amino acid sequences of CDOL, SADL or CS/PLP-DC in another species and yet have similar functionality with respect to catalytic and regulatory function. Amino acid sequences comprising such variations are included within the scope of the present invention and are considered substantially or sufficiently similar to a reference amino acid sequence. Although it is not intended that the present invention be limited by any theory by which it achieves its advantageous result, it is believed that the identity between amino acid sequences that is necessary to maintain proper functionality is related to maintenance of the tertiary structure of the polypeptide such that specific interactive sequences will be properly located and will have the desired activity, and it is contemplated that a polypeptide including these interactive sequences in proper spatial context will have activity.

Another manner in which similarity may exist between two amino acid sequences is where there is conserved substitution between a given amino acid of one group, such as a non-polar amino acid, an uncharged polar amino acid, a charged polar acidic amino acid, or a charged polar basic amino acid, with an amino acid from the same amino acid group. For example, it is known that the uncharged polar amino acid serine may commonly be substituted with the uncharged polar amino acid threonine in a polypeptide without substantially altering the functionality of the polypeptide. Whether a given substitution will affect the functionality of the enzyme may be determined without undue experimentation using synthetic techniques and screening assays known to one with ordinary skill in the art.

One of ordinary skill in the art will recognize that changes in the amino acid sequences, such as individual substitutions, deletions or additions to a nucleic acid, peptide, polypeptide, or protein sequence which alters, adds or deletes a single amino acid or a small percentage of amino acids in the encoded sequence is "sufficiently similar" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, CDOL, SADL or CS/PLP-DC activity is generally at least 40%, 50%, 60%, 70%, 80% or 90%, preferably 60-90% of the native protein for the native substrate. Tables of conserved substitution provide lists of functionally similar amino acids.

The following three groups each contain amino acids that are conserved substitutions for one another: (1) Alanine (A), Serine (S), Threonine (T); (2) Aspartic acid (D), Glutamic acid (E); and (3) Asparagine (N), Glutamine (Q);

Suitable Polynucleotides Far CDOL, SADL, and CS/PLP-DC

As examples, suitable polynucleotides encoding enzymes of taurine biosynthetic pathways are described below. The invention is not limited to use of these sequences, however. In fact, any nucleotide sequence which encodes an enzyme of a taurine biosynthetic pathway can be used in an expression vector to produce that enzyme recombinantly.

Suitable polynucleotides for CDOL are provided in SEQ ID NO:1, SEQ ID NO:2, SEQ ID NO:3 and SEQ ID NO:4. Other suitable polynucleotides for use in accordance with the invention may be obtained by the identification of polynucleotides that selectively hybridize to the polynucleotides of SEQ ID NO:1, SEQ ID NO:2, SEQ ID NO:3 or SEQ ID NO:4, by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:1, SEQ ID NO:2, SEQ ID NO:3 or SEQ ID NO:4 when it used as a reference for sequence comparison or polynucleotides that encode polypeptides that have substantial identity to amino acid sequence of SEQ ID NO:5, SEQ ID NO:6, SEQ ID NO:7 or SEQ ID NO:8 when it used as a reference for sequence comparison.

Suitable polynucleotides for SADL are provided in SEQ ID NO:11, SEQ ID NO:12, SEQ ID NO:13 and SEQ ID NO:14. Other suitable polynucleotides for use in accordance with the invention may be obtained by the identification of polynucleotides that selectively hybridize to the polynucleotides of SEQ ID NO:11, SEQ ID NO:12, SEQ ID NO:13 or SEQ ID NO:14 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:11, SEQ ID NO:12, SEQ ID NO:13 or SEQ ID NO:14 when it used as a reference for sequence comparison or polynucleotides that encode polypeptides that have substantial identity to amino acid sequence of SEQ ID NO:17, SEQ ID NO:18, SEQ ID NO:19 or SEQ ID NO:20 when it is used as a reference for sequence comparison.

Suitable polynucleotides for CS/PLP-DC are provided in SEQ ID NO:9 and SEQ ID NO:10. Other suitable polynucleotides for use in accordance with the invention may be obtained by the identification of polynucleotides that selectively hybridize to the polynucleotides of SEQ ID NO:9 or SEQ ID NO:10 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:9 or SEQ ID NO:10 when it used as a reference for sequence comparison or polynucleotides that encode polypeptides that have substantial identity to amino acid sequence of SEQ ID NO:15 or SEQ ID NO:16 when it used as a reference for sequence comparison.

Another embodiment of the invention is a polynucleotide (e.g., a DNA construct) that encodes a protein that functions as a CDOL, SADL, or CS/PLP-DC and selectively hybridizes to either SEQ ID NO:1, SEQ ID NO:2, SEQ ID NO:3, SEQ ID NO:4, SEQ ID NO:9, SEQ ID NO:10, SEQ ID NO:11, SEQ ID NO:12, SEQ ID NO:13, or SEQ ID NO:14 respectively. Selectively hybridizing sequences typically have at least 40% sequence identity, preferably 60-90% sequence identity, and most preferably 100% sequence identity with each other.

Another embodiment of the invention is a polynucleotide that encodes a polypeptide that has substantial identity to the amino acid sequence of SEQ ID NO:5, SEQ ID NO:6, SEQ ID NO:15, SEQ ID NO:16, SEQ ID NO:17, SEQ ID NO:18, SEQ ID NO:19, or SEQ ID NO:20. Substantial identity of amino acid sequences for these purposes normally means sequence identity of between 50-100%, preferably at least 55%, preferably at least 60%, more preferably at least 70%, 80%, 90%, and most preferably at least 95%.

The process of encoding a specific amino acid sequence may involve DNA sequences having one or more base changes (i.e., insertions, deletions, substitutions) that do not cause a change in the encoded amino acid, or which involve base changes which may alter one or more amino acids, but do not eliminate the functional properties of the polypeptide encoded by the DNA sequence.

It is therefore understood that the invention encompasses more than the specific polynucleotides encoding the proteins described herein. For example, modifications to a sequence, such as deletions, insertions, or substitutions in the sequence, which produce "silent" changes that do not substantially affect the functional properties of the resulting polypeptide are expressly contemplated by the present invention. Furthermore, because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill in the art will recognize that each amino acid has more than one codon, except for methionine and tryptophan that ordinarily have the codons AUG and UGG, respectively. It is known by those of ordinary skill in the art, "universal" code is not completely universal. Some mitochondrial and bacterial genomes diverge from the universal code, e.g., some termination codons in the universal code specify amino acids in the mitochondria or bacterial codes. Thus each silent variation of a nucleic acid, which encodes a polypeptide of the present invention, is implicit in each described polypeptide sequence and incorporated in the descriptions of the invention.

It is understood that alterations in a nucleotide sequence, which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product.

Nucleotide changes which result in alteration of the amino-terminal and carboxy-terminal portions of the encoded polypeptide molecule would also not generally be expected to alter the activity of the polypeptide. In some cases, it may in fact be desirable to make mutations in the sequence in order to study the effect of alteration on the biological activity of the polypeptide. Each of the proposed modifications is well within the routine skill in the art.

When the nucleic acid is prepared or altered synthetically, one of ordinary skill in the art can take into account the known codon preferences for the intended host where the nucleic acid is to be expressed. For example, although nucleic acid sequences of the present invention may be expressed in both monocotyledonous and dicotyledonous plant species, sequences can be modified to account for the specific codon preferences and GC-content preferences of monocotyledonous plants or dicotyledonous plants, as these preferences have been shown to differ (54).

Cloning Techniques

For purposes of promoting an understanding of the principles of the invention, reference will now be made to particular embodiments of the invention and specific language will be used to describe the same. The materials, methods and examples are illustrative only and not limiting. Unless mentioned otherwise, the techniques employed or contemplated herein are standard methodologies well known to one of ordinary skill in the art. Specific terms, while employed below and defined at the end of this section, are used in a descriptive sense only and not for purposes of limitation. The practice of the present invention will employ, unless otherwise indicated, conventional techniques of botany, microbiology, tissue culture, molecular biology, chemistry, biochemistry and recombinant DNA technology, which are within the skill of the art (55-62).

A suitable polynucleotide for use in accordance with the invention may be obtained by cloning techniques using cDNA or genomic libraries, DNA, or cDNA from bacteria which are available commercially or which may be constructed using standard methods known to persons of ordinary skill in the art. Suitable nucleotide sequences may be isolated from DNA libraries obtained from a wide variety of species by means of nucleic acid hybridization or amplification methods, such as polymerase chain reaction (PCR) procedures, using as probes or primers nucleotide sequences selected in accordance with the invention.

Furthermore, nucleic acid sequences may be constructed or amplified using chemical synthesis. The product of amplification is termed an amplicon. Moreover, if the particular nucleic acid sequence is of a length that makes chemical synthesis of the entire length impractical, the sequence may be broken up into smaller segments that may be synthesized and ligated together to form the entire desired sequence by methods known in the art. Alternatively, individual components or DNA fragments may be amplified by PCR and adjacent fragments can be ampled together using fusion-PCR (63), overlap-PCR (64) or chemical (de novo) synthesis (65-69) using a vendor (e.g. GE life technologies, GENEART, Gen9, GenScript) by methods known in the art.

A suitable polynucleotide for use in accordance with the invention may be constructed by recombinant DNA technology, for example, by cutting or splicing nucleic acids using restriction enzymes and mixing with a cleaved (cut with a restriction enzyme) vector with the cleaved insert (DNA of the invention) and ligated using DNA ligase. Alternatively amplification techniques, such as PCR, can be used, where restriction sites are incorporated in the primers that otherwise match the nucleotide sequences (especially at the 3' ends) selected in accordance with the invention. The desired amplified recombinant molecule is cut or spliced using restriction enzymes and mixed with a cleaved vector and ligated using DNA ligase. In another method, after amplification of the desired recombinant molecule, DNA linker sequences are ligated to the 5' and 3' ends of the desired nucleotide insert with ligase, the DNA insert is cleaved with a restriction enzyme that specifically recognizes sequences present in the linker sequences and the desired vector. The cleaved vector is mixed with the cleaved insert, and the two fragments are ligated using DNA ligase. In yet another method, the desired recombinant molecule is amplified with primers that have recombination sites (e.g. Gateway) incorporated in the primers, that otherwise match the nucleotide sequences selected in accordance with the invention. The desired amplified recombinant molecule is mixed with a vector containing the recombination site and recombinase, the two molecules are ligated together by recombination.

The recombinant expression cassette or DNA construct includes a promoter that directs transcription in a plant cell, operably linked to the polynucleotide encoding a CDOL, SADL, partCS/PLP-DC, or CS/PLP-DC. In various aspects of the invention described herein, a variety of different types of promoters are described and used. As used herein, a polynucleotide is "operably linked" to a promoter or other nucleotide sequence when it is placed into a functional relationship with the promoter or other nucleotide sequence. The functional relationship between a promoter and a desired polynucleotide insert typically involves the polynucleotide and the promoter sequences being contiguous such that transcription of the polynucleotide sequence will be facilitated. Two nucleic acid sequences are further said to be operably linked if the nature of the linkage between the two sequences does not (1) result in the introduction of a frame-shift mutation; (2) interfere with the ability of the promoter region sequence to direct the transcription of the desired nucleotide sequence, or (3) interfere with the ability of the desired nucleotide sequence to be transcribed by the promoter sequence region. Typically, the promoter element is generally upstream (i.e., at the 5' end) of the nucleic acid insert coding sequence.

While a promoter sequence can be ligated to a coding sequence prior to insertion into a vector, in other embodiments, a vector is selected that includes a promoter operable in the host cell into which the vector is to be inserted. In addition, certain preferred vectors have a region that codes a ribosome binding site positioned between the promoter and the site at which the DNA sequence is inserted so as to be operatively associated with the DNA sequence of the invention to produce the desired polypeptide, i.e., the DNA sequence of the invention in-frame.

Suitable Peptide Linkers

Peptide linkers are known to those skilled in the art to connect protein domains or peptides. In general, linkers that contain the amino acids glycine and serine are useful linkers. (70, 71) Other suitable linkers that can be used in the invention include, but are not limited to, those described by Kuusinen et. al. (72) Robinson and Sauer, (73) Armstrong & Gouaux, (74) Arai et. al., (75) Wriggers et. al., (76) and Reddy et. al (77).

Suitable Promoters

A wide variety of promoters are known to those of ordinary skill in the art as are other regulatory elements that can be used alone or in combination with promoters. A wide variety of promoters that direct transcription in plants cells can be used in connection with the present invention. For purposes of describing the present invention, promoters are divided into two types, namely, constitutive promoters and non-constitutive promoters. Constitutive promoters are classified as providing for a range of constitutive expression. Thus, some are weak constitutive promoters, and others are strong constitutive promoters. Non-constitutive promoters include tissue-preferred promoters, tissue-specific promoters, cell-type specific promoters, and inducible-promoters.

Of particular interest in certain embodiments of the present invention are inducible-promoters that respond to various forms of environmental stresses, or other stimuli, including, for example, mechanical shock, heat, cold, salt, flooding, drought, salt, anoxia, pathogens, such as bacteria, fungi, and viruses, and nutritional deprivation, including deprivation during times of flowering and/or fruiting, and other forms of plant stress. For example, the promoter selected in alternate forms of the invention, can be a promoter is induced by one or more, but not limiting to one of the following, abiotic stresses such as wounding, cold, dessication, ultraviolet-B (78), heat shock (79) or other heat stress, drought stress or water stress. The promoter may further be one induced by biotic stresses including pathogen stress, such as stress induced by a virus (80) or fungi (81, 82), stresses induced as part of the plant defense pathway (83) or by other environmental signals, such as light (84), carbon dioxide (85, 86), hormones or other signaling molecules such as auxin, hydrogen peroxide and salicylic acid (87, 88), sugars and gibberellin (89) or abscissic acid and ethylene (90).

In other embodiments of the invention, tissue-specific promoters are used. Tissue-specific expression patterns as controlled by tissue- or stage-specific promoters that include, but is not limited to, fiber-specific, green tissue-specific, root-specific, stem-specific, and flower-specific. Examples of the utilization of tissue-specific expression includes, but is not limited to, the expression in leaves of the desired peptide for the protection of plants against foliar pathogens, the expression in roots of the desired peptide for the protection of plants against root pathogens, and the expression in roots or seedlings of the desired peptide for the protection of seedlings against soil-borne pathogens. In many cases, however, protection against more than one type of pathogen may be sought, and expression in multiple tissues will be desirable.

Of particular interest in certain embodiments of the present invention seed-specific promoters are used. Examples of the utilization of seed-specific promoters for expression includes, but is not limited to, napin, (91) sunflower seed-specific promoter, (92) AtFAD2, (93) phaseolin, (94) beta-conglycinin, (95) zein, (96) and rice glutelin. (97)

Although some promoters from dicotyledons have been shown to be operational in monocotyledons and vice versa, ideally dicotyledonous promoters are selected for expression in dicotyledons, and monocotyledonous promoters are selected for expression in monocotyledons. There are also promoters that control expression of genes in green tissue or for genes involved in photosynthesis from both monocotyledons and dicotyledons such as the maize from the phosphenol carboxylase gene. (98) There are suitable promoters for root specific expression (99, 100). A promoter selected can be an endogenous promoter, i.e. a promoter native to the species and or cell type being transformed. Alternatively, the promoter can be a foreign promoter, which promotes transcription of a length of DNA of viral, microbes, bacterial or eukaryotic origin, invertebrates, vertebrates including those from plants and plant viruses. For example, in certain preferred embodiments, the promoter may be of viral origin, including a cauliflower mosaic virus promoter (CaMV), such as CaMV 35S or19S, a figwort mosaic virus promoter (FMV 35S), or the coat protein promoter of tobacco mosaic virus (TMV). The promoter may further be, for example, a promoter for the small subunit of ribulose-1, 3-biphosphate carboxylase. Promoters of bacterial origin (microbe promoters) include the octopine synthase promoter, the nopaline synthase promoter and other promoters derived from native Ti plasmids. (101)

The promoters may further be selected such that they require activation by other elements known to those of ordinary skill in the art, so that production of the protein encoded by the nucleic acid sequence insert may be regulated as desired. In one embodiment of the invention, a DNA construct comprising a non-constitutive promoter operably linked to a polynucleotide encoding the desired polypeptide of the invention is used to make a transformed plant that selectively increases the level of the desired polypeptide of the invention in response to a signal. The term "signal" is used to refer to a condition, stress or stimulus that results in or causes a non-constitutive promoter to direct expression of a coding sequence operably linked to it. To make such a plant in accordance with the invention, a DNA construct is provided that includes a non-constitutive promoter operably linked to a polynucleotide encoding the desired polypeptide of the invention. The construct is incorporated into a plant genome to provide a transformed plant that expresses the polynucleotide in response to a signal.

In alternate embodiments of the invention, the selected promoter is a tissue-preferred promoter, a tissue-specific promoter, a cell-type-specific promoter, an inducible promoter or other type of non-constitutive promoter. It is readily apparent that such a DNA construct causes a plant transformed thereby to selectively express the gene for the desired polypeptide of the invention. Therefore under specific conditions or in certain tissue- or cell-types the desired polypeptide will be expressed. The result of this expression in the plant depends upon the activity of the promoter and in some cases the conditions of the cell or cells in which it is expressed.

It is understood that the non-constitutive promoter does not continuously produce the transcript or RNA of the invention. But in this embodiment the selected promoter for inclusion of the invention advantageously induces or increases transcription of gene for the desired polypeptide of the invention in response to a signal, such as an environmental cue or other stress signal including biotic and/or abiotic stresses or other conditions.

In another embodiment of the invention, a DNA construct comprising a plant GAD promoter operably linked to polynucleotides that encode the desired polypeptide of the invention is used to make a transformed plant that selectively increases the transcript or RNA of the desired polypeptide of the invention in the same cells, tissues, and under the environmental conditions that express a plant glutamate decarboxylase. It is understood to those of ordinary skill in the art that the regulatory sequences that comprise a plant promoter driven by RNA polymerase II reside in the region approximately 2900 to 1200 basepairs up-stream (5') of the translation initiation site or start codon (ATG). For example, the full-length promoter for the nodule-enhanced PEP carboxylase from alfalfa is 1277 basepairs prior to the start codon (102), the full-length promoter for cytokinin oxidase from orchid is 2189 basepairs prior to the start codon (103), the full-length promoter for ACC oxidase from peach is 2919 basepairs prior to the start codon (104), full-length promoter for cytokinin oxidase from orchid is 2189 basepairs prior to the start codon, full-length promoter for glutathione peroxidase1 from *Citrus sinensis* is 1600 basepairs prior to the start codon (105), and the full-length promoter for glucuronosyltransferase from cotton is 1647 basepairs prior to the start codon (106). Most full-length promoters are 1700 basepairs prior to the start codon. The accepted convention is to describe this region (promoter) as −1700 to −1, where the numbers designate the number of basepairs prior to the "A" in the start codon. Other plant specific promoters include but are not limited to glutamate deacarboxylase (GAD), *Arabidopsis thaliana* glutamate receptors (AtGLRs or AtGluRs) or plant sulphate transporter promoter (51) or use amplification, such as PCR, techniques with the incorporation of restriction or recombination sites to clone the plant promoters 5' to the desired polynucleotide.

Plastid Transit Peptides

A wide variety of plastid transit peptides are known to those of ordinary skill in the art that can be used in connection with the present invention. Suitable transit peptides which can be used to target any CDOL, SADL, partCS/PLP-DC or CS/PLP-DC polypeptide to a plastid include, but are not limited, to those described herein and in U.S. Pat. No. 8,779,237 (107), U.S. Pat. No. 8,674,180 (108), U.S. Pat. No. 8,420,888 (109), and U.S. Pat. No. 8,138,393 (110) and in Lee et al. (111) and von Heijne et al. (112) Cloning a nucleic acid sequence that encodes a transit peptide upstream and in-frame of a nucleic acid sequence that encodes a polypeptide involves standard molecular techniques that are well-known in the art.

Suitable Vectors

A wide variety of vectors may be employed to transform a plant, plant cell or other cells with a construct made or selected in accordance with the invention, including high- or low-copy number plasmids, phage vectors and cosmids. Such vectors, as well as other vectors, are well known in the art. Representative T-DNA vector systems (101, 113) and numerous expression cassettes and vectors and in vitro culture methods for plant cell or tissue transformation and regeneration of plants are known and available. (114) The vectors can be chosen such that operably linked promoter and polynucleotides that encode the desired polypeptide of the invention are incorporated into the genome of the plant. Although the preferred embodiment of the invention is expression in plants or plant cells, other embodiments may include expression in prokaryotic or eukaryotic photosynthetic organisms, yeast, fungi, algae, microalgae, microbes, invertebrates or vertebrates.

It is known by those of ordinary skill in the art that there exist numerous expression systems available for expression of a nucleic acid encoding a protein of the present invention. There are many commercially available recombinant vectors to transform a host plant or plant cell. Standard molecular and cloning techniques (59, 62, 115) are available to make a recombinant expression cassette that expresses the polynucleotide that encodes the desired polypeptide of the invention. No attempt to describe in detail the various methods known for the expression of proteins in prokaryotes or eukaryotes will be made. In brief, the expression of isolated nucleic acids encoding a protein of the present invention will typically be achieved by operably linking, for example, the DNA or cDNA to a promoter, followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high-level expression of a cloned gene, it is desirable to construct expression vectors that contain, at the minimum, a strong promoter, such as ubiquitin, to direct transcription, a ribosome-binding site for translational initiation, and a transcription/translation terminator.

One of ordinary skill to the art recognizes that modifications could be made to a protein of the present invention without diminishing its biological activity. Some modifications may be made to facilitate the cloning, expression, targeting or to direct the location of the polypeptide in the host, or for the purification or detection of the polypeptide by the addition of a "tag" as a fusion protein. Such modifications are well known to those of skill in the art and include, for example, a methionine added at the amino terminus to provide an initiation site, additional amino acids (tags) placed on either terminus to create a tag, additional nucleic acids to insert a restriction site or a termination.

In addition to the selection of a suitable promoter, the DNA constructs requires an appropriate transcriptional terminator to be attached downstream of the desired gene of the invention for proper expression in plants. Several such terminators are available and known to persons of ordinary skill in the art. These include, but are not limited to, the tml from CaMV and E9 from rbcS. Another example of a terminator sequence is the polyadenlyation sequence from the bovine growth hormone gene. A wide variety of available terminators known to function in plants can be used in the context of this invention. Vectors may also have other control sequence features that increase their suitability. These include an origin of replication, enhancer sequences, ribosome binding sites, RNA splice sites, polyadenylation sites, selectable markers and RNA stability signal. Origin of replication is a gene sequence that controls replication of the vector in the host cell. Enhancer sequences cooperate with the promoter to increase expression of the polynucleotide insert coding sequence. Enhancers can stimulate promoter activity in host cell. An example of specific polyadenylation sequence in higher eukaryotes is ATTTA. Examples of plant polyadenylation signal sequences are AATAAA or AATAAT. RNA splice sites are sequences that ensure accurate splicing of the transcript. Selectable markers usually confer resistance to an antibiotic, herbicide or chemical or provide color change, which aid the identification of transformed organisms. The vectors also include a RNA stability signal, which are 3'-regulatory sequence elements that increase the stability of the transcribed RNA. (116, 117)

Terminators

Terminators are typically located downstream (3') of the gene, after the stop codon (TGA, TAG or TAA). Terminators play an important role in the processing and stability of RNA as well as in translation. Most, but not all terminators, contain a polyadenylation sequence or cleavage site. Examples of specific polyadenylation sequences are AAUAAA or AAUAAU. These sequences are known as the near upstream elements (NUEs). (118) NUEs usually reside approximately 30 bp away from a GU-rich region (119-121) which is known as far upstream elements (FUEs). The FUEs enhance processing at the polyadenylation sequence or cleavage site, which is usually a CA or UA in a U-rich region. (122) Within the terminator, elements exist that increase the stability of the transcribed RNA,(116, 117, 123) and may also control gene expression. (124)

In addition, polynucleotides that encode a CDOL, SADL, partCS/PLP-DC or CS/PLP-DC can be placed in the appropriate plant expression vector used to transform plant cells. The polypeptide can then be isolated from plant callus or the transformed cells can be used to regenerate transgenic plants. Such transgenic plants can be harvested, and the appropriate tissues can be subjected to large-scale protein extraction and purification techniques.

The vectors may include another polynucleotide insert that encodes a peptide or polypeptide used as a "tag" to aid in purification or detection of the desired protein. The additional polynucleotide is positioned in the vector such that upon cloning and expression of the desired polynucleotide a fusion, or chimeric, protein is obtained. The tag may be incorporated at the amino or carboxy terminus. If the vector does not contain a tag, persons with ordinary skill in the art know that the extra nucleotides necessary to encode a tag can be added with the ligation of linkers, adaptors, or spacers or by PCR using designed primers. After expression of the peptide the tag can be used for purification using affinity chromatography, and if desired, the tag can be cleaved with an appropriate enzyme. The tag can also be maintained, not cleaved, and used to detect the accumulation of the desired polypeptide in the protein extracts from the host using western blot analysis. In another embodiment, a vector includes the polynucleotide for the tag that is fused in-frame to the polynucleotide that encodes a functional CDOL, SADL, partCS/PLP-DC or CS/PLP-DC to form a fusion protein. The tags that may be used include, but are not limited to, Arg-tag, calmodulin-binding peptide, cellulose-binding domain, DsbA, c-myc-tag, glutathione S-transferase, FLAG-tag, HAT-tag, His-tag, maltose-binding protein, NusA, S-tag, SBP-tag, Strep-tag, and thioredoxin (Trx-Tag). These are available from a variety of manufacturers Clontech Laboratories, Takara Bio Company GE Healthcare, Invitrogen, Novagen Promega and QIAGEN.

The vector may include another polynucleotide that encodes a signal polypeptide or signal sequence ("subcellular location sequence") to direct the desired polypeptide in the host cell, so that the polypeptide accumulates in a specific cellular compartment, subcellular compartment, or membrane. The specific cellular compartments include the apoplast, vacuole, plastids chloroplast, mitochondrion, peroxisomes, secretory pathway, lysosome, endoplasmic reticulum, nucleus or Golgi apparatus. A signal polypeptide or signal sequence is usually at the amino terminus and normally absent from the mature protein due to protease that removes the signal peptide when the polypeptide reaches its final destination. Signal sequences can be a primary sequence located at the N-terminus (125-128), C-terminus (129, 130) or internal (131-133) or tertiary structure (133). If a signal polypeptide or signal sequence to direct the polypeptide does not exist on the vector, it is expected that those of ordinary skill in the art can incorporate the extra nucleotides necessary to encode a signal polypeptide or signal sequence by the ligation of the appropriate nucleotides or by PCR. Those of ordinary skill in the art can identify the nucleotide sequence of a signal polypeptide or signal sequence using computational tools. There are numerous computational tools available for the identification of targeting sequences or signal sequence. These include, but are not limited to, TargetP (134, 135), iPSORT (136), SignalP (137), PrediSi (138), ELSpred (139) HSLpred (140) and PSLpred (141), MultiLoc (142), SherLoc (143), ChloroP (144), MITOPROT (145), Predotar (146) and 3D-PSSM (147). Additional methods and protocols are discussed in the literature (142).

Transformation of Host Cells

Transformation of a plant can be accomplished in a wide variety of ways within the scope of a person of ordinary skill in the art. In one embodiment, a DNA construct is incorporated into a plant by (i) transforming a cell, tissue or organ from a host plant with the DNA construct; (ii) selecting a transformed cell, cell callus, somatic embryo, or seed which contains the DNA construct; (iii) regenerating a whole plant from the selected transformed cell, cell callus, somatic embryo, or seed; and (iv) selecting a regenerated whole plant that expresses the polynucleotide. Many methods of transforming a plant, plant tissue or plant cell for the construction of a transformed cell are suitable. Once transformed, these cells can be used to regenerate transgenic plants. (148)

Those of ordinary skill in the art can use different plant gene transfer techniques found in references for, but not limited to, the electroporation, (149-153) microinjection, (154, 155) lipofection, (156) liposome or spheroplast fusions, (157-159) *Agrobacterium*, (160) direct gene transfer, (161) T-DNA mediated transformation of monocots, (162) T-DNA mediated transformation of dicots, (163, 164) microprojectile bombardment or ballistic particle acceleration, (165-168) chemical transfection including $CaCl_2$ precipitation, polyvinyl alcohol, or poly-L-ornithine, (169) silicon carbide whisker methods, (170, 171) laser methods, (172, 173) sonication methods, (174-176) polyethylene glycol methods, (177) vacuum infiltration (178) and transbacter. (179) Other methods to edit, incorporate or move genes into plant genomes include, but are not limited to, Zinc-finger nucleases (ZFNs),(180, 181) transcription activator like effector nucleases (TALENs) and clustered regularly interspaced short palindromic repeats/Cas (CRISPR/Cas). (182-185)

In one embodiment of the invention, a transformed host cell may be cultured to produce a transformed plant. In this regard, a transformed plant can be made, for example, by transforming a cell, tissue or organ from a host plant with an inventive DNA construct; selecting a transformed cell, cell callus, somatic embryo, or seed which contains the DNA construct; regenerating a whole plant from the selected transformed cell, cell callus, somatic embryo, or seed; and selecting a regenerated whole plant that expresses the polynucleotide.

A wide variety of host cells may be used in the invention, including prokaryotic and eukaryotic host cells. These cells or organisms may include yeast, fungi, algae, microalgae, microbes, invertebrate, vertebrates or photosynthetic organisms. Preferred host cells are eukaryotic, preferably plant cells, such as those derived from monocotyledons, such as duckweed, corn, rice, sugarcane, wheat, bent grass, rye grass, Bermuda grass, Blue grass, and Fescue, or dicotyledons, including canola, cotton, camelina, lettuce, rapeseed, radishes, cabbage, sugarbeet, peppers, broccoli, potatoes and tomatoes, and legumes such as soybeans and bush beans.

One embodiment of the invention is a method for the production of hypotaurine or taurine by the following steps:
1. operably link a promoter to the 5' end of the polynucleotide for a functional CDOL gene product;
2. insert the polynucleotide construct (from step 1 above) into a vector;
3. transform the vector containing the CDOL construct into a plant or plant cell;
4. operably link a promoter to the 5' end of the polynucleotide for the functional SADL gene product;
5. insert the polynucleotide construct (from step 4 above) into a vector; and
6. transform the vector containing the SADL construct into a plant or plant cell carrying a CDOL construct or one that expresses a functional CDOL gene product.

Another embodiment of the invention is a method for the production of hypotaurine or taurine by the following steps:
1. operably link a promoter to the 5' end of the polynucleotide for the functional CDOL gene product;
2. insert the polynucleotide construct (from step 1 above) into a vector;
3. transform the vector containing the CDOL construct into a plant or plant cell;
4. operably link a promoter to the 5' end of the polynucleotide for the functional SADL gene product;
5. insert the polynucleotide construct (from step 4 above) into a vector;
6. transform the vector containing the SADL construct into a plant or plant cell; and
7. Sexually cross a plant (or fuse cells) carrying a CDOL construct or one that expresses a functional CDOL with a plant (or cells) carrying a SADL construct or one that expresses a functional SADL gene product.

Another embodiment of the invention is a method for the production of hypotaurine or taurine by the following steps:
1. In the same vector, operably link a promoter to the 5' end of the polynucleotide for the functional CDOL gene product;
2. operably link a promoter to the 5' end of the polynucleotide for the functional SADL gene product;
3. insert the two polynucleotides into the vector in such a manner that both polynucleotides are expressed by one promoter or each polynucleotide is expressed by one promoter; and
4. transform the vector containing the CDOL and SADL constructs into a plant or plant cell.

Another embodiment of the invention is a method for the production of hypotaurine or taurine by the following steps:
1. operably link a promoter to the 5' end of the polynucleotide for a functional CDOL gene product;
2. insert the polynucleotide construct (from step 1 above) into a vector;
3. transform the vector containing the CDOL construct into a plant or plant cell;
4. operably link a promoter to the 5' end of the polynucleotide for the functional partCS/PLP-DC gene product;
5. insert the polynucleotide construct (from step 4 above) into a vector; and
6. transform the vector containing the partCS/PLP-DC construct into a plant or plant cell carrying a CDOL construct or one that expresses a functional CDOL gene product.

Another embodiment of the invention is a method for the production of hypotaurine or taurine by the following steps:
1. operably link a promoter to the 5' end of the polynucleotide for the functional CDOL gene product;
2. insert the polynucleotide construct (from step 1 above) into a vector;
3. transform the vector containing the CDOL construct into a plant or plant cell;
4. operably link a promoter to the 5' end of the polynucleotide for the functional partCS/PLP-DC gene product;
5. insert the polynucleotide construct (from step 4 above) into a vector;
6. transform the vector containing the partCS/PLP-DC construct into a plant or plant cell; and
7. Sexually cross a plant (or fuse cells) carrying a CDOL construct or one that expresses a functional CDOL with a plant (or cells) carrying a partCS/PLP-DC construct or one that expresses a functional partCS/PLP-DC gene product.

Another embodiment of the invention is a method for the production of hypotaurine or taurine by the following steps:
1. In the same vector, operably link a promoter to the 5' end of the polynucleotide for the functional CDOL gene product;

2. operably link a promoter to the 5' end of the polynucleotide for the functional partCS/PLP-DC gene product;
3. insert the two polynucleotides into the vector in such a manner that both polynucleotides are expressed by one promoter or each polynucleotide is expressed by one promoter; and
4. transform the vector containing the CDOL and partCS/PLP-DC constructs into a plant or plant cell.

Another embodiment of the invention is a method for the production of hypotaurine or taurine by the following steps:
1. operably link a promoter to the 5' end of the polynucleotide for a functional CDOL gene product;
2. insert the polynucleotide construct (from step 1 above) into a vector; transform the vector containing the CDOL construct into a plant or plant cell.

Another embodiment of the invention is a method for the production of hypotaurine or taurine by the following steps:
1. operably link a promoter to the 5' end of the polynucleotide for a functional SADL gene product;
2. insert the polynucleotide construct (from step 1 above) into a vector; transform the vector containing the SADL construct into a plant or plant cell.

Another embodiment of the invention is a method for the production of hypotaurine or taurine by the following steps:
1. operably link a promoter to the 5' end of the polynucleotide for a functional CS/PLP-DC gene product;
2. insert the polynucleotide construct (from step 1 above) into a vector; transform the vector containing the CS/PLP-DC construct into a plant or plant cell.

Suitable Plants

The methods described above may be applied to transform a wide variety of plants, including decorative or recreational plants or crops, but are particularly useful for treating commercial and ornamental crops. Examples of plants that may be transformed in the present invention include, but are not limited to, Acacia, alfalfa, algae, aneth, apple, apricot, artichoke, arugula, asparagus, avocado, banana, barley, beans, beech, beet, Bermuda grass, bent grass, blackberry, blueberry, Blue grass, broccoli, Brussels sprouts, cabbage, camelina, canola, cantaloupe, *carinata*, carrot, cassava, cauliflower, celery, cherry, chicory, cilantro, citrus, clementines, coffee, corn, cotton, cucumber, duckweed, Douglas fir, eggplant, endive, escarole, *eucalyptus*, fennel, fescue, figs, forest trees, garlic, gourd, grape, grapefruit, honey dew, jicama, kiwifruit, lettuce, leeks, lemon, lime, Loblolly pine, maize, mango, melon, mushroom, nectarine, nut, oat, okra, onion, orange, an ornamental plant, *papaya*, parsley, pea, peach, peanut, pear, pepper, persimmon, pine, pineapple, plantain, plum, pomegranate, poplar, potato, pumpkin, quince, *radiata* pine, radicchio, radish, rapeseed, raspberry, rice, rye, rye grass, seaweed, scallion, sorghum, Southern pine, soybean, spinach, squash, strawberry, sugarbeet, sugarcane, sunflower, sweet potato, sweetgum, switchgrass, tangerine, tea, tobacco, tomato, turf, turnip, a vine, watermelon, wheat, yams, and zucchini. Other suitable hosts include bacteria, fungi, algae and other photosynthetic organisms, and animals including vertebrate and invertebrates.

Once transformed, the plant may be treated with other "active agents" either prior to or during the exposure of the plant to stress to further decrease the effects of plant stress. "Active agent," as used herein, refers to an agent that has a beneficial effect on the plant or increases production of amino acid production by the plant. For example, the agent may have a beneficial effect on the plant with respect to nutrition, and the resistance against, or reduction of, the effects of plant stress. Some of these agents may be precursors of end products for reaction catalyzed by CDOL, SADL, CS/PLP-DC, or partCS/PLP-DC. These compounds could promote growth, development, biomass and yield, and change in metabolism. In addition to the twenty amino acids that are involved in protein synthesis specifically sulfur containing amino acids methionine, and cysteine, other amino acids such as glutamate, glutamine, serine, alanine and glycine, sulfur containing compounds such as fertilizer, sulfite, sulfide, sulfate, taurine, hypotaurine, cysteate, 2-sulfacetaldehyde, homotaurine, homocysteine, cystathionine, N-acetyl thiazolidine 4 carboxylic acid (ATCA), glutathione, or bile, or other non-protein amino acids, such as GABA, citrulline and ornithine, or other nitrogen containing compounds such as polyamines may also be used to activate CDOL, SADL, CS/PLP-DC, or partCS/PLP-DC. Depending on the type of gene construct or recombinant expression cassette, other metabolites and nutrients may be used to activate CDOL, SADL, CS/PLP-DC, or partCS/PLP-DC. These include, but are not limited to, sugars, carbohydrates, lipids, oligopeptides, mono- (glucose, arabinose, fructose, xylose, and ribose) di- (sucrose and trehalose) and polysaccharides, carboxylic acids (succinate, malate and fumarate) and nutrients such as phosphate, molybdate, or iron.

Accordingly, the active agent may include a wide variety of fertilizers, pesticides and herbicides known to those of ordinary skill in the art. (186) Other greening agents fall within the definition of "active agent" as well, including minerals such as calcium, magnesium and iron. The pesticides protect the plant from pests or disease and may be either chemical or biological and include fungicides, bactericides, insecticides and anti-viral agents as known to those of ordinary skill in the art.

In some embodiments properties of a transgenic plant are altered using an agent which increases sulfur concentration in cells of the transgenic plant, such as fertilizer, sulfur, sulfite, sulfide, sulfate, taurine, hypotaurine, homotaurine, cysteate, 2-sulfacetaldehyde, N-acetyl thiazolidine 4 carboxylic acid (ATCA), glutathione, and bile. In other embodiments, the agent increases nitrogen concentration. Amino acids either naturally occurring in proteins (e.g., cysteine, methionine, glutamate, glutamine, serine, alanine, or glycine) or which do no naturally occur in proteins (e.g., GABA, citrulline, or ornithine) and/or polyamines can be used for this purpose.

Expression in Prokaryotes

The use of prokaryotes including bacteria, archaebacteria and eubacteria, may be used for this invention, including proteobacteria such as members of Alphaproteobacteria, Betaproteobacteria, Gammaproteobacteria, Deltaproteobacteria, and Epsilonproteobacteria, Other bacteria strains include, but are not limited to, *Bacillus*, (187) *Salmonella, Lactococcus, Streptococcus, Brevibacterium* and *coryneform* bacteria. Some bacteria that can be used for the invention include, but are not limited to, *Bacillus subtilis, Brevibacterium ammoniagene, Corynebacterium crenatum, Corynebacterim pekinese, Corynebacterium glutamicumas, Erwinia citreus, Erwinia herbicola, Escherichia coli, Fusarium venenatum Gluconobacter oxydans, Propionibacterium freudenreicheii*, and *Propionibacterium denitrificans*.(188) Commonly used prokaryotic control sequences include promoters for transcription initiation, optionally with an operator, along with ribosome binding site sequences. Commonly used prokaryotic promoters include the beta lactamase (189), lactose (189), and tryptophan (190) promoters. The vectors usually contain selectable markers to identify transfected or transformed cells. Some commonly used selectable markers include the genes for resistance to ampicillin, tetracycline, or chloramphenicol. The vectors are typically a plasmid or phage. Bacterial cells are transfected or transformed with the plasmid vector DNA. Phage DNA can be infected with phage vector particles or transfected with naked phage DNA. The plasmid and phage DNA for the vectors are commercially available from numerous vendors known to those of ordinary skill in the art. Those of ordinary skill in the art know the molecular techniques and DNA vectors that are used in bacterial systems. (191-193)

Algae and Microalgae

The use of algae and microscopic algae (microphytes or microalgae) can be used for this invention. These include, but are not limited to, diatoms, green algae (Chlorophyta), Euglenophyta, Dinoflagellata, Chrysophyta, Phaeophyta, red algae (Rhodophyta), and Cyanobacteria. Protocols for transfromation as well as commonly used vectors with control sequences include promoters for transcription initiation, optionally with an operator, together with ribosome binding site sequences are known to those of ordinary skill in the art. Vectors that are used in algal or microalgal systems are known to those of ordinary skill in the art. (194-201)

Expression in Non Plant Eukaryotes

The present invention can be expressed in a variety of eukaryotic expression systems such as yeast, insect cell lines, and mammalian cells which are known to those of ordinary skill in the art. For each host system there are suitable vectors that are commercially available (e.g., Agilent Technologies, DNA2.0, GE Healthcare Life Sciences, New England Biolabs, ThermoFisher). The vectors usually have expression control sequences, such as promoters, an origin of replication, enhancer sequences, termination sequences, ribosome binding sites, RNA splice sites, polyadenylation sites, transcriptional terminator sequences, and selectable markers. Synthesis of heterologous proteins and fermentation of products in yeast is well known to those of ordinary skill in the art. (202, 203) Yeast and fungi that can be used include, but are not limited to, *Ashbya gossypii*, *Blakeslea trispora*, *Candida flareri*, *Eremothecium ashbyii*, *Mortierella isabellina*, *Pichia pastoris*, *Saccharomyces cerevisiae* and *Saccyom mycaesess*. Molecular protocols for transformation, and the vectors required for expression in these systems, are known to those of ordinary skill in the art. (204-208)

Invertebrate and vertebrate cells may also be used to express proteins of the present invention. Insect cell lines that include, but are not limited to, black-fly larvae, mosquito larvae, silkworm, armyworm, moth, and *Drosophila* cell lines can be used to express proteins of the present invention using baculovirus-derived vectors. (209) Mammalian cell systems including, but not limited to, monolayers of cells or cell suspensions may also be used to express proteins of the present invention. (210) A number of suitable host cell lines capable of expressing intact proteins have been developed in the art, including the HEK293, BHK21, and CHO cell lines. For each host system there are suitable vectors that are commercially available (BD Boosciences, New England Biolabs, ThermoFisher).

A protein of the present invention, once expressed in any of the non-plant eukaryotic systems can be isolated from the organism by lysing the cells and applying standard protein isolation techniques to the lysates or the pellets. The monitoring of the purification process can be accomplished by using western blot techniques or radioimmunoassay or other standard immunoassay techniques.

Pharmaceutical Compositions

The invention provides pharmaceutical compositions that comprise extracts of one or more transgenic plants described above. Plant extracts containing hypotaurine or taurine can be used to synthesize or manufacture taurine derivatives (211, 212), taurine-conjugates (213) or taurine-polymers (214) that may have a wide range of commercial and medicinal applications. (215) Some taurine derivatives can function as organogelators (216) or dyes (217) and can be used in nanosensor synthesis. (218) Some taurine derivatives have anticonvulsant (211) or anti-cancer (219) properties. Other taurine derivatives are used in the treatment of alcoholism. (220, 221) Taurine-conjugated carboxyethyl-ester-polyrotaxanes increase anticoagulant activity. (222) Taurine-containing polymers may increase wound healing. (223, 224) Taurine linked polymers such as poly gamma-glutamic acid-sulfonates are biodegradable and may have applications in the development of drug delivery systems, environmental materials, tissue engineering, and medical materials. (225) Extracts from taurine-containing plants may be used in pharmaceutical or medicinal compositions to deliver taurine, hypotaurine, taurine-conjugates, or taurine-polymers for use in the treatment of congestive heart failure, high blood pressure, hepatitis, high cholesterol, fibrosis, epilepsy, autism, attention deficit-hyperactivity disorder, retinal degeneration, diabetes, and alcoholism. It is also used to improve mental performance and as an antioxidant.

Pharmaceutically acceptable vehicles of taurine, taurine derivatives, taurine-conjugates, or taurine-polymers are tablets, capsules, gel, ointment, film, patch, powder or dissolved in liquid form.

Nutritional Supplements and Feeds

Transgenic plants containing hypotaurine or taurine may be consumed or used to make extracts for nutritional supplements. Transgenic plant parts that contain hypotaurine or taurine may be used for human consumption. The plant parts may include but are not limited to leaves, stalks, stems, tubers, stolons, roots, petioles, cotyledons, seeds, fruits, grain, strover, nuts, flowers, petioles, pollen, buds, or pods. Extracts from transgenic plants containing hypotaurine or taurine may be used as nutritional supplements, as an antioxidant or to improve physical or mental performance. The extracts may be used in the form of a liquid, powder, capsule or tablet. Other transgenic cells, bacterial, algal, microalgal, fungal, yeast or insects (or insects or larvae) containing taurine may be used in the form of a liquid, powder, capsule or tablet.

Transgenic plants containing hypotaurine or taurine may be used as fish or animal feed or used to make extracts for the supplementation of animal feed. Transgenic plant parts that contain hypotaurine or taurine may be used as animal or fish feed. The plant parts include but are not limited to leaves, stalks, stems, tubers, stolons, roots, petioles, cotyledons, seeds, fruits, grain, strover, nuts, flowers, petioles, buds, pods, or husks. Extracts from transgenic plants containing taurine may be used as feed supplements in the form of a liquid, powder, capsule or tablet. Other transgenic cells, bacterial, algal, microalgal, fungal, yeast or insects (or insects or larvae) containing hypotaurine or taurine may be used as animal or fish feed.

Enhancer of Plant Growth or Yield

Transgenic plant parts that contain hypotaurine or taurine may be used as an enhancer for plant growth or yield. The plant parts include, but are not limited to, leaves, stalks, stems, tubers, stolons, roots, petioles, cotyledons, seeds, fruits, grain, strover, nuts, flowers, petioles, buds, pods, or husks. Extracts from transgenic plants containing hypotaurine or taurine may be used as plant enhancers in the form of a liquid, powder, capsule or tablet. Other transgenic cells, bacterial, algal, microalgal, fungal, yeast or insects (or insects or larvae) containing hypotaurine or taurine may be used as plant enhancers.

Taurine could be purified from the cells or from extracts of the cells or from media from which the cells were grown. The extracted taurine could be used as a food or feed additive, nutrient, pharmaceutical or an enhancer of plant growth or yield. Prokaryotic or eukaryotic cells with the invention can be grown in culture or by fermentation to produce hyptotaurine or taurine. Methods to produce chemical compounds by batch fermentation, fed-batch fermentation, continuous fermentation or in tanks or ponds are well known to one with ordinary skill in the art. (226-237)

Methods such as centrifugation, filtration, crystallization, ion exchange, electrodialysis, solvent extraction, decolorization or evaporation to purify or separate chemical compounds from cells or from liquids or media that grew cells are well known to one with ordinary skill in the art. These methods can be used by one with ordinary skill in the art to purify or separate taurine from cells with the invention, or from liquids or media from which cell suspensions or cell cultures containing the invention were grown. (227, 230, 238-242)

Definitions

The term "polynucleotide" refers to a natural or synthetic linear and sequential array of nucleotides and/or nucleosides, including deoxyribonucleic acid, ribonucleic acid, and derivatives thereof. It includes chromosomal DNA, self-replicating plasmids, infectious polymers of DNA or RNA and DNA or RNA that performs a primarily structural role. Unless otherwise indicated, nucleic acids or polynucleotide are written left to right in 5' to 3' orientation, Nucleotides are referred to by their commonly accepted single-letter codes. Numeric ranges are inclusive of the numbers defining the range.

The terms "amplified" and "amplification" refer to the construction of multiple copies of a nucleic acid sequence or multiple copies complementary to the nucleic acid sequence using at least one of the nucleic acid sequences as a template. Amplification can be achieved by chemical synthesis using any of the following methods, such as solid-phase phosphoramidate technology or the polymerase chain reaction (PCR). Other amplification systems include the ligase chain reaction system, nucleic acid sequence based amplification, Q-Beta Replicase systems, transcription-based amplification system, and strand displacement amplification. The product of amplification is termed an amplicon.

As used herein "promoter" includes reference to a region of DNA upstream from the start of transcription and involved in recognition and binding of RNA polymerase, either I, II or III, and other proteins to initiate transcription. Promoters include necessary nucleic acid sequences near the start site of transcription, such as, in the case of a polymerase II type promoter, a TATA element. A promoter also optionally includes distal enhancer or repressor elements, which can be located as far as several thousand base pairs from the start site of transcription.

The term "plant promoter" refers to a promoter capable of initiating transcription in plant cells.

The term "microbe promoter" refers to a promoter capable of initiating transcription in microbes.

The term "foreign promoter" refers to a promoter, other than the native, or natural, promoter, which promotes transcription of a length of DNA of viral, bacterial or eukaryotic origin, including those from microbes, plants, plant viruses, invertebrates or vertebrates.

The term "microbe" refers to any microorganism (including both eukaryotic and prokaryotic microorganisms), such as fungi, yeast, bacteria, actinomycetes, algae and protozoa, as well as other unicellular structures.

The term "plant" includes whole plants, and plant organs, and progeny of same. Plant organs comprise, e.g., shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like). The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

The term "plant storage organ" includes roots, seeds, tubers, fruits, and specialized stems.

The term "constitutive" refers to a promoter that is active under most environmental and developmental conditions, such as, for example, but not limited to, the CaMV 35S promoter and the nopaline synthase terminator.

The term "tissue-preferred promoter" refers to a promoter that is under developmental control or a promoter that preferentially initiates transcription in certain tissues.

The term "tissue-specific promoter" refers to a promoter that initiates transcription only in certain tissues.

The term "cell-type specific promoter" refers to a promoter that primarily initiates transcription only in certain cell types in one or more organs.

The term "seed-specific promoter" refers to a promoter that primarily initiates transcription only in the seeds.

The term "inducible promoter" refers to a promoter that is under environmental control.

The terms "encoding" and "coding"" refer to the process by which a polynucleotide, through the mechanisms of transcription and translation, provides the information to a cell from which a series of amino acids can be assembled into a specific amino acid sequence to produce a functional polypeptide, such as, for example, an active enzyme or ligand binding protein.

The terms "polypeptide," "peptide," "protein" and "gene product" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. Amino acids may be referred to by their commonly known three-letter or one-letter symbols. Amino acid sequences are written left to right in amino to carboxy orientation, respectively. Numeric ranges are inclusive of the numbers defining the range.

The terms "residue," "amino acid residue," and "amino acid" are used interchangeably herein to refer to an amino acid that is incorporated into a protein, polypeptide, or peptide. The amino acid may be a naturally occurring amino acid and may encompass known analogs of natural amino acids that can function in a similar manner as the naturally occurring amino acids.

The terms "cysteine dioxygenase" and "CDO" refer to the protein (EC:1.13.11.20) that catalyzes the following reaction:

cysteine+oxygen=3-sulfinoalanine

NOTE: 3-sulfinoalanine is another name for cysteine sulfinic acid, cysteine sulfinate, 3-sulphino-L-alanine, 3-sulfino-alanine, 3-sulfino-L-alanine, L-cysteine sulfinic acid, L-cysteine sulfinic acid, cysteine hydrogen sulfite ester or alanine 3-sulfinic acid.

The terms "sulfinoalanine decarboxylase" and "SAD" refer to the protein (4.1.1.29) that catalyzes the following reaction:

3-sulfinoalanine=hypotaurine+CO$_2$

NOTE: SAD is another name for cysteine-sulfinate decarboxylase, L-cysteine sulfinic acid decarboxylase, cysteine-sulfinate decarboxylase, CADCase/CSADCase, CSAD, cysteic decarboxylase, cysteine sulfinic acid decarboxylase, cysteine sulfinate decarboxylase, sulfoalanine decarboxylase, sulphinoalanine decarboxylase, and 3-sulfino-L-alanine carboxy-lyase.

NOTE: the SAD reaction is also catalyzed by GAD (4.1.1.15) (glutamic acid decarboxylase or glutamate decarboxylase).

Other names for hypotaurine are 2-aminoethane sulfinate, 2-aminoethylsulfinic acid, and 2-aminoethanesulfinic acid.

Other names for taurine are 2-aminoethane sulfonic acid, aminoethanesulfonate, L-taurine, taurine ethyl ester, and taurine ketoisocaproic acid 2-aminoethane sulfinate.

The terms "cysteamine dioxygenase" and "ADO" refer to the protein (EC 1.13.11.19) that catalyzes the following reaction:

2-aminoethanethiol+O$_2$=hypotaurine

ADO is another name for 2-aminoethanethiol:oxygen oxidoreductase, persulfurase, cysteamine oxygenase, and cysteamine:oxygen oxidoreductase.

Other names for 2-aminoethanethiol are cysteamine or 2-aminoethane-1-thiol, b-mercaptoethylamine, 2-mercaptoethylamine, decarboxycysteine, and thioethanolamine.

The terms "taurine-pyruvate aminotransferase" and "TPAT" refer to the protein (EC 2.6.1.77) that catalyzes the following reaction:

L-alanine+2-sulfoacetaldehyde=taurine+pyruvate

TPAT is another name for taurine transaminase or Tpa.

The terms "sulfoacetaldehyde acetyltransferase" and "SA" refer to the protein (EC:2.3.3.15) that catalyzes the following reaction:

acetyl phosphate+sulfite=sulfoacetaldehyde+orthophosphate

SA is another name for acetyl-phosphate:sulfite S-acetyltransferase or Xsc.

The terms "taurine dehydrogenase" and "TDeHase" refer to the protein (EC:1.4.2.-) that catalyzes the following reaction:

ammonia+2-sulfoacetaldehyde=taurine+water

TDeHase is another name for taurine:oxidoreductase, taurine:ferricytochrome-c oxidoreductase, tauX or tauY.

The terms "taurine dioxygenase" and "TDO" refer to the protein (EC:1.14.11.17) that catalyzes the following reaction:

sulfite+aminoacetaldehyde+succinate+CO$_2$=taurine+2-oxoglutarate+O$_2$

TDO is another name for 2-aminoethanesulfonate dioxygenase, alpha-ketoglutarate-dependent taurine dioxygenase, taurine, 2-oxoglutarate:O$_2$ oxidoreductase or tauD.

2-oxoglutarate is another name for alpha-ketoglutarate.

The term "functional" with reference to CDOL, SADL, CS/PLP-DC, ADO, TPAT, SA, ssTDeHase, lsTDeHase or CS/PLP-DC refers to peptides, proteins or enzymes that catalyze the CDOL, SADL, GAD, ADO, TPAT, SA, TDeHase or CS/PLP-DC reactions, respectively.

The terms "cysteine synthetase/PLP decarboxylase" and "CS/PLP-DC" refer to the protein that catalyzes the following reactions:

cysteine+oxygen=hypotaurine cysteine+oxygen=taurine

O-acetyl-L-serine+hydrogen sulfide=hypotaurine

O-acetyl-L-serine+hydrogen sulfide=taurine

The terms "portion of the cysteine synthetase/PLP decarboxylase" and "partCS/PLP-DC" refers to the protein that catalyzes a decarboxylase reaction which cleaves carbon-carbon bonds and includes, but is not limited to, the following substrate and end-products:

Aspartate=beta-alanine+CO$_2$

Glutamate=4-aminobutanoate+CO$_2$

Cysteic acid=2-aminoethane sulfonate+CO$_2$

Note: another name for 4-aminobutanoate is gamma-aminobutyric acid (GABA).

The term "recombinant" includes reference to a cell or vector that has been modified by the introduction of a heterologous nucleic acid. Recombinant cells express genes that are not normally found in that cell or express native genes that are otherwise abnormally expressed, underexpressed, or not expressed at all as a result of deliberate human intervention, or expression of the native gene may have reduced or eliminated as a result of deliberate human intervention.

The term "recombinant expression cassette" refers to a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "transgenic plant" includes reference to a plant, which comprises within its genome a heterologous polynucleotide. Generally, the heterologous polynucleotide is integrated within the genome such that the polynucleotide is passed on to successive generations. The heterologous polynucleotide may be integrated into the genome alone or as part of a recombinant expression cassette. "Transgenic" is also used to include any cell, cell line, callus, tissue, plant part or plant, the genotype of which has been altered by the presence of heterologous nucleic acid including those transgenic plants altered or created by sexual crosses or asexual propagation from the initial transgenic plant. The term "transgenic" does not encompass the alteration of the genome by conventional plant breeding methods or by naturally occurring events such as random cross-fertilization, non-recombinant viral infection, non-recombinant bacterial transformation, non-recombinant transposition, or spontaneous mutation.

The term "vector" includes reference to a nucleic acid used in transfection or transformation of a host cell and into which can be inserted a polynucleotide.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity, and most preferably 100% sequence identity (i.e., complementary) with each other.

The terms "stringent conditions" and "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt solution. Low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Moderate stringency conditions include hybridization in 40 to 45% formamide, 1 M NaCl, 1% SDS at 37° C., and a wash in 0.5× to 1×SSC at 55 to 60° C. High stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated (243), where the $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill in the art will understand that variations in the stringency of hybridization and/or wash solutions are inherently described. An extensive guide to the hybridization of nucleic acids is found in the scientific literature (115, 244). Unless otherwise stated, in the present application high stringency is defined as hybridization in 4×SSC, 5×Denhardt solution (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

The following terms are used to describe the sequence relationships between two or more nucleic acids or polynucleotides or polypeptides: "reference sequence," "comparison window," "sequence identity," "percentage of sequence identity," and "substantial identity."

The term "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "comparison window" includes reference to a contiguous and specified segment of a polynucleotide sequence, where the polynucleotide sequence may be compared to a reference sequence and the portion of the polynucleotide sequence in the comparison window may comprise additions or deletions (i.e., gaps) when it is compared to the reference sequence for optimal alignment. The comparison window is usually at least 20 contiguous nucleotides in length, and optionally can be 30, 40, 50, 100 or longer. Those of ordinary skill in the art understand that the inclusion of gaps in a polynucleotide sequence alignment introduces a gap penalty, and it is subtracted from the number of matches.

Methods of alignment of nucleotide and amino acid sequences for comparison are well known to those of ordinary skill in the art. The local homology algorithm, BES1FIT, (245) can perform an optimal alignment of sequences for comparison using a homology alignment algorithm called GAP (246), search for similarity using Tfasta and Fasta (247), by computerized implementations of these algorithms widely available on-line or from various vendors (Intelligenetics, Genetics Computer Group). CLUSTAL allows for the alignment of multiple sequences (248-250) and program PileUp can be used for optimal global alignment of multiple sequences (251). The BLAST family of programs can be used for nucleotide or protein database similarity searches. BLASTN searches a nucleotide database using a nucleotide query. BLASTP searches a protein database using a protein query. BLASTX searches a protein database using a translated nucleotide query that is derived from a six-frame translation of the nucleotide query sequence (both strands). TBLASTN searches a translated nucleotide database using a protein query that is derived by reverse-translation. TBLASTX search a translated nucleotide database using a translated nucleotide query.

GAP (246) maximizes the number of matches and minimizes the number of gaps in an alignment of two complete sequences. GAP considers all possible alignments and gap positions and creates the alignment with the largest number of matched bases and the fewest gaps. It also calculates a gap penalty and a gap extension penalty in units of matched bases. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62. (252)

Unless otherwise stated, sequence identity or similarity values refer to the value obtained using the BLAST 2.0 suite of programs using default parameters. (253) As those of ordinary skill in the art understand that BLAST searches assume that proteins can be modeled as random sequences and that proteins comprise regions of nonrandom sequences, short repeats, or enriched for one or more amino acid residues, called low-complexity regions. These low-complexity regions may be aligned between unrelated proteins even though other regions of the protein are entirely dissimilar. Those of ordinary skill in the art can use low-complexity filter programs to reduce number of low-complexity regions that are aligned in a search. These filter programs include, but are not limited to, the SEG (254, 255) and XNU. (256)

The terms "sequence identity" and "identity" are used in the context of two nucleic acid or polypeptide sequences and include reference to the residues in the two sequences, which are the same when ali ed for maximum correspondence over a specified comparison window. When the percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conserved substitutions, the percent sequence identity may be adjusted upwards to correct for the conserved nature of the substitution. Sequences, which differ by such conservative substitutions, are said to have "sequence similarity" or "similarity." Scoring for a conservative substitution allows for a partial rather than a full mismatch, (257) thereby increasing the percentage sequence similarity.

The term "percentage of sequence identity" means the value determined by comparing two optimally aligned sequences over a comparison window, wherein the portion of the polynucleotide sequence in the comparison window may comprise gaps (additions or deletions) when compared to the reference sequence for optimal alignment. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90%, and most preferably at least 95%, compared to a reference sequence using one of the alignment programs described using standard parameters. One of ordinary skill in the art will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 50-100%. Another indication that nucleotide sequences are substantially identical is if two molecules hybridize to each low stringency conditions, moderate stringency conditions or high stringency conditions. Yet another indication that two nucleic acid sequences are substantially identical is if the two polypeptides immunologically cross-react with the same antibody in a western blot, immunoblot or ELISA assay.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm (246). Thus, a peptide is substantially identical to a second peptide, for example, where the two peptides differ only by a conserved substitution. Another indication that amino acid sequences are substantially identical is if two polypeptides immunologically cross-react with the same antibody in a western blot, immunoblot or ELISA assay. In addition, a peptide can be substantially identical to a second peptide when they differ by a non-conservative change if the epitope that the antibody recognizes is substantially identical.

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention

REFERENCES

1. Abbott P C, Hurt C, & Tyner W E (2011) What's driving food prices in 2011? *Farm Foundation Issue Report* (July).
2. Sturman J A (1988) Taurine in development. *Journal of Nutrition* 118:1169-1176.
3. Sturman J A & Hayes K C (1980) The biology of taurine in nutrition and development. *Advances in Nutritional Research* 3:231-299.
4. Chen X C, Pan Z L, Liu D S, & Han X (1998) Effect of taurine on human fetal neuron cells: Proliferation and differentiation. *Advances in Experimental Medicine and Biology* 442:397-403.
5. El Idrissi A & Trenkner E (1999) Growth factors and taurine protect against excitotoxicity by stabilizing calcium homeostasis and energy metabolism. *Journal of Neuroscience* 19:9459-9468.
6. El Idrissi A & Trenkner E (2003) Taurine regulates mitochondrial calcium homeostasis. *Advances in Experimental Medicine and Biology* 526:527-536.
7. Trenkner E (1990) Possible role of glutamate with taurine in neuron-glia interaction during cerebellar development. *Progress in Clinical and Biological Research* 351:133-140.
8. Wu H, et al. (2005) Mode of action of taurine as a neuroprotector. *Brain Research* 1038:123-131.
9. Schaffer S, Takahashi K, & Azuma J (2000) Role of osmoregulation in the actions of taurine. *Amino Acids* 19:527-546.
10. Chapman R A, Suleiman M S, & Earm Y E (1993) Taurine and the heart. *Cardiovascular Research* 27:358-363.
11. Tabassuma H, Rehmana H, Banerjeeb B D, Raisuddina S, & Parvez S (2006) Attenuation of tamoxifen-induced hepatotoxicity by taurine in mice. *Clinica Chimica Acta* 370:129-136.
12. Rocket N, et al. (2007) The osmolyte taurine protects against ultraviolet B radiation-induced immunosuppression. *Journal of Immunology* 179:3604-3612.
13. Knopf K, Sturman J A, Armstrong M, & Hayes A C (1978) Taurine: An essential nutrient for the cat. *Journal of Nutrition* 108:773-778.
14. Morris J G, Rogers Q R, & Pacioretty L M (1990) Taurine: an essential nutrient for cats. *Journal of Small Animal Practice* 31(10):502-509.
15. Chesney R, et al. (1998) The Role of Taurine in Infant Nutrition. *Taurine* 3, Advances in Experimental Medicine and Biology, eds Schaffer S, Lombardini J, & Huxtable R (Springer U S), Vol 442, pp 463-476.
16. Gibson G T, et al. (2007) Supplementation of taurine and methionine to all-plant protein diets for rainbow trout (*Oncorhynchus mykiss*). *Aquaculture* 269:514-524.
17. Buentello A, Jirsa D, Barrows F T, & Drawbridge M (2015) Minimizing fishmeal use in juvenile California yellowtail, Seriola lalandi, diets using non-G M soybeans selectively bred for aquafeeds. *Aquaculture* 435(0):403-411.
18. Rossi W, Moxely D, Buentello A, Pohlenz C, & Gatlin D M (2013) Replacement of fishmeal with novel plant feedstuffs in the diet of red drum Sciaenops ocellatus: an assessment of nutritional value. *Aquaculture Nutrition* 19:72-81.
19. Watson A M, Buentello A, & Place A R (2014) Partial replacement of fishmeal, poultry by-product meal and soy protein concentrate with two non-genetically modified soybean cultivars in diets for juvenile cobia, Rachycentron canadum. *Aquaculture* 434(0):129-136.
20. Takagia S, et al. (2008) Taurine is an essential nutrient for yellowtail Seriola quinqueradiata fed non-fish meal diets based on soy protein concentrate. *Aquaculture* 280: 198-205.
21. Lunger A N, McLean E, Gaylord T G, Kuhn D, & Craig S R (2007) Taurine supplementation to alternative dietary proteins used in fish meal replacement enhances growth of juvenile cobia (*Rachycentron canadum*). *Aquaculture* 271:401-410.
22. Watson A M, Barrows Fr, & Place A R (2013) Taurine supplementation of plant derived protein and n-3 fatty acids are critical for optimal growth and development of cobia, Rachycentron canadum. *Lipids* 48(9):899-913.
23. Watson A M, Barrows F T, & Place A R (2013) Taurine supplemented plant protein based diets with alternative lipid sources for juvenile gilthead sea bream, *Sparus aurata*. Journal of Fisheries and *Aquaculture* 4:59-66.
24. Park G S, Takeuchi T, Yokoyama M, & Seikai T (2002) Optimal dietary taurine level for growth of juvenile Japanese flounder *Paralichthys olivaceus*. *Fisheries Science* 68:824-829.
25. Gaylord T G, Teague A M, & Barrows F T (2006) Taurine supplementation of all-plant protein diets for rainbow trout (*Oncorhynchus mykiss*). *Journal of the World Aquaculture Society* 37:509-517.
26. Salze G P & Davis D A (2015) Taurine: a critical nutrient for future fish feeds. *Aquaculture* 437:215-229.
27. Yang H, Tian L, Huang J, Liang G, & Liu Y (2013) Dietary taurine can improve the hypoxia-tolerance but not the growth performance in juvenile grass carp *Ctenopharyngodon idellus*. *Fish physiology and biochemistry* 39(5): 1071-1078.
28. Kuz'mina V V, Gavrovskaya L K, Rusanova P V, Kulivatskaya E A, & Ryzhova O V (2011) Effect of taurine on the glycemia level and the activity of hydrolases in the intestinal mucosa in carp (*Cyprinus carpio* L.). *Inland Water Biol* 4(2):242-248.
29. Yue Y-R, et al. (2012) The effect of dietary taurine supplementation on growth performance, feed utilization and taurine contents in tissues of juvenile white shrimp (*Litopenaeus vannamei*, Boone, 1931) fed with low-fishmeal diets. *Aquaculture Research DOI:* 10.1111/j.1365-2109.2012.03135.x.
30. Brotons Martinez J, Chatzifotis S, Divanach P, & Takeuchi T (2004) Effect of dietary taurine supplementation on growth performance and feed selection of sea bass Dicentrarchus labrax fry fed with demand-feeders. *Fisheries Science* 70(1):74-79.
31. Milei J, et al. (1992) Reduction of reperfusion injury with preoperative rapid intravenous infusion of taurine during myocardial revascularization. *American Heart Journal* 123:339-345.
32. Militante J D & Lombardini J B (2002) Treatment of hypertension with oral taurine. *Endocrinology* 147:3276-3284.
33. Fujita T, Ando K, Noda H, Ito Y, & Sato Y (1987) Effects of increased adrenomedullary activity and taurine in young patients with borderline hypertension. *Circulation* 75:525-532.
34. McCown T J, Givens B S, & Breese G R (1987) Amino acid influences on seizures elicited within the inferior colliculus. *Pharmacology and Experimental Therapeutics* 243:603-608.
35. Matsuyama Y, Morita T, Higuchi M, & Tsujii T (1983) The effect of taurine administration on patients with acute hepatitis. *Progress in Clinical and Biological Research* 125:461-468.
36. Ikeda H (1977) Effects of taurine on alcohol withdrawal. *Lancet* 2:509.
37. Franconi F, Di Leo M A S, Bennardini F, & Ghirlanda G (2004) Is taurine beneficial in reducing risk factors for diabetes mellitus? *Neurochemical Research* 29:143-150.
38. Paula-Lima A C, De Felice F G, Brito-Moreira J, & Ferreira S T (2005) Activation of GABAA receptors by taurine and muscimol blocks the neurotoxicity of [beta]-amyloid in rat hippocampal and cortical neurons. *Neuropharmacology* 49:1140-1148.
39. Nakamori K, et al. (1993) Quantitative evaluation of the effectiveness of taurine in protecting the ocular surface against oxidant. *Chemical &Pharmaceutical Bulletin* 41:335-338.

40. Zhang M, et al. (2004) Beneficial effects of taurine on serum lipids in overweight or obese non-diabetic subjects. *Amino Acids* 26:267-271.
41. Yokogoshi H, et al. (1999) Dietary taurine enhances cholesterol degradation and reduces serum and liver cholesterol concentrations in rats fed a high-cholesterol diet. *Journal of Nutrition* 129:1705-1712.
42. Yamamoto K, et al. (2000) Dietary taurine decreases hepatic secretion of cholesterol ester in rats fed a high-cholesterol diet. *Pharmacology* 60:27-33.
43. Green T R, Fellman J H, Eicher A L, & Pratt K L (1991) Antioxidant role and subcellular location of hypotaurine and taurine in human neutrophils. *Biochimica et Biophysica Acta* 1073:91-97.
44. Giirer H, Ozgiines H, Saygin E, & Ercal N (2001) Antioxidant effect of taurine against lead-induced oxidative stress. *Archives of Environmental Contamination and Toxicology* 41:397-402.
45. Das J, Ghosh J, Manna P, & Sil P C (2008) Taurine provides antioxidant defense against NaF-induced cytotoxicity in murine hepatocytes. *Pathophysiology* 15:181-190.
46. Zhang M, et al. (2004) Role of taurine supplementation to prevent exercise-induced oxidative stress in healthy young men. *Amino Acids* 26:203-207.
47. Williams M (2005) Dietary supplements and sports performance: Amino acids. *Journal of the International Society of Sports Nutrition* 2:63-67.
48. da Silva D L P, et al. (2008) Penetration profile of taurine in the human skin and its distribution in skin layers. *Pharmaceutical Research* 25:1846-1850.
49. Suzuki A, Kajita T, & Furushima M (1989) 4877447.
50. Honjoh K I, et al. (2010) Enhancement of menadione stress tolerance in yeast by accumulation of hypotaurine and taurine: co-expression of cDNA clones, from *Cyprinus carpio*, for cysteine dioxygenase and cysteine sulfinate decarboxylase in *Saccharomyces cerevisiae*. *Amino Acids* 38:1173-1183.
51. Turano F J, Turano K A, Carlson P S, & Kinnersley A M (2012) U.S. Pat. No. 9,267,148.
52. Turano F J, Price M B, & Turano K A (2014). U.S. Pat. No. 9,267,148.
53. Tevatia R, et al. (2015) The taurine biosynthetic pathway of microalgae. *Algal Research* 9:21-26.
54. Murray E E, Lotzer J, & Eberle M (1989) Codon usage in plant genes. *Nucleic Acids Research* 17:477-498.
55. Langenheim J H & Thimann K V (1982) *Botany: Plant Biology and its Relation to Human Affairs* (John Wiley & Sons Inc., New York).
56. Vasil I K (1984) *Cell Culture and Somatic Cell Genetics of Plants: Laboraory Procedures and Their Applications* (Academic Press, Orlando).
57. Stanier R, Ingrahm J, Wheelis M, & Painter P (1986) *The Microbial World* (Prentice-Hall, New Jersey) 5 Ed.
58. Dhringra O D & Sinclair J B (1985) *Basic plant pathology methods* (CRC Press, Boca Raton, Fla.).
59. Maniatis T, Fritsch E F, & Sambrook J (1985) *Molecular Cloning: A Laboratory Manual: DNA Cloning* (Cold Spring Harbor, N.Y.).
60. Gait (1984) *Oligonucleotide Synthesis—A Practical Approach* (IRL Press, Washington, D.C.).
61. Hames D D & Higgins S J (1984) *Nucleic Acid Hybridization: A Practical Approach* (IRL Press, Washington D.C.).
62. Watson J D, Gilman M, Witowski J, & Zoller M (1992) *Recombinant DNA* (Scientific American Books, New York).
63. Szewczyk E, et al. (2006) Fusion PCR and gene targeting in *Aspergillus nidulans*. *Nature Protocols* 1:3111-3121.
64. Ho S N, Hunt H D, Horton R M, Pullen J K, & Pease L R (1989) Site-directed mutagenesis by overlap extension using the polymerase chain reaction. *Gene* 77:51-59.
65. Fuhrmann M, Oertel W, & Hegemann P (1999) A synthetic gene coding for the green fluorescent protein (GFP) is a versatile reporter in *Chlamydomonas reinhardtii*. *Plant Journal* 19:353-361.
66. Mandecki W & Bolling T J (1988) Fold method of gene synthesis. *Gene* 68:101-107.
67. Stemmer W P, Crameri, A., Ha, K. D., Brennan, T. M. and Heyneker, H. L. (1995) Single-step assembly of a gene and entire plasmid from large numbers of oligodeoxyribonucleotides. *Gene* 164:49-53.
68. Gao X, Yo P, Keith A, Ragan T J, & Harris T K (2003) Thermodynamically balanced inside-out (TBIO) PCR-based gene synthesis: a novel method of primer design for high-fidelity assembly of longer gene sequences. *Nucleic Acids Research* 31:e143.
69. Young L & Dong Q (2004) Two-step total gene synthesis method. *Nucleic Acids Research* 32:e59.
70. Trinh R, Gurbaxani B, Morrison S L, & Seyfzadeh M (2004) Optimization of codon pair use within the (GGGGS)3 linker sequence results in enhanced protein expression. *Molecular immunology* 40(10):717-722.
71. Chang T W & Yu L (1999) *Genetic engineering*. (Google Patents).
72. Kuusinen A, Arvola M, & Keinanen K (1995) Molecular dissection of the agonist binding site of an AMPA receptor. *Embo J* 14(24):6327-6332.
73. Robinson C R & Sauer R T (1998) Optimizing the stability of single-chain proteins by linker length and composition mutagenesis. *Proc Natl Acad Sci USA* 95(11):5929-5934.
74. Armstrong N & Gouaux E (2000) Mechanisms for activation and antagonism of an AMPA-sensitive glutamate receptor: crystal structures of the GluR2 ligand binding core. *Neuron* 28(1):165-181.
75. Arai R, Ueda H, Kitayama A, Kamiya N, & Nagamune T (2001) Design of the linkers which effectively separate domains of a bifunctional fusion protein. *Protein Eng* 14(8):529-532.
76. Wriggers W, Chakravarty S, & Jennings P A (2005) Control of protein functional dynamics by peptide linkers. *Biopolymers* 80(6):736-746.
77. Reddy Chichili V P, Kumar V, & Sivaraman J (2013) Linkers in the structural biology of protein-protein interactions. *Protein Sci* 22(2):153-167.
78. van Der Krol A R, et al. (1999) Developmental and wound-, cold-, desiccation-, ultraviolet-B-stress-induced modulations in the expression of the *petunia* zinc finger transcription factor gene ZPT2-2. *Plant Physiology* 121(4):1153-1162.
79. Shinmyo A, et al. (1998) Metabolic engineering of cultured tobacco cells. *Biotechnology and Bioengineering* 58(2-3):329-332.
80. Sohal A K, Pallas J A, & Jenkins G I (1999) The promoter of a *Brassica napus* lipid transfer protein gene is active in a range of tissues and stimulated by light and viral infection in transgenic *Arabidopsis*. *Plant Molecular Biology* 41(1):75-87.
81. Cormack R S, et al. (2002) Leucine zipper-containing WRKY proteins widen the spectrum of immediate early elicitor-induced WRKY transcription factors in parsley. *Biochimica et Biophysica Acta* 1576(1-2):92-100.

82. Eulgem T, Rushton P J, Schmelzer E, Hahlbrock K, & Somssich I E (1999) Early nuclear events in plant defence signalling: rapid gene activation by WRKY transcription factors. *EMBO (European Molecular Biology Organization) Journal* 18(17):4689-4699.
83. Lebel E, et al. (1998) Functional analysis of regulatory sequences controlling PR-1 gene expression in *Arabidopsis*. Plant Journal 16(2):223-233.
84. Ngai N, Tsai F Y, & Coruzzi G (1997) Light-induced transcriptional repression of the pea AS1 gene: identification of cis-elements and transfactors. *Plant Journal* 12(5):1021-1034.
85. Kucho K, Ohyama K, & Fukuzawa H (1999) CO(2)-responsive transcriptional regulation of CAH1 encoding carbonic anhydrase is mediated by enhancer and silencer regions in *Chlamydomonas reinhardtii*. *Plant Physiology* 121(4):1329-1338.
86. Kucho K, Yoshioka S, Taniguchi F, Ohyama K, & Fukuzawa H (2003) Cis-acting elements and DNA-binding proteins involved in CO2-responsive transcriptional activation of Cah1 encoding a periplasmic carbonic anhydrase in *Chlamydomonas reinhardtii*. *Plant Physiology* 133(2):783-793.
87. Chen W, Chao G, & Singh K B (1996) The promoter of a H2O2-inducible, *Arabidopsis* glutathione S-transferase gene contains closely linked OBF- and OBP1-binding sites. *Plant Journal* 10(6):955-966.
88. Chen W & Singh K B (1999) The auxin, hydrogen peroxide and salicylic acid induced expression of the *Arabidopsis* GST6 promoter is mediated in part by an ocs element. *Plant Journal* 19(6):667-677.
89. Lu C A, Lim E K, & Yu S M (1998) Sugar response sequence in the promoter of a rice alpha-amylase gene serves as a transcriptional enhancer. *J Biol Chem* 273(17): 10120-10131.
90. Leubner-Metzger G, Petruzzelli L, Waldvogel R, *Vogeli-Lange* R, & Meins F, Jr. (1998) Ethylene-responsive element binding protein (EREBP) expression and the transcriptional regulation of class I beta-1,3-glucanase during tobacco seed germination. *Plant Molecular Biology* 38(5):785-795.
91. Kridl J C, et al. (1991) Isolation and characterization of an expressed napin gene from *Brassica rapa*. *Seed Science Research* 1(04):209-219.
92. Zavallo D, Lopez Bilbao M, Hopp H E, & Heinz R (2010) Isolation and functional characterization of two novel seed-specific promoters from sunflower (*Helianthus annuus* L.). *Plant cell reports* 29(3):239-248.
93. Kim M J, et al. (2006) Seed-specific expression of sesame microsomal oleic acid desaturase is controlled by combinatorial properties between negative cis-regulatory elements in the SeFAD2 promoter and enhancers in the 5'-UTR intron. *Molecular genetics and genomics: MGG* 276(4):351-368.
94. Bustos M M, et al. (1989) Regulation of beta-glucuronidase expression in transgenic tobacco plants by an A/T-rich, cis-acting sequence found upstream of a French bean beta-phaseolin gene. *Plant Cell* 1(9):839-853.
95. Fujiwara T & Beachy R N (1994) Tissue-specific and temporal regulation of a beta-conglycinin gene: roles of the R Y repeat and other cis-acting elements. *Plant Mol Biol* 24(2):261-272.
96. Wienand U, Langridge P, & Feix G (1981) Isolation and characterization of a genomic sequence of maize coding for a zein gene. *Molec. Gen. Genet.* 182(3):440-444.
97. Takaiwa F, Oono K, Wing D, & Kato A (1991) Sequence of three members and expression of a new major subfamily of glutelin genes from rice. *Plant Molecular Biology* 17(4): 875-885.
98. Hudspeth R L, Grula J W, Dai Z, Edwards G E, & Ku M S (1992) Expression of maize phosphoenolpyruvate carboxylase in transgenic tobacco: Effects on biochemistry and physiology. *Plant Physiology* 98(2):458-464.
99. de Framond A J (1991) A metallothionein-like gene from maize (*Zea mays*). Cloning and characterization. *FEBS Letters* 290(1-2):103-106.
100. Hudspeth R L, Hobbs S L, Anderson D M, Rajasekaran K, & Grula J W (1996) Characterization and expression of metallothionein-like genes in cotton. *Plant Molecular Biology* 31(3):701-705.
101. Herrera-Estrella L, Depicker A, van Montagu M, & Schell J (1983) Expression of chimaeric genes transferred into plant cells using a Ti-plasmid-derived vector. *Nature* 303:209-213.
102. Pathirana M S, et al. (1997) Analyses of phosphoenolpyruvate carboxylase gene structure and expression in alfalfa nodules. *Plant Journal* 12(2):293-304.
103. Yang S H, Yu H, & Goh C J (2002) Isolation and characterization of the orchid cytokinin oxidase DSCKX1 promoter. *Journal of Experimental Botany* 53:1899-1907.
104. Moon H & Callahan A M (2004) Developmental regulation of peach ACC oxidase promoter—GUS fusions in transgenic tomato fruits. *Journal of Experimental Botany* 55:1519-1528.
105. Avsian-Kretchmer O, Gueta-Dahan Y, Lev-Yadun 5, Gollop R, & Ben-Hayyim G (2004) The salt-stress signal transduction pathway that activates the gpxl promoter is mediated by intracellular H2O2, different from the pathway induced by extracellular H2O2. *Plant Physiology* 135(3):1685-1696.
106. Wu A-M, Lv S-Y, & Liu J-Y (2007) Functional analysis of a cotton glucuronosyltransferase promoter in transgenic tobaccos. *Cell Research* 17:174-183.
107. Hatzfeld Y (2014) U.S. Pat. No. 8,779,237.
108. Franklin S, Somanchi A, Espina K, Rudenko G, & Chua P (2014) U.S. Pat. No. 8,674,180.
109. Feng P C C, Malven M, & Flasinski S (2013) U.S. Pat. No. 8,420,888.
110. Manjunath S, et al. (2012) U.S. Pat. No. 8,138,393.
111. Lee D W, et al. (2008) *Arabidopsis* Nuclear-Encoded Plastid Transit Peptides Contain Multiple Sequence Subgroups with Distinctive Chloroplast-Targeting Sequence Motifs. *The Plant Cell* 20(6):1603-1622.
112. von Heijne G, et al. (1991) CHLPEP: a database of chloroplast transit peptides. *Plant Mol Biol Rep* 9:104-126.
113. An G, Watson B D, Stachel S, Gordon M P, & Nester E W (1985) New cloning vehicles for transformation of higher plants. *EMBO (European Molecular Biology Organization)Journal* 4:277-284.
114. Gruber M Y & Cosby W L (1993) Vectors for plant transformation. *Methods in Plant Molecular Biology and Biotechnology*, eds Glick B R & Thompson J E (CRC Press, Baco Raton, Fla.), pp 89-119.
115. Ausubel F M, et al. (1995) *Current Protocols in Molecular Biology* (Greene Publishing and Wiley-Interscience, New York).
116. Newman T C, Ohme-Takagi M, Taylor C B, & Green P J (1993) DST sequences, highly conserved among plant SAUR genes, target reporter transcripts for rapid decay in tobacco. *Plant Cell* 5(6):701-714.

117. Ohme-Takagi M, Taylor C B, Newman T C, & Green Pi (1993) The effect of sequences with high A U content on mRNA stability in tobacco. *Proceedings of the National Academy of Sciences of the United States of America* 90(24):11811-11815.
118. Nagaya S, Kawamura K, Shinmyo A, & Kato K (2010) The HSP Terminator of *Arabidopsis thaliana* Increases Gene Expression in Plant Cells. *Plant and Cell Physiology* 51(2):328-332.
119. Mogen B D, MacDonald M H, Graybosch R, & Hunt A G (1990) Upstream sequences other than AAUAAA are required for efficient messenger RNA 3'-end formation in plants. *Plant Cell* 2(12):1261-1272.
120. Mogen B D, MacDonald M H, Leggewie G, & Hunt A G (1992) Several distinct types of sequence elements are required for efficient mRNA 3' end formation in a pea rbcS gene. *Mol Cell Biol* 12(12):5406-5414.
121. Rothnie H M, Reid J, & Hohn T (1994) The contribution of AAUAAA and the upstream element UUUGUA to the efficiency of mRNA 3'-end formation in plants. *Embo j* 13(9):2200-2210.
122. Bassett C L (2007) *Regulation of Gene Expression in Plants: The Role of Transcript Structure and Processing* (Springer Press, New York).
123. Gutierrez R A, Macintosh G C, & Green P J (1999) Current perspectives on mRNA stability in plants: multiple levels and mechanisms of control. *Trends in Plant Science* 4:429-438.
124. Ingelbrecht I L, Herman L M, Dekeyser R A, Van Montagu M C, & Depicker A G (1989) Different 3' end regions strongly influence the level of gene expression in plant cells. *Plant Cell* 1:671-680.
125. von Heijne G (1986) Mitochondrial targeting sequences may form amphiphilic helices. *EMBO (European Molecular Biology Organization)Journal* 5:1335-1342.
126. Swinkels B W, Gould S J, Bodnar A G, Rachubinski R A, & Subramani S (1991) A novel, cleavable peroxisomal targeting signal at the amino-terminus of the rat 3-ketoacyl-CoA thiolase. *EMBO (European Molecular Biology Organization)Journal* 10(11):3255-3262.
127. Rusch S L & Kendall D A (1995) Protein transport via amino-terminal targeting sequences: Common themes in diverse systems. *Molecular Membrane Biology* 12(4):295-307.
128. Soll J & Tien R (1998) Protein translocation into and across the chloroplastic envelope membranes. *Plant Molecular Biology* 38:191-207.
129. Gould S J, Keller G A, & Subramani S (1988) Identification of peroxisomal targeting signals located at the carboxy terminus of four peroxisomal proteins. *Journal of Cell Biology* 107(3):897-905.
130. Gould S J, Keller G A, Hosken N, Wilkinson J, & Subramani S (1989) A conserved tripeptide sorts proteins to peroxisomes. *Journal of Cell Biology* 108(5):1657-1664.
131. McCammon M T, McNew J A, Willy P J, & Goodman J M (1994) An internal region of the peroxisomal membrane protein PMP47 is essential for sorting to peroxisomes. *Journal of Cell Biology* 124(6):915-925.
132. Cokol M, Nair R, & Rost B (2000) Finding nuclear localization signals. *EMBO Reports* 1(5):411-415.
133. Helenius A & Aebi M (2001) Intracellular functions of N-linked glycans. *Science* 291(5512):2364-2369.
134. Emanuelsson O, Brunak S, von Heijne G, & Nielsen H (2007) Locating proteins in the cell using TargetP, SignalP and related tools. *Nature Protocols* 2(4):953-971.
135. Emanuelsson O, Nielsen H, Brunak S, & von Heijne G (2000) Predicting subcellular localization of proteins based on their N-terminal amino acid sequence. *Journal of Molecular Biology* 300(4):1005-1016.
136. Bannai H, Tamada Y, Maruyama O, Nakai K, & Miyano S (2002) Extensive feature detection of N-terminal protein sorting signals. *Bioinformatics* 18(2):298-305.
137. Bendtsen J D, Nielsen H, von Heijne G, & Brunak S (2004) Improved prediction of signal peptides: SignalP 3.0. *Journal of Molecular Biology* 340(4):783-795.
138. Hiller K, Grote A, Scheer M, Munch R, & Jahn D (2004) PrediSi: prediction of signal peptides and their cleavage positions. *Nucleic Acids Research* 32(Web Server issue):W375-379.
139. Bhasin M & Raghava G P (2004) ESLpred: SVM-based method for subcellular localization of eukaryotic proteins using dipeptide composition and PSI-BLAST. *Nucleic Acids Research* 32(Web Server issue):W414-419.
140. Garg A, Bhasin M, & Raghava G P (2005) Support vector machine-based method for subcellular localization of human proteins using amino acid compositions, their order, and similarity search. *Journal of Biological Chemistry* 280(15):14427-14432.
141. Bhasin M, Garg A, & Raghava G P (2005) PSLpred: prediction of subcellular localization of bacterial proteins. *Bioinformatics* 21(10):2522-2524.
142. Hoglund A, Donnes P, Blum T, Adolph H W, & Kohlbacher 0 (2006) MultiLoc: prediction of protein subcellular localization using N-terminal targeting sequences, sequence motifs and amino acid composition. *Bioinformatics* 22(10):1158-1165.
143. Shatkay H, et al. (2007) SherLoc: high-accuracy prediction of protein subcellular localization by integrating text and protein sequence data. *Bioinformatics* 23(11):1410-1417.
144. Emanuelsson O, Nielsen H, & von Heijne G (1999) ChloroP, a neural network-based method for predicting chloroplast transit peptides and their cleavage sites. *Protein Science* 8(5):978-984.
145. Claros M G & Vincens P (1996) Computational method to predict mitochondrially imported proteins and their targeting sequences. *European Journal of Biochemistry* 241(3):779-786.
146. Small I, Peeters N, Legeai F, & Lurin C (2004) Predotar: A tool for rapidly screening proteomes for N-terminal targeting sequences. *Proteomics* 4(6):1581-1590.
147. Kelley L A, MacCallum R M, & Sternberg M J (2000) Enhanced genome annotation using structural profiles in the program 3D-PSSM. *Journal of Molecular Biology* 299(2):499-520.
148. Shahin E A (1985) Totipotency of tomato protoplasts. *Theoretical and Applied Genetics* 69:235-240.
149. Fromm M, Taylor L P, & V. W (1985) Expression of genes transferred into monocot and dicot plant cells by electroporation. *Proceedings of the National Academy of Sciences of the United States of America* 82:5824-5828.
150. Fromm M E, Taylor L P, & Walbot V (1986) Stable transformation of maize after gene transfer by electroporation. *Nature* 319(6056):791-793.
151. Riggs C D & Bates G W (1986) Stable transformation of tobacco by electroporation: evidence for plasmid concatenation. *Proceedings of the National Academy of Sciences of the United States of America* 83(15):5602-5606.
152. D'Halluin K, Bonne E, Bossut M, De Beuckeleer M, & Leeman J (1992) Transgenic maize plants by tissue electroporation. *Plant Cell* 4:1495-1505.

153. Laursen C M, Krzyzek R A, Flick C E, Anderson P C, & Spencer T M (1994) Production of fertile transgenic maize by electroporation of suspension culture cells *Plant Molecular Biology* 24:51-61

154. Crossway A, et al. (1986) Integration of foreign DNA following microinjection of tobacco mesophyll protoplasts. *Molecular and General Genetics* 202:179-185.

155. Griesbach R J (1983) Protoplast microinjection. *Plant Molecular Biology Reporter* 1:32-37.

156. Sporlein B & Koop H-U (1991) Lipofectin: direct gene transfer to higher plants using cationic liposomes. *Theoretical and Applied Genetics* 83:1-5.

157. Ohgawara T, Uchimiya H, & Harada H (1983) Uptake of liposome-encapsulated plasmid DNA by plant protoplasts and molecular fate of foreign DNA *Protoplasma* 116:145-148.

158. Deshayes A, Herrera-Estrella L, & Caboche M (1985) Liposome-mediated transformation of tobacco mesophyll protoplasts by an *Escherichia coli* plasmid. *EMBO (European Molecular Biology Organization) Journal* 4(11): 2731-2737.

159. Christou P, Murphy J E, & Swain W F (1987) Stable transformation of soybean by electroporation and root formation from transformed callus. *Proceedings of the National Academy of Sciences of the United States of America* 84(12):3962-3966.

160. Horsch R B, et al. (1985) A Simple and General Method for Transferring Genes into Plants. *Science* 227:1229-1231.

161. Paszkowski J, et al. (1984) Direct gene transfer to plants. *Embo J* 3(12):2717-2722.

162. Hooykaas-Van Slogteren G M, Hooykaas P J, & Schilperoort R A (1984) Expression of Ti plasmid genes in monocotyledonous plants infected with *Agrobacterium tumefaciens*. *Nature* 311:763-764.

163. Rogers S G, Horsch, R. B., and Fraley, R. $T_m$ 1986. Gene transfer in plants: Production of transformed plants using Ti-plasmid vectors. (1986) Gene transfer in plants: Production of transformed plants using Ti-plasmid vectors. *Methods in Enzymology* 118:627-640.

164. Bevan M W & Chilton M-D (1982) T-DNA of the *Agrobacterium* Ti and Ri plasmids. *Annual Review of Genetics* 16:357-384.

165. Klein T M, et al. (1988) Transfer of foreign genes into intact maize cells with high-velocity microprojectiles. *Proceedings of the National Academy of Sciences of the United States of America* 85(12):4305-4309.

166. Klein T M, Gradziel T, Fromm M E, & Sanford J C (1988) Factors influencing gene delivery into *Zea mays* cells by high-velocity microprojectiles. *Biotechnology* 6:559-563.

167. McCabe D E, Swain W F, Martinell B J, & Christou P (1988) Stable transformation of soybean (*Glycine max*) by particle acceleration. *Biotechnology* 6:923-926.

168. Sanford J C, Smith F D, & Rushell J A (1993) Optimizing the biolistic process for different biological application. *The Methods in Enzymology*, ed Wu R (Academic Press, Orlando), Vol 217, pp 483-509.

169. Freeman J P, et al. (1984) A Comparison of Methods for Plasmid Delivery into Plant Protoplasts. *Plant and Cell Physiology* 25:1353-1365.

170. Frame B R, et al. (1994) Production of fertile transgenic maize plants by silicon carbide whisker-mediated transformation. *Plant Journal* 6:941-948.

171. Thompson J A, Drayton P, Frame B, Wang K, & Dunwell J M (1995) Maize transformation utilizing silicon carbide whiskers: a review. *Euphytica* 85:75-80.

172. Guo Y, Liang H, & Berns M W (1995) Laser-mediated gene transfer in rice. *Physiologia Plantarum* 93:19-24.

173. Badr Y A, Kereim M A, Yehia M A, Fouad 00, & Bahieldin A (2005) Production of fertile transgenic wheat plants by laser micropuncture. *Photochemical &Photobiological Sciences* 4:803-807.

174. Bao S, Thrall B D, & Miller D L (1997) Transfection of a reporter plasmid into cultured cells by sonoporation in vitro. *Ultrasound in Medicine and Biology* 23:953-959.

175. Finer K R & Finer J J (2000) Use of *Agrobacterium* expressing green fluorescent protein to evaluate colonization of sonication-assisted *Agrobacterium*-mediated transformation-treated soybean cotyledons. *Letters in Applied Microbiology* 30(5):406-410.

176. Amoah B K, Wu H, Sparks C, & Jones R D (2001) Factors influencing *Agrobacterium*-mediated transient expression of uidA in wheat inflorescence tissue. *Journal of Experimental Botany* 52(358): 1135-1142.

177. Krens F A, Molendijk L, Wullems G J, & Schilperoort R A (1982) In Vitro transformation of plant protoplasts with Ti-plasmid DNA. *Nature* 296:72-74.

178. Bechtold N & Pelletier G (1998) In planta *Agrobacterium*-mediated transformation of adult *Arabidopsis thaliana* plants by vacuum infiltration. *Methods in Molecular Biology* 82:259-266.

179. Broothaerts W, et al. (2005) Gene transfer to plants by diverse species of bacteria. *Nature* 433:629-633.

180. Urnov F D, Rebar E J, Holmes M C, Zhang H S, & Gregory P D (2010) Genome editing with engineered zinc finger nucleases. *Nature reviews. Genetics* 11(9):636-646.

181. Weinthal D, Tovkach A, Zeevi V, & Tzfira T (2010) Genome editing in plant cells by zinc finger nucleases. *Trends Plant Sci* 15(6):308-321.

182. Gaj T, Gersbach C A, & Barbas C F (2013) ZFN, TALEN and CRISPR/Cas-based methods for genome engineering. *Trends in biotechnology* 31(7):397-405.

183. Sprink T, Metje J, & Hartung F (2015) Plant genome editing by novel tools: TALEN and other sequence specific nucleases. *Current Opinion in Biotechnology* 32:47-53.

184. Bortesi L & Fischer R (2015) The CRISPR/Cas9 system for plant genome editing and beyond. *Biotechnology Advances* 33(1):41-52.

185. Kumar V & Jain M (2015) The CRISPR-Cas system for plant genome editing: advances and opportunities. *J Exp Bot* 66(1):47-57.

186. Kirk R E & Othmer D F (1993) Concise Encyclopedia of Chemical Technology (John Wiley & Sons) 4th Ed pp 433-514

187. Mosbach K, Birnbaum S, Hardy K, Davies J, & Billow L (1983) *Formation of proinsulin by immobilized Bacillus subtilis*. Nature 302:543-545.

188. Demain A L (2007) Reviews: The business of biotechnology. *Industrial Biotechnology* 3:269-283.

189. Chan H W & Wells R D (1974) Structural uniqueness of lactose operator. *Nature* 252:205-209.

190. Goeddel D V, et al. (1980) Synthesis of human fibroblast interferon by *E. coli Nucleic Acids Research* 8:4057-4074.

191. Marx C J & Lidstrom M E (2001) Development of improved versatile broad-host-range vectors for use in methylotrophs and other Gram-negative bacteria. *Microbiology* 147:2065-2075.

192. Atomi H, Imanaka T, & Fukui T (2012) Overview of the genetic tools in the Archaea. *Frontiers in microbiology* 3:337.

193. Farkas J A, Picking J W, & Santangelo T J (2013) Genetic techniques for the archaea. *Annu Rev Genet* 47:539-561.
194. Rehnstam-Holm A-S & Godhe A (2003) Genetic engineering of algal species. *Biotechnology*, ed Doelle H W (UNESCO, Eolss Publishers, Oxford, U K).
195. Rosa L, Galván-Cejudo A, & Fernandez E eds (2007) *Transgenic Microalgae as Green Cell Factories* (Springer Science+Business Media, LLC, New York, N.Y.), Vol 616.
196. Leon R & Fernandez E (2007) Nuclear transformation of eukaryotic microalgae: historical overview, achievements and problems. *Adv Exp Med Biol* 616:1-11.
197. Mikami K, Hirata R, Takahashi M, Uji T, & Saga N (2011) Transient Transformation of Red Algal Cells: Breakthrough Toward Genetic Transformation of Marine Crop *Porphyra* Species. *Genetic Transformation*, ed Alvarez M (InTech).
198. Umen J G & Olson B J (2012) Genomics of Volvocine Algae. *Advances in botanical research* 64:185-243.
199. Liu I, et al. (2013) Development of a new method for genetic transformation of the green alga *Chlorella ellipsoidea*. *Molecular biotechnology* 54(2):211-219.
200. Gimpel J A, Specht E A, Georgianna D R, & Mayfield S P (2013) Advances in microalgae engineering and synthetic biology applications for biofuel production. *Current opinion in chemical biology* 17(3):489-495.
201. Rasala B A, Chao S-S, Pier M, Barrera D J, & Mayfield S P (2014) Enhanced genetic tools for engineering multigene traits into green algae. *PLoS ONE*.
202. Sherman F (1991) Getting started with yeast. *Methods in Enzymology, Guide to Yeast Genetics and Molecular Biology*, eds Guthrie C & Fink G R (Acad. Press, New York), Vol 194, pp 3-21.
203. Sherman F, Fink G R, & Hick J B (1982) *Methods in Yeast Genetics* (Cold Spring Harbor Laboratory, New York).
204. Olmedo-Monfil V, CortEs-Penagos C, & Herrera-Estrella A (2004) Three Decades of Fungal Transformation), Vol 267, pp 297-313.
205. Weld R I, Plummer K M, Carpenter M A, & Ridgway H J (2006) Approaches to functional genomics in filamentous fungi. *Cell Res* 16(1):31-44.
206. Kawai S, Hashimoto W, & Murata K (2010) Transformation of *Saccharomyces cerevisiae* and other fungi: Methods and possible underlying mechanism. *Bioengineered Bugs* 1(6):395-403.
207. van den Berg M A & Maruthachalam K eds (2015) *Genetic Transformation Systems in Fungi*, Volume 1 (Springer, New York, N.Y.).
208. Rivera A L, Magana-Ortiz D, Gomez-Lim M, Fernandez F, & Loske A M (2014) Physical methods for genetic transformation of fungi and yeast. *Physics of life reviews* 11(2):184-203.
209. van Oers M M, Pijlman G P, & Vlak J M (2015) Thirty years of baculovirus-insect cell protein expression: from dark horse to mainstream technology. *Journal of General Virology* 96(1):6-23.
210. Almo S C & Love J D (2014) Better and faster: improvements and optimization for mammalian recombinant protein production. *Current Opinion in Structural Biology* 26:39-43.
211. Andersen L, Sundman L-O, Inge-Britt Linden I-B, Kontro P, & Simo S O (1984) Synthesis and anticonvulsant properties of some 2-Aminoethanesulfonic acid (Taurine) derivatives. *Journal of Pharmaceutical Sciences* 73:106-108.
212. Herdeis C & Weis C E (1999) 5889183.
213. Tserng K-Y, Hachey D L, & Klein P D (1977) An improved procedure for the synthesis of glycine and taurine conjugates of bile acids. *Journal of Lipid Research* 18:404-407.
214. Fong D W & Hoots J E (1992) 5128419.
215. Seeberger S, Griffin R I, Hardcastle I R, & Golding B T (2007) A new strategy for the synthesis of taurine derivatives using the 'safety-catch' principle for the protection of sulfonic acids. *Organic and Biomolecular Chemistry* 5:132-138.
216. Suzuki M, Nakajima Y, Sato T, Shirai H, & Hanabusa K (2006) Fabrication of $TiO_2$ using L-lysine-based organogelators as organic templates: control of the nanostructures. *Chemical Communications* (4):377-379.
217. Mikhalenko S A, Soloveva L I, & Lukyanets E A (2004) Phthalocyanines and related compounds: XXXVIII. Synthesis of symmetric taurine- and choline-substituted phthalocyanines. *Russian Journal of General Chemistry* 74:1775-1800.
218. Capone R, Blake S, Restrepo M R, Yang J, & Mayer M (2007) Designing Nanosensors Based on Charged Derivatives of Gramicidin A. *Journal of the American Chemical Society* 129:9737-9745.
219. Gupta R C, Win T, & Bittner S (2005) Taurine analogues; A new class of therapeutics: Retrospect and prospects *Current Medicinal Chemistry* 12:2021-2039.
220. Johnson B A (2008) Update on neuropharmacological treatments for alcoholism: Scientific basis and clinical findings. *Biochemical Pharmacology* 75:34-56.
221. Tambour S & Quertemont E (2007) Preclinical and clinical pharmacology of alcohol dependence. *Fundamental and Clinical Pharmacology* 21:9-28.
222. Joung Y K, Sengoku Y, Ooya T, Park K D, & Yui N (2005) Anticoagulant supramolecular-structured polymers: Synthesis and anticoagulant activity of taurine-conjugated carboxyethylester-polyrotaxanes. *Science and Technology of Advanced Materials* 6:484-490.
223. Ozmerig N, et al. (2000) Chitosan film enriched with an antioxidant agent, taurine, in fenestration defects. *Journal of Biomedical Materials Research Part A* 51:500-503.
224. Degim Z, et al. (2002) An investigation on skin wound healing in mice with a taurinechitosan gel formulation. *Amino Acids* 22:187-198.
225. Matsusaki M, Serizawa T, Kishida A, Endo T, & Akashi M (2002) Novel functional biodegradable polymer: Synthesis and anticoagulant activity of poly(γ-Glutamic Acid) sulfonate (γ-PGA-sulfonate). *Bioconjugate Chemistry* 13:23-28.
226. Roubos J A, van Staten G, & van Boxtel A J B (1999) An evolutionary strategy for fed-batch bioreactor optimization; concepts and performance. *Journal of biotechnology* 67(2-3):173-187.
227. Oka T (1999) Amino acids, production processes. *Encyclopedia of Bioprocess Technology: Fermentation, Biocatalysis, and Bioseparation*, eds Flickinger M C & Drew S W (Wiley, London).
228. Borowitzka M A (1999) Commercial production of microalgae: ponds, tanks, tubes and fermenters. *Journal of biotechnology* 70(1-3):313-321.
229. Hermann T (2003) Industrial production of amino acids by coryneform bacteria. *J Biotechnol* 104(1-3): 155-172.
230. Ikeda M (2003) Amino acid production processes. *Advances in biochemical engineering/biotechnology* 79:1-35.

231. Richmond A & Hu Q eds (2013) *Handbook of Microalgal Culture: Biotechnology and Applied Phycology* (Wiley-Blackwell, Hoboken, N.J.), 2nd Ed.
232. Ikeda M (2005) Towards bacterial strains overproducing 1-tryptophan and other aromatics by metabolic engineering. *Appl Microbiol Biotechnol* 69(6):615-626.
233. Cardozo K H, et al. (2007) Metabolites from algae with economical impact. *Comparative biochemistry and physiology. Toxicology &pharmacology: CBP* 146(1-2):60-78.
234. Demain A L (2007) The business of biotechnology. *Industrial Biotechnology* 3:269-283.
235. Milledge J J (2011) Commercial application of microalgae other than as biofuels: a brief review. *Reviews in Environmental Science and Biotechnology* 10:31-41.
236. Xu Q, Li S, Huang H, & Wen J (2012) Key technologies for the industrial production of fumaric acid by fermentation. *Biotechnology advances* 30(6):1685-1696.
237. Dufossé L, Fouillaud M, Caro Y, Mapari S A S, & Sutthiwong N (2014) Filamentous fungi are large-scale producers of pigments and colorants for the food industry. *Current Opinion in Biotechnology* 26:56-61.
238. Höfler A, et al. (1998) U.S. Pat. No. 5,840,358
239. Lee I, Lee K, Namgoong K, & Lee Y-S (2002) The use of ion exclusion chromatography as approved to the normal ion exchange chromatography to achieve a more efficient lysine recovery from fermentation broth. *Enzyme and Microbial Technology* 30(6):798-803.
240. Binder M & Uffinann K-E (2002) U.S. Pat. No. 6,465,025.
241. Hermann T (2003) Industrial production of amino acids by coryneform bacteria. *Journal of biotechnology* 104(1-3): 155-172.
242. Leuchtenberger W, Huthmacher K, & Drauz K (2005) Biotechnological production of amino acids and derivatives: current status and prospects. *Appl Microbiol Biotechnol* 69(1):1-8.
243. Meinkoth J & G. W (1984) Hybridization of nucleic acids immobilized on solid supports. *Analytical Biochemistry* 138:267-284.
244. Tijssen P (1993) Overview of principles of hybridization and the strategy of nucleic acid probe assays. *Laboratory Techniques in Biochemistry and Molecular Biology—Hybridization with Nucleic Acid Probes: Part I*, (Elsevier, New York).
245. Smith T F & Waterman M S (1981) Comparison of biosequences. *Advances in Applied Mathematics* 2:482-489.
246. Needleman S B & Wunsch C D (1970) A general method applicable to the search for similarities in the amino acid sequence of two proteins. *Journal of Molecular Biology* 48:443-453.
247. Pearson W R & Lipman D J (1988) Improved tools for biological sequence comparison. *Proceedings of the National Academy of Sciences of the United States of America* 85:2114-2448.
248. Higgins D G & Sharp P M (1989) Fast and sensitive multiple sequence alignments on a microcomputer. *Computer Applications in the Biosciences* 5(2):151-153.
249. Higgins D G, Bleasby A J, & Fuchs R (1992) CLUSTAL V: improved software for multiple sequence alignment. *Computer Applications in the Biosciences* 8(2):189-191.
250. Higgins D G & Sharp P M (1988) CLUSTAL: a package for performing multiple sequence alignment on a microcomputer. *Gene* 73(1):237-244.
251. Feng D F & Doolittle R F (1987) Progressive sequence alignment as a prerequisite to correct phylogenetic trees. *Journal of Molecular Evolution* 25(4):351-360.
252. Henikoff S & Henikoff J (1989) Amino acid substitution matrices from protein blocks Proceedings of the National Academy of Sciences of the United States of America 89:10915-10919.
253. Altschul S F, et al. (1997) Gapped BLAST and PSI-BLAST: a new generation of protein database search programs. *Nucleic Acids Research* 25:3389-3402.
254. Wootton J C & Federhen S (1993) Statistics of local complexity in amino acid sequences and sequence databases. *Computational Chemistry* 17:149-163.
255. Wootton J C & Federhen S (1996) Analysis of compositionally biased regions in sequence databases. *Methods Enzymol* 266:554-571.
256. Claverie J-M & States D J (1993) Information enhancement methods for large scale sequence analysis. *Computational Chemistry* 17:191-201.
257. Myers E W & Miller W (1988) Optimal alignments in linear-space. *Computer Applications in the Biological Sciences* 4:11-17.

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

Example 1

Development of a Transgenic Plant that Constitutively Expresses CDOL with the Native Transit Peptide and Constitutively Expresses SADL with the Native Transit Peptide in Tandem with Independent Promoters Step 1: Use chemical synthesis to make a DNA construct that contains a constitutive promoter, 35S, fused with the nucleotide sequence for CDOL gene (SEQ ID NO:1, SEQ ID NO:2, SEQ ID NO:3, or SEQ ID NO:4) and a NOS terminator. Clone the DNA construct into a binary vector, such as pCambia1300, pCambia2300, or pCambia3200.

The CDOL gene is as follows:
a. Derived from SEQ ID NO:1, optimized for expression in *Arabidopsis* or soybean (dicots) or corn (a monocot), and encoding a CDOL peptide from *Chlamydomonas reinhardtii* (SEQ ID NO:5); or
b. Derived from SEQ ID NO:2, optimized for expression in *Arabidopsis* or soybean (dicots) or corn (a monocot), and encoding a CDOL peptide from Guillardia theta (SEQ ID NO:6); or
c. Derived from SEQ ID NO:3, optimized for expression in *Arabidopsis* or soybean (dicots) or corn (a monocot), and encoding a CDOL peptide from Candida tenuis (SEQ ID NO:7); or
d. Derived from SEQ ID NO:4, optimized for expression in *Arabidopsis* or soybean (dicots) or corn (a monocot), and encoding a CDOL peptide from Fragilariopsis cylindrus (SEQ ID NO:8).

Step 2: Use chemical synthesis to make a DNA construct that contains a constitutive promoter, 35S, fused with the nucleotide sequence for SADL (SEQ ID NO:11, SEQ ID NO:12, SEQ ID NO:13, or SEQ ID NO:14) and a NOS terminator. Clone the SADL DNA construct into a binary vector that contains the CDOL DNA construct (Step 1).

The SADL gene is as follows:
a. Derived from SEQ ID NO:11 optimized for expression in *Arabidopsis* or soybean (dicots) or corn (a monocot), and encoding a SADL peptide from Guillardia theta (SEQ ID NO:17); or
b. Derived from SEQ ID NO:12, optimized for expression in *Arabidopsis* or soybean (dicots) or corn (a monocot), and encoding a SADL peptide from *Candida tenuis* (SEQ ID NO:18); or
c. Derived from SEQ ID NO:13 optimized for expression in *Arabidopsis* or soybean (dicots) or corn (a monocot), and encoding a SADL peptide from Cyanidioschyzon merolae (SEQ ID NO:19); or
d. Derived from SEQ ID NO:14, optimized for expression in *Arabidopsis* or soybean (dicots) or corn (a monocot), and encoding a SADL peptide from *Thalassiosira oceanica* (SEQ ID NO:20).

Step 3: Transform the DNA construct into *Agrobacterium tumefaciens*, select for antibiotic resistance, and confirm the presence of the DNA construct.

Step 4: Transform plant (*Arabidopsis*, soybean, corn, wheat, sugar beet, rice, camelina or canola), select for antibiotic resistance, and confirm the presence of the DNA constructs in the transgenic plant.

Example 2

Development of a Transgenic Plant that Constitutively Expresses CDOL with a Plant Plastid Transit Peptide and Constitutively Expresses SADL Protein with a Plant Plastid Transit Peptide in Tandem with Independent Promoters Step 1: Use chemical synthesis to make a DNA construct that contains a constitutive promoter, 35S, fused with the nucleotide sequence for a plastid transit peptide (SEQ ID NO:21), truncated CDOL gene (SEQ ID NO:1, SEQ ID NO:2, SEQ ID NO:3, or SEQ ID NO:4) and a NOS terminator. Clone the DNA construct into a binary vector, such as pCambia1300, pCambia2300, or pCambia3200.

The nucleotide sequence for the plastid transit peptide (SEQ ID NO:21) encodes the peptide SEQ ID NO:22.

The CDOL gene is as follows:
a. Derived from SEQ ID NO:1 by removing nucleotides 1 through 159 (corresponding to the native transit peptide), optimized for expression in *Arabidopsis* or soybean (dicots) or corn (a monocot), and encoding a CDOL peptide from *Chlamydomonas reinhardtii* (SEQ ID NO:5 minus amino acids 1 through 53); or
b. Derived from SEQ ID NO:2 by removing nucleotides 1 through 279 (corresponding to the native transit peptide), optimized for expression in *Arabidopsis* or soybean (dicots) or corn (a monocot), and encoding a CDOL peptide from Guillardia *theta* (SEQ ID NO:6 minus amino acids 1 through 93); or
c. Derived from SEQ ID NO:3 by removing nucleotides 1 through 126 (corresponding to the native transit peptide), optimized for expression in *Arabidopsis* or soybean (dicots) or corn (a monocot), and encoding a CDOL peptide from *Candida tenuis* (SEQ ID NO:7 minus amino acids 1 through 42); or
d. Derived from SEQ ID NO:4 by removing nucleotides 1 through 180 (corresponding to the native transit peptide), optimized for expression in *Arabidopsis* or soybean (dicots) or corn (a monocot), and encoding a CDOL peptide from *Fragilariopsis cylindrus* (SEQ ID NO:8 minus amino acids 1 through 60).

Step 2: Use chemical synthesis to make a DNA construct that contains a constitutive promoter, 35S, fused with the nucleotide sequence for a plastid transit peptide (SEQ ID NO: 21), truncated SADL (SEQ ID NO:11, SEQ ID NO:12, SEQ ID NO:13, or SEQ ID NO:14) and a NOS terminator. Clone the SADL DNA construct into a binary vector that contains the CDOL DNA construct (Step1).

The nucleotide sequence for the plastid transit peptide (SEQ ID NO: 21) encodes the peptide SEQ ID NO: 22. Clone the SADL DNA construct into a binary vector that contains the CDOL DNA construct (Step1).

The SADL gene is as follows:
a. Derived from SEQ ID NO:11, by removing nucleotides 1 through 54, (corresponding to the native transit peptide) optimized for expression in *Arabidopsis* or soybean (dicots) or corn (a monocot), and encoding a truncated SADL peptide from Guillardia theta (SEQ ID NO:17 minus amino acids 1 through 18); or
b. Derived from SEQ ID NO:12, by removing nucleotides 1 through 33 (corresponding to the native transit peptide), optimized for expression in *Arabidopsis* or soybean (dicots) or corn (a monocot), and encoding a truncated SADL peptide from *Candida tenuis* (SEQ ID NO:18 minus amino acids 1 through 11); or
c. Derived from SEQ ID NO:13, by removing nucleotides 1 through 12, (corresponding to the native transit peptide) optimized for expression in *Arabidopsis* or soybean (dicots) or corn (a monocot), and encoding a truncated SADL peptide from Cyanidioschyzon merolae (SEQ ID NO:19 minus amino acids 1 through 4); or
d. Derived from SEQ ID NO:14, by removing nucleotides 1 through 18 (corresponding to the native transit peptide), optimized for expression in *Arabidopsis* or soybean (dicots) or corn (a monocot), and encoding a truncated SADL peptide from *Thalassiosira* oceanica (SEQ ID NO:20 minus amino acids 1 through 6).

Step 3: Transform the DNA construct into *Agrobacterium tumefaciens*, select for antibiotic resistance, and confirm the presence of the DNA construct.

Step 4: Transform plant (*Arabidopsis*, soybean, corn, wheat, sugar beet, rice, camelina or canola), select for antibiotic resistance, and confirm the presence of the DNA constructs in the transgenic plant.

Example 3

Development of a Transgenic Plant that Constitutively Expresses CDOL with the Native Plastid Transit Peptide and Constitutively Expresses CS/PLP-DC with the Native Transit Peptide in Tandem with Independent Promotes Step 1: Use chemical synthesis to make a DNA construct that contains a constitutive promoter, 35S, fused with the nucleotide sequence for CDOL gene (SEQ ID NO:1, SEQ ID NO:2, SEQ ID NO:3, or SEQ ID NO:4) and a NOS terminator. Clone the DNA construct into a binary vector, such as pCambia1300, pCambia2300, or pCambia3200.

The CDOL gene is as follows:
a. Derived from SEQ ID NO:1, optimized for expression in *Arabidopsis* or soybean (dicots) or corn (a monocot), and encoding a CDOL peptide from *Chlamydomonas reinhardtii* (SEQ ID NO:5); or
b. Derived from SEQ ID NO:2, optimized for expression in *Arabidopsis* or soybean (dicots) or corn (a monocot), and encoding a CDOL peptide from Guillardia theta (SEQ ID NO:6); or c. Derived from SEQ ID NO:3, optimized for expression in *Arabidopsis* or soybean (dicots) or corn (a monocot), and encoding a CDOL peptide from *Candida tenuis* (SEQ ID NO:7); or
d. Derived from SEQ ID NO:4, optimized for expression in *Arabidopsis* or soybean (dicots) or corn (a monocot), and encoding a CDOL peptide from *Fragilariopsis cylindrus* (SEQ ID NO:8).

Step 2: Use chemical synthesis to make a DNA construct that contains a constitutive promoter, 35S, fused with the nucleotide sequence for CS/PLP-DC (SEQ ID NO:9 or SEQ ID NO:10) and a NOS terminator. Clone the CS/PLP-DC DNA construct into a binary vector that contains the CDOL DNA construct (Step1).

The CS/PLP-DC gene is as follows:
a. Derived from SEQ ID NO:9 optimized for expression in *Arabidopsis* or soybean (dicots) or corn (a monocot), and encoding CS/PLP-DC peptide from *Micromonas pusilla* (SEQ ID NO:15; or
b. Derived from SEQ ID NO:10, optimized for expression in *Arabidopsis* or soybean (dicots) or corn (a monocot), and encoding CS/PLP-DC peptide from *Ostreococcus tauri* (SEQ ID NO:16).

Step 3: Transform the DNA construct into *Agrobacterium tumefaciens*, select for antibiotic resistance, and confirm the presence of the DNA construct.

Step 4: Transform plant (*Arabidopsis*, soybean, corn, wheat, sugar beet, rice, camelina or canola), select for antibiotic resistance, and confirm the presence of the DNA constructs in the transgenic plant.

Example 4

Development of a Transgenic Plant that Constitutively Expresses CDOL with a Plant Plastid Transit Peptide and Constitutively Expresses CS/PLP-DC with a Plant Plastid Transit Peptide in Tandem with Independent Promoters Step 1: Use chemical synthesis to make a DNA construct that contains a constitutive promoter, 35S, fused with the nucleotide sequence for a plastid transit peptide (SEQ ID NO:21), truncated CDOL gene (SEQ ID NO:1, SEQ ID NO:2, SEQ ID NO:3, or SEQ ID NO:4) and a NOS terminator. Clone the DNA construct into a binary vector, such as pCambia1300, pCambia2300 or pCambia3200.

The nucleotide sequence for the plastid transit peptide (SEQ ID NO:21) encodes the peptide SEQ ID NO:22.

The CDOL gene is as follows:
a. Derived from SEQ ID NO:1 by removing nucleotides 1 through 159 (corresponding to the native transit peptide), optimized for expression in *Arabidopsis* or soybean (dicots) or corn (a monocot), and encoding a CDOL peptide from *Chlamydomonas reinhardtii* (SEQ ID NO:5 minus amino acids 1 through 53); or
b. Derived from SEQ ID NO:2 by removing nucleotides 1 through 279 (corresponding to the native transit peptide), optimized for expression in *Arabidopsis* or soybean (dicots) or corn (a monocot), and encoding a CDOL peptide from *Guillardia theta* (SEQ ID NO:6 minus amino acids 1 through 93); or
c. Derived from SEQ ID NO:3 by removing nucleotides 1 through 126 (corresponding to the native transit peptide), optimized for expression in *Arabidopsis* or soybean (dicots) or corn (a monocot), and encoding a CDOL peptide from *Candida tenuis* (SEQ ID NO:7 minus amino acids 1 through 42); or
d. Derived from SEQ ID NO:4 by removing nucleotides 1 through 180 (corresponding to the native transit peptide), optimized for expression in *Arabidopsis* or soybean (dicots) or corn (a monocot), and encoding a CDOL peptide from *Fragilariopsis cylindrus* (SEQ ID NO:8 minus amino acids 1 through 60).

Step 2: Use chemical synthesis to make a DNA construct that contains a constitutive promoter, 35S, fused with the nucleotide sequence for a plastid transit peptide (SEQ ID NO: 21), CS/PLP-DC (SEQ ID NO:9 or SEQ ID NO:10) and a NOS terminator. The nucleotide sequence for the plastid transit peptide (SEQ ID NO: 21) encodes the peptide SEQ ID NO: 22. Clone the CS/PLP-DC DNA construct into a binary vector that contains the CDOL DNA construct (Step1).

The CS/PLP-DC gene is as follows:
a. Derived from SEQ ID NO:9, by removing nucleotides 1 through 234, (corresponding to the native transit peptide) optimized for expression in *Arabidopsis* or soybean (dicots) or corn (a monocot), and encoding a CS/PLP-DC peptide from *Micromonas pusilla* (SEQ ID NO:15 minus amino acids 1 through 78); or
b. Derived from SEQ ID NO:10, by removing nucleotides 1 through 69 (corresponding to the native transit peptide), optimized for expression in *Arabidopsis* or soybean (dicots) or corn (a monocot), and encoding a CS/PLP-DC peptide from *Ostreococcus tauri* (SEQ ID NO:16 minus amino acids 1 through 23).

Step 3: Transform the DNA construct into *Agrobacterium tumefaciens*, select for antibiotic resistance, and confirm the presence of the DNA construct.

Step 4: Transform plant (*Arabidopsis*, soybean, corn, wheat, sugar beet, rice, camelina or canola), select for antibiotic resistance, and confirm the presence of the DNA constructs in the transgenic plant.

Example 5

Development of a Transgenic Plant that Constitutively Expresses CDOL with the Native Plastid Transit Peptide and Constitutively Expresses partCS/PLP-DC with a Plant Plastid Transit Peptide in Tandem with Independent Promotes Step 1: Use chemical synthesis to make a DNA construct that contains a constitutive promoter, 35S, fused with the nucleotide sequence for CDOL gene (SEQ ID NO:1, SEQ ID NO:2, SEQ ID NO:3, or SEQ ID NO:4) and a NOS terminator. Clone the DNA construct into a binary vector, such as pCambia1300, pCambia2300, or pCambia3200.

The CDOL gene is as follows:
a. Derived from SEQ ID NO:1, optimized for expression in *Arabidopsis* or soybean (dicots) or corn (a monocot), and encoding a CDOL peptide from *Chlamydomonas reinhardtii* (SEQ ID NO:5); or
b. Derived from SEQ ID NO:2, optimized for expression in *Arabidopsis* or soybean (dicots) or corn (a monocot), and encoding a CDOL peptide from *Guillardia theta* (SEQ ID NO:6); or
c. Derived from SEQ ID NO:3, optimized for expression in *Arabidopsis* or soybean (dicots) or corn (a monocot), and encoding a CDOL peptide from *Candida tenuis* (SEQ ID NO:7); or
d. Derived from SEQ ID NO:4, optimized for expression in *Arabidopsis* or soybean (dicots) or corn (a monocot), and encoding a CDOL peptide from *Fragilariopsis cylindrus* (SEQ ID NO:8).

Step 2: Use chemical synthesis to make a DNA construct that contains a constitutive promoter, 35S, fused with the nucleotide sequence for a plastid transit peptide (SEQ ID NO: 21), CS/PLP-DC (SEQ ID NO:9 or SEQ ID NO:10) and a NOS terminator. The nucleotide sequence for the plastid transit peptide (SEQ ID NO: 21) encodes the peptide SEQ ID NO: 22. Clone the partCS/LP-DC DNA construct into a binary vector that contains the CDOL DNA construct (Step1).

The partCS/PLP-DC gene is as follows:
a. Derived from SEQ ID NO:9, by removing nucleotides 1 through 1413, (corresponding to the native transit and cysteine synthetase peptides) optimized for expression in *Arabidopsis* or soybean (dicots) or corn (a monocot), and encoding a partCS/PLP-DC peptide from Micromonas *pusilla* (SEQ ID NO:15 minus amino acids 1 through 471); or
b. Derived from SEQ ID NO:10, by removing nucleotides 1 through 1068 (corresponding to the native transit peptide and cysteine synthetase peptides), optimized for expression in *Arabidopsis* or soybean (dicots) or corn (a monocot), and encoding a partCS/PLP-DC peptide from Ostreococcus tauri (SEQ ID NO:16 minus amino acids 1 through 356).

Step 3: Transform the DNA construct into *Agrobacterium tumefaciens*, select for antibiotic resistance, and confirm the presence of the DNA construct.

Step 4: Transform plant (*Arabidopsis*, soybean, corn, wheat, sugar beet, rice, camelina or canola), select for antibiotic resistance, and confirm the presence of the DNA constructs in the transgenic plant.

Example 6

Development of a Transgenic Plant that Constitutively Expresses CDOL with a Plant Plastid Transit Peptide and Constitutively Expresses partCS/PLP-DC Protein with a Plant Plastid Transit Peptide in Tandem with Independent Promoters Step 1: Use chemical synthesis to make a DNA construct that contains a constitutive promoter, 35S, fused with the nucleotide sequence for a plastid transit peptide (SEQ ID NO:21), truncated CDOL gene (SEQ ID NO:1, or SEQ ID NO:2, SEQ ID NO:3 or SEQ ID NO:4) and a NOS terminator. Clone the DNA construct into a binary vector, such as pCambia1300, pCambia2300 or pCambia3200.

The nucleotide sequence for the plastid transit peptide (SEQ ID NO:21) encodes the peptide SEQ ID NO:22.

The CDOL gene is as follows:
a. Derived from SEQ ID NO:1 by removing nucleotides 1 through 159 (corresponding to the native transit peptide), optimized for expression in *Arabidopsis* or soybean (dicots) or corn (a monocot), and encoding a CDOL peptide from *Chlamydomonas reinhardtii* (SEQ ID NO:5 minus amino acids 1 through 53); or
b. Derived from SEQ ID NO:2 by removing nucleotides 1 through 279 (corresponding to the native transit peptide), optimized for expression in *Arabidopsis* or soybean (dicots) or corn (a monocot), and encoding a CDOL peptide from Guillardia theta (SEQ ID NO:6 minus amino acids 1 through 93); or
c. Derived from SEQ ID NO:3 by removing nucleotides 1 through 126 (corresponding to the native transit peptide), optimized for expression in *Arabidopsis* or soybean (dicots) or corn (a monocot), and encoding a CDOL peptide from *Candida tenuis* (SEQ ID NO:7 minus amino acids 1 through 42); or
d. Derived from SEQ ID NO:4 by removing nucleotides 1 through 180 (corresponding to the native transit peptide), optimized for expression in *Arabidopsis* or soybean (dicots) or corn (a monocot), and encoding a CDOL peptide from *Fragilariopsis cylindrus* (SEQ ID NO:8 minus amino acids 1 through 60).

Step 2: Use chemical synthesis to make a DNA construct that contains a constitutive promoter, 35S, fused with the nucleotide sequence for a plastid transit peptide (SEQ ID NO: 21), partCS/PLP-DC (SEQ ID NO:9 or SEQ ID NO:10) and a NOS terminator. The nucleotide sequence for the plastid transit peptide (SEQ ID NO: 21) encodes the peptide SEQ ID NO: 22. Clone the partCS/LP-DC DNA construct into a binary vector that contains the CDOL DNA construct (Step1).

The partCS/PLP-DC gene is as follows:
a. Derived from SEQ ID NO:9, by removing nucleotides 1 through 1413, (corresponding to the native transit and cysteine synthetase peptides) optimized for expression in *Arabidopsis* or soybean (dicots) or corn (a monocot), and encoding a partCS/PLP-DC peptide from Micromonas *pusilla* (SEQ ID NO:15 minus amino acids 1 through 471); or
b. Derived from SEQ ID NO:10 by removing nucleotides 1 through 1068 (corresponding to the native transit and cysteine synthetase peptides), optimized for expression in *Arabidopsis* or soybean (dicots) or corn (a monocot), and encoding a partCS/PLP-DC peptide from Ostreococcus tauri (SEQ ID NO:16 minus amino acids 1 through 356).

Step 3: Transform the DNA construct into *Agrobacterium tumefaciens*, select for antibiotic resistance, and confirm the presence of the DNA construct.

Step 4: Transform plant (*Arabidopsis*, soybean, corn, wheat, sugar beet, rice, camelina or canola), select for antibiotic resistance, and confirm the presence of the DNA constructs in the transgenic plant.

Example 8

Development of a Transgenic Plant that Constitutively Expresses CS/PLP-DC Protein with the Native Transit Peptide Step 1: Use chemical synthesis to make a DNA construct that contains a constitutive promoter, 35S, fused with the nucleotide sequence for CS/PLP-DC (SEQ ID NO:9 or SEQ ID NO:10) and a NOS terminator. Clone the DNA construct into a binary vector, such as pCambia1300, pCambia2300, or pCambia3200.

The CS/PLP-DC gene is as follows:
a. Derived from SEQ ID NO:9 optimized for expression in *Arabidopsis* or soybean (dicots) or corn (a monocot), and encoding CS/PLP-DC peptide from *Micromonas pusilla* (SEQ ID NO:15; or
b. Derived from SEQ ID NO:10, optimized for expression in *Arabidopsis* or soybean (dicots) or corn (a monocot), and encoding CS/PLP-DC peptide from Ostreococcus *tauri* (SEQ ID NO:16).

Step 2: Transform the DNA construct into *Agrobacterium tumefaciens*, select for antibiotic resistance, and confirm the presence of the DNA construct.

Step 4: Transform plant (*Arabidopsis*, soybean, corn, wheat, sugar beet, rice, camelina or canola), select for antibiotic resistance, and confirm the presence of the DNA constructs in the transgenic plant.

Example 8

Development of a Transgenic Plant that Constitutively CS/PLP-DC Protein with a Plant Plastid Transit Peptide Step 1: Use chemical synthesis to make a DNA construct that contains a constitutive promoter, 35S, fused with the nucleotide sequence for a plastid transit peptide (SEQ ID NO: 21), CS/PLP-DC (SEQ ID NO:9 or SEQ ID NO:10) and a NOS terminator. Clone the DNA construct into a binary vector, such as pCambia1300, pCambia2300, or pCambia3200.

The nucleotide sequence for the plastid transit peptide (SEQ ID NO:21) encodes the peptide SEQ ID NO:22.

The CS/PLP-DC gene is as follows:
a. Derived from SEQ ID NO:9, by removing nucleotides 1 through 234, (corresponding to the native transit peptide) optimized for expression in *Arabidopsis* or soybean (dicots) or corn (a monocot), and encoding a CS/PLP-DC peptide from *Micromonas pusilla* (SEQ ID NO:15 minus amino acids 1 through 78); or
b. Derived from SEQ ID NO:10, by removing nucleotides 1 through 69 (corresponding to the native transit peptide), optimized for expression in *Arabidopsis* or soybean (dicots) or corn (a monocot), and encoding a CS/PLP-DC peptide from Ostreococcus *tauri* (SEQ ID NO:16 minus amino acids 1 through 23).

Step 2: Transform the DNA construct into *Agrobacterium tumefaciens*, select for antibiotic resistance, and confirm the presence of the DNA construct.

Step 3: Transform plant (*Arabidopsis*, soybean, corn, wheat, sugar beet, rice, camelina or canola), select for antibiotic resistance, and confirm the presence of the DNA constructs in the transgenic plant.

Example 9

Development of a Transgenic Plant that Constitutively Expresses CDOL with the Native Transit Peptide Fused (without a Linker) to a SADL Using Chemical Synthesis Step 1: Use chemical synthesis to make a DNA construct that contains a constitutive promoter, 35S, fused with nucleotide sequence for a CDOL gene (SEQ ID NO:1, SEQ ID NO:2, SEQ ID NO:3, or SEQ ID NO:4), and SADL gene (SEQ ID NO:11, SEQ ID NO:12, SEQ ID NO:13, or SEQ ID NO:14) all in-frame and a NOS terminator. Clone the DNA construct into a binary vector, such as pCambia1300, pCambia2300 or pCambia3200.

The CDOL gene is as follows:
a. Derived from SEQ ID NO:1, without the stop codon, optimized for expression in *Arabidopsis* or soybean (dicots) or corn (a monocot), and encoding a CDOL peptide from *Chlamydomonas reinhardtii* (SEQ ID NO:5); or
b. Derived from SEQ ID NO:2, without the stop codon, optimized for expression in *Arabidopsis* or soybean (dicots) or corn (a monocot), and encoding a CDOL peptide from *Guillardia theta* (SEQ ID NO:6); or
c. Derived from SEQ ID NO:3, without the stop codon, optimized for expression in *Arabidopsis* or soybean (dicots) or corn (a monocot), and encoding a CDOL peptide from *Candida tenuis* (SEQ ID NO:7); or
d. Derived from SEQ ID NO:4, without the stop codon, optimized for expression in *Arabidopsis* or soybean (dicots) or corn (a monocot), and encoding a CDOL peptide from *Fragilariopsis cylindrus* (SEQ ID NO:8).

The SADL gene is as follows:
a. Derived from SEQ ID NO:11 by removing nucleotides 1 through 54, (corresponding to the native transit peptide) optimized for expression in *Arabidopsis* or soybean (dicots) or corn (a monocot), and encoding a truncated SADL peptide from Guillardia *theta* (SEQ ID NO:17 minus amino acids 1 through 18); or
b. Derived from SEQ ID NO:12 by removing nucleotides 1 through 33 (corresponding to a putative transit peptide), optimized for expression in *Arabidopsis* or soybean (dicots) or corn (a monocot), and encoding a truncated SADL peptide from *Candida tenuis* (SEQ ID NO:18 minus amino acids 1 through 11); or
c. Derived from SEQ ID NO:13 by removing nucleotides 1 through 12, (corresponding to the native transit peptide) optimized for expression in *Arabidopsis* or soybean (dicots) or corn (a monocot), and encoding a truncated SADL peptide from Cyanidioschyzon *merolae* (SEQ ID NO:19 minus amino acids 1 through 4); or
d. Derived from SEQ ID NO:14 by removing nucleotides 1 through 18 (corresponding to the native transit peptide), optimized for expression in *Arabidopsis* or soybean (dicots) or corn (a monocot), and encoding a truncated SADL peptide from *Thalassiosira oceanica* (SEQ ID NO:20 minus amino acids 1 through 6).

Step 2: Transform the DNA construct into *Agrobacterium tumefaciens*, select for antibiotic resistance, and confirm the presence of the DNA construct.

Step 3: Transform plant (*Arabidopsis*, soybean, corn, wheat, sugar beet, rice, camelina or canola), select for antibiotic resistance, and confirm the presence of the DNA constructs in the transgenic plant.

Example 10

Development of a Transgenic Plant that Constitutively Expresses CDOL without Transit Peptide Fused with a Linker to partCS/PLP-DC Using Chemical Synthesis Step 1: Use chemical synthesis to make a DNA construct that contains a constitutive promoter, 35S, fused with nucleotide sequence of a CDOL gene (SEQ ID NO:1, SEQ ID NO:2, SEQ ID NO:3, or SEQ ID NO:4) without the transit peptide, linker (SEQ ID NO:23), SADL gene (SEQ ID NO:11, SEQ ID NO:12, SEQ ID NO:13, or SEQ ID NO:14) without the transit peptide all in-frame and a NOS terminator. Clone the DNA construct into a binary vector, such as pCambia1300, pCambia2300 or pCambia3200.

The CDOL gene is as follows:
a. Derived from SEQ ID NO:1 by removing nucleotides 4 through 159 (corresponding to the native transit peptide) and without the stop codon, optimized for expression in *Arabidopsis* or soybean (dicots) or corn (a monocot), and encoding a CDOL peptide from *Chlamydomonas reinhardtii* (SEQ ID NO:5 minus amino acids 2 through 53); or
b. Derived from SEQ ID NO:2 by removing nucleotides 4 through 279 (corresponding to the native transit peptide) and without the stop codon, optimized for expression in *Arabidopsis* or soybean (dicots) or corn (a monocot), and encoding a CDOL peptide from *Guillardia theta* (SEQ ID NO:6 minus amino acids 2 through 93); or c. Derived from SEQ ID NO:3 by removing nucleotides 4 through 126 (corresponding to the native transit peptide) and without the stop codon, optimized for expression in *Arabidopsis* or soybean (dicots) or corn (a monocot), and encoding a CDOL peptide from *Candida tenuis* (SEQ ID NO:7 minus amino acids 2 through 42); or d. Derived from SEQ ID NO:4 by removing nucleotides 4 through 180 (corresponding to the native transit peptide) and without the stop codon, optimized for expression in *Arabidopsis* or soybean (dicots) or corn (a monocot), and encoding a CDOL peptide from *Fragilariopsis cylindrus* (SEQ ID NO:8 minus amino acids 2 through 60).

The partCS/PLP-DC gene is as follows:

a. Derived from SEQ ID NO:9 by removing nucleotides 1 through 1413 (corresponding to the native transit and cysteine synthetase peptides), optimized for expression in *Arabidopsis* or soybean (dicots) or corn (a monocot), and encoding a partCS/PLP-DC peptide from *Micromonas pusilla* (SEQ ID NO:15 minus amino acids 1 through 471); or b. Derived from SEQ ID NO:10 truncated by removing nucleotides 1 through 1068 (corresponding to the native transit and cysteine synthetase peptides), optimized for expression in *Arabidopsis* or soybean (dicots) or corn (a monocot), and encoding a partCS/PLP-DC peptide from Ostreococcus *tauri* (SEQ ID NO:16 minus amino acids 1 through 356).

Step 2: Transform the DNA construct into *Agrobacterium tumefaciens*, select for antibiotic resistance, and confirm the presence of the DNA construct.

Step 3: Transform plant (*Arabidopsis*, soybean, corn, wheat, sugar beet, rice, camelina or canola), select for antibiotic resistance, and confirm the presence of the DNA constructs in the transgenic plant.

Example 11

Development of a Transgenic Plant that Constitutively Expresses CDOL with a Plant Transit Peptide Fused with a Linker to SADL Using Chemical Synthesis Step 1: Use chemical synthesis to make a DNA construct that contains a constitutive promoter, 35S, fused with nucleotide sequence of a plastid transit peptide (SEQ ID NO:21), CDOL gene (SEQ ID NO:1, SEQ ID NO:2, SEQ ID NO:3, or SEQ ID NO:4), linker (SEQ ID NO:23), SADL gene (SEQ ID NO:11, SEQ ID NO:12, SEQ ID NO:13, or SEQ ID NO:14) all in-frame and a NOS terminator. Clone the DNA construct into a binary vector, such as pCambia1300, pCambia2300 or pCambia3200.

The nucleotide sequence for the plastid transit peptide (SEQ ID NO:21) encodes the peptide SEQ ID NO:22.

The CDOL gene is as follows:

a. Derived from SEQ ID NO:1 by removing nucleotides 1 through 159 (corresponding to the native transit peptide) and removing the stop codon, optimized for expression in *Arabidopsis* or soybean (dicots) or corn (a monocot), and encoding a CDOL peptide from *Chlamydomonas reinhardtii* (SEQ ID NO:5 minus amino acids 1 through 53); or b. Derived from SEQ ID NO:2 by removing nucleotides 1 through 279 (corresponding to the native transit peptide) and removing the stop codon, optimized for expression in *Arabidopsis* or soybean (dicots) or corn (a monocot), and encoding a CDOL peptide from *Guillardia theta* (SEQ ID NO:6 minus amino acids 1 through 93); or c. Derived from SEQ ID NO:3 by removing nucleotides 1 through 126 (corresponding to the native transit peptide) and removing the stop codon, optimized for expression in *Arabidopsis* or soybean (dicots) or corn (a monocot), and encoding a CDOL peptide from *Candida tenuis* (SEQ ID NO:7 minus amino acids 1 through 42); or d. Derived from SEQ ID NO:4 by removing nucleotides 1 through 180 (corresponding to the native transit peptide) and removing the stop codon, optimized for expression in *Arabidopsis* or soybean (dicots) or corn (a monocot), and encoding a CDOL peptide from *Fragilariopsis cylindrus* (SEQ ID NO:8 minus amino acids 1 through 60).

The SADL gene is as follows:

a. Derived from SEQ ID NO:11 by removing nucleotides 1 through 54, (corresponding to the native transit peptide) optimized for expression in *Arabidopsis* or soybean (dicots) or corn (a monocot), and encoding a truncated SADL peptide from Guillardia *theta* (SEQ ID NO:17 minus amino acids 1 through 18); or b. Derived from SEQ ID NO:12 by removing nucleotides 1 through 33 (corresponding to the native transit peptide), optimized for expression in *Arabidopsis* or soybean (dicots) or corn (a monocot), and encoding a truncated SADL peptide from *Candida tenuis* (SEQ ID NO:18 minus amino acids 1 through 11); or c. Derived from SEQ ID NO:13 by removing nucleotides 1 through 12, (corresponding to the native transit peptide) optimized for expression in *Arabidopsis* or soybean (dicots) or corn (a monocot), and encoding a truncated SADL peptide from Cyanidioschyzon merolae (SEQ ID NO:19 minus amino acids 1 through 4); or d. Derived from SEQ ID NO:14 by removing nucleotides 1 through 18 (corresponding to the native transit peptide), optimized for expression in *Arabidopsis* or soybean (dicots) or corn (a monocot), and encoding a truncated SADL peptide from *Thalassiosira oceanica* (SEQ ID NO:20 minus amino acids 1 through 6).

Step 2: Transform the DNA construct into *Agrobacterium tumefaciens*, select for antibiotic resistance, and confirm the presence of the DNA construct.

Step 3: Transform plant (*Arabidopsis*, soybean, corn, wheat, sugar beet, rice, camelina or canola), select for antibiotic resistance, and confirm the presence of the DNA constructs in the transgenic plant.

Example 12

Development of a Transgenic Plant that Constitutively Expresses CDOL without Transit Peptide Fused with a Linker to SADL Using Chemical Synthesis Step 1: Use chemical synthesis to make a DNA construct that contains a constitutive promoter, 35S, fused with nucleotide sequence of a CDOL gene (SEQ ID NO:1, SEQ ID NO:2, SEQ ID NO:3, or SEQ ID NO:4) without the transit peptide, linker (SEQ ID NO:23), SADL gene (SEQ ID NO:11, SEQ ID NO:12, SEQ ID NO:13, or SEQ ID NO:14) without the transit peptide, all in-frame and a NOS terminator. Clone the DNA construct into a binary vector, such as pCambia1300, pCambia2300 or pCambia3200.

The CDOL gene is as follows:
a. Derived from SEQ ID NO:1 by removing nucleotides 4 through 159 (corresponding to the native transit peptide) and without the stop codon, optimized for expression in *Arabidopsis* or soybean (dicots) or corn (a monocot), and encoding a CDOL peptide from *Chlamydomonas reinhardtii* (SEQ ID NO:5 minus amino acids 2 through 53); or
b. Derived from SEQ ID NO:2 by removing nucleotides 4 through 279 (corresponding to the native transit peptide) and without the stop codon, optimized for expression in *Arabidopsis* or soybean (dicots) or corn (a monocot), and encoding a CDOL peptide from Guillardia theta (SEQ ID NO:6 minus amino acids 2 through 93); or
c. Derived from SEQ ID NO:3 by removing nucleotides 4 through 126 (corresponding to the native transit peptide) and without the stop codon, optimized for expression in *Arabidopsis* or soybean (dicots) or corn (a monocot), and encoding a CDOL peptide from *Candida tenuis* (SEQ ID NO:7 minus amino acids 2 through 42); or
d. Derived from SEQ ID NO:4 by removing nucleotides 4 through 180 (corresponding to the native transit peptide) and without the stop codon, optimized for expression in *Arabidopsis* or soybean (dicots) or corn (a monocot), and encoding a CDOL peptide from *Fragilariopsis cylindrus* (SEQ ID NO:8 minus amino acids 2 through 60).

The SADL gene is as follows:
a. Derived from SEQ ID NO:11 by removing nucleotides 1 through 54, (corresponding to the native transit peptide) optimized for expression in *Arabidopsis* or soybean (dicots) or corn (a monocot), and encoding a truncated SADL peptide from Guillardia theta (SEQ ID NO:17 minus amino acids 1 through 18); or
b. Derived from SEQ ID NO:12, by removing nucleotides 1 through 33 (corresponding to the native transit peptide), optimized for expression in *Arabidopsis* or soybean (dicots) or corn (a monocot), and encoding a truncated SADL peptide from *Candida tenuis* (SEQ ID NO:18 minus amino acids 1 through 11); or
c. Derived from SEQ ID NO:13, by removing nucleotides 1 through 12, (corresponding to the native transit peptide) optimized for expression in *Arabidopsis* or soybean (dicots) or corn (a monocot), and encoding a truncated SADL peptide from Cyanidioschyzon merolae (SEQ ID NO:19 minus amino acids 1 through 4); or
d. Derived from SEQ ID NO:14, without the native transit peptide by removing nucleotides 1 through 18 (corresponding to the native transit peptide), optimized for expression in *Arabidopsis* or soybean (dicots) or corn (a monocot), and encoding a truncated SADL peptide from Thalassiosira oceanica (SEQ ID NO:20 minus amino acids 1 through 6).

Step 2: Transform the DNA construct into *Agrobacterium tumefaciens*, select for antibiotic resistance, and confirm the presence of the DNA construct.

Step 3: Transform plant (*Arabidopsis*, soybean, corn, wheat, sugar beet, rice, camelina or canola), select for antibiotic resistance, and confirm the presence of the DNA constructs in the transgenic plant.

Example 13

Development of a Transgenic Plant that Constitutively Expresses CDOL with a Plant Transit Peptide Fused with a Linker to CS/PLP-DC Using Chemical Synthesis Step 1: Use chemical synthesis to make a DNA construct that contains a constitutive promoter, 35S, fused with nucleotide sequence a plastid transit peptide (SEQ ID NO:21), CDOL gene (SEQ ID NO:1, SEQ ID NO:2, SEQ ID NO:3, or SEQ ID NO:4), linker (SEQ ID NO:23), CS/PLP-DC gene (SEQ ID NO:9, or SEQ ID NO:10) without the native transit peptide all in-frame and a NOS terminator. Clone the DNA construct into a binary vector, such as pCambia1300, pCambia2300 or pCambia3200.

The nucleotide sequence for the plastid transit peptide (SEQ ID NO:21) encodes the peptide SEQ ID NO:22.

The CDOL gene is as follows:
a. Derived from SEQ ID NO:1 by removing nucleotides 1 through 159 (corresponding to the native transit peptide) and removing the stop codon, optimized for expression in *Arabidopsis* or soybean (dicots) or corn (a monocot), and encoding a CDOL peptide from *Chlamydomonas reinhardtii* (SEQ ID NO:5 minus amino acids 1 through 53); or
b. Derived from SEQ ID NO:2 by removing nucleotides 1 through 279 (corresponding to the native transit peptide) and removing the stop codon, optimized for expression in *Arabidopsis* or soybean (dicots) or corn (a monocot), and encoding a CDOL peptide from Guillardia *theta* (SEQ ID NO:6 minus amino acids 1 through 93); or
c. Derived from SEQ ID NO:3 by removing nucleotides 1 through 126 (corresponding to the native transit peptide) and removing the stop codon, optimized for expression in *Arabidopsis* or soybean (dicots) or corn (a monocot), and encoding a CDOL peptide from *Candida tenuis* (SEQ ID NO:7 minus amino acids 1 through 42); or
d. Derived from SEQ ID NO:4 by removing nucleotides 1 through 180 (corresponding to the native transit peptide) and removing the stop codon, optimized for expression in *Arabidopsis* or soybean (dicots) or corn (a monocot), and encoding a CDOL peptide from *Fragilariopsis cylindrus* (SEQ ID NO:8 minus amino acids 1 through 60).

The CS/PLP-DC gene is as follows:
a. Derived from SEQ ID NO:9 by removing nucleotides 1 through 234, (corresponding to the native transit peptide) optimized for expression in *Arabidopsis* or soybean (dicots) or corn (a monocot), and encoding a CS/PLP-DC peptide from Micromonas *pusilla* (SEQ ID NO:15 minus amino acids 1 through 78); or
b. Derived from SEQ ID NO:10 by removing nucleotides 1 through 69 (corresponding to the native transit peptide), optimized for expression in *Arabidopsis* or soybean (dicots) or corn (a monocot), and encoding a CS/PLP-DC peptide from Ostreococcus *tauri* (SEQ ID NO:16 minus amino acids 1 through 23).

Step 2: Transform the DNA construct into *Agrobacterium tumefaciens*, select for antibiotic resistance, and confirm the presence of the DNA construct.

Step 3: Transform plant (*Arabidopsis*, soybean, corn, wheat, sugar beet, rice, camelina or canola), select for antibiotic resistance, and confirm the presence of the DNA constructs in the transgenic plant.

Example 14

Development of a Transgenic Plant that Constitutively Expresses CDOL with a Native Transit Peptide Fused with a Linker to partCS/PLP-DC Using Chemical Synthesis Step 1: Use chemical synthesis to make a DNA construct that contains a constitutive promoter, 35S, fused with nucleotide sequence of the CDOL gene (SEQ ID NO:1, SEQ ID NO:2, SEQ ID NO:3, or SEQ ID NO:4), linker (SEQ ID NO:23), partCS/PLP-DC gene (SEQ ID NO:9, or SEQ ID NO:10) all in-frame and a NOS terminator. Clone the DNA construct into a binary vector, such as pCambia1300, pCambia2300 or pCambia3200.

The nucleotide sequence for the plastid transit peptide (SEQ ID NO:21) encodes the peptide SEQ ID NO:22.

The CDOL gene is as follows:
a. Derived from SEQ ID NO:1 without the stop codon, optimized for expression in *Arabidopsis* or soybean (dicots) or corn (a monocot), and encoding a CDOL peptide from *Chlamydomonas reinhardtii* (SEQ ID NO:5); or
b. Derived from SEQ ID NO:2 without the stop codon, optimized for expression in *Arabidopsis* or soybean (dicots) or corn (a monocot), and encoding a CDOL peptide from Guillardia *theta* (SEQ ID NO:6); or
c. Derived from SEQ ID NO:3 without the stop codon, optimized for expression in *Arabidopsis* or soybean (dicots) or corn (a monocot), and encoding a CDOL peptide from *Candida tenuis* (SEQ ID NO:7); or
d. Derived from SEQ ID NO:4 without the stop codon, optimized for expression in *Arabidopsis* or soybean (dicots) or corn (a monocot), and encoding a CDOL peptide from *Fragilariopsis cylindrus* (SEQ ID NO:8).

The partCS/PLP-DC gene is as follows:
a. Derived from SEQ ID NO:9 by removing nucleotides 1 through 1413 (corresponding to the native transit and cysteine synthetase peptides), optimized for expression in *Arabidopsis* or soybean (dicots) or corn (a monocot), and encoding a partCS/PLP-DC peptide from Micromonas *pusilla* (SEQ ID NO:15 minus amino acids 1 through 471); or
b. Derived from SEQ ID NO:10 truncated by removing nucleotides 1 through 1068 (corresponding to the native transit and cysteine synthetase peptides), optimized for expression in *Arabidopsis* or soybean (dicots) or corn (a monocot), and encoding a partCS/PLP-DC peptide from Ostreococcus *tauri* (SEQ ID NO:16 minus amino acids 1 through 356).

Step 2: Transform the DNA construct into *Agrobacterium tumefaciens*, select for antibiotic resistance, and confirm the presence of the DNA construct.

Step 3: Transform plant (*Arabidopsis*, soybean, corn, wheat, sugar beet, rice, camelina or canola), select for antibiotic resistance, and confirm the presence of the DNA constructs in the transgenic plant.

Example 15

Development of a Transgenic Plant that Constitutively Expresses CDOL with a Plant Transit Peptide Fused with a Linker to partCS/PLP-DC Using Chemical Synthesis Step 1: Use chemical synthesis to make a DNA construct that contains a constitutive promoter, 35S, fused with a nucleotide sequence a plastid transit peptide (SEQ ID NO:21), CDOL gene (SEQ ID NO:1, SEQ ID NO:2, SEQ ID NO:3, or SEQ ID NO:4), linker (SEQ ID NO:23), partCS/PLP-DC gene (SEQ ID NO:9, or SEQ ID NO:10) all in-frame and a NOS terminator. Clone the DNA construct into a binary vector, such as pCambia1300, pCambia2300 or pCambia3200.

The nucleotide sequence for the plastid transit peptide (SEQ ID NO:21) encodes the peptide SEQ ID NO:22.

The CDOL gene is as follows:
a. Derived from SEQ ID NO:1 by removing nucleotides 1 through 159 (corresponding to a putative transit peptide) and removing the stop codon, optimized for expression in *Arabidopsis* or soybean (dicots) or corn (a monocot), and encoding a CDOL peptide from *Chlamydomonas reinhardtii* (SEQ ID NO:5 minus amino acids 1 through 53); or
b. Derived from SEQ ID NO:2 by removing nucleotides 1 through 279 (corresponding to the native transit) and removing the stop codon, optimized for expression in *Arabidopsis* or soybean (dicots) or corn (a monocot), and encoding a CDOL peptide from Guillardia *theta* (SEQ ID NO:6 minus amino acids 1 through 93); or
c. Derived from SEQ ID NO:3 by removing nucleotides 1 through 126 (corresponding to the native transit) and removing the stop codon, optimized for expression in *Arabidopsis* or soybean (dicots) or corn (a monocot), and encoding a CDOL peptide from *Candida tenuis* (SEQ ID NO:7 minus amino acids 1 through 42); or
d. Derived from SEQ ID NO:4 by removing nucleotides 1 through 180 (corresponding to the native transit) and removing the stop codon, optimized for expression in *Arabidopsis* or soybean (dicots) or corn (a monocot), and encoding a CDOL peptide from *Fragilariopsis cylindrus* (SEQ ID NO:8 minus amino acids 1 through 60).

The partCS/PLP-DC gene is as follows:
a. Derived from SEQ ID NO:9 by removing nucleotides 1 through 1413, (corresponding to the native transit and cysteine synthetase peptides) optimized for expression in *Arabidopsis* or soybean (dicots) or corn (a monocot), and encoding a partCS/PLP-DC peptide from *Micromonas pusilla* (SEQ ID NO:15 minus amino acids 1 through 471); or
b. Derived from SEQ ID NO:10 by removing nucleotides 1 through 1068 (corresponding to the native transit and cysteine synthetase peptides), optimized for expression in *Arabidopsis* or soybean (dicots) or corn (a monocot), and encoding a partCS/PLP-DC peptide from Ostreococcus *tauri* (SEQ ID NO:16 minus amino acids 1 through 356).

Step 2: Transform the DNA construct into *Agrobacterium tumefaciens*, select for antibiotic resistance, and confirm the presence of the DNA construct.

Step 3: Transform plant (*Arabidopsis*, soybean, corn, wheat, sugar beet, rice, camelina or canola), select for antibiotic resistance, and confirm the presence of the DNA constructs in the transgenic plant.

Example 16

Development of a Transgenic Plant that Constitutively Expresses CDOL without a Transit Peptide and Constitutively Expresses SADL Protein without a Transit Peptide in Tandem with Independent Promoters Step 1: Use chemical synthesis to make a DNA construct that contains a constitutive promoter, 35S, fused with a CDOL gene (SEQ ID NO:1, SEQ ID NO:2, SEQ ID NO:3, or SEQ ID NO:4) with the native transit peptide removed and a NOS terminator. Clone the DNA construct into a binary vector, such as pCambia1300, pCambia2300, or pCambia3200.

The CDOL gene is as follows:
a. Derived from SEQ ID NO:1 by removing nucleotides 4 through 159 (corresponding to the native transit peptide), optimized for expression in *Arabidopsis* or soybean (dicots) or corn (a monocot), and encoding a CDOL peptide from *Chlamydomonas reinhardtii* (SEQ ID NO:5 minus amino acids 2 through 53); or
b. Derived from SEQ ID NO:2 by removing nucleotides 4 through 279 (corresponding to the native transit peptide), optimized for expression in *Arabidopsis* or soybean (dicots) or corn (a monocot), and encoding a CDOL peptide from Guillardia *theta* (SEQ ID NO:6 minus amino acids 2 through 93); or
c. Derived from SEQ ID NO:3 by removing nucleotides 4 through 126 (corresponding to the native transit peptide), optimized for expression in *Arabidopsis* or soybean (dicots) or corn (a monocot), and encoding a CDOL peptide from *Candida tenuis* (SEQ ID NO:7 minus amino acids 2 through 42); or
d. Derived from SEQ ID NO:4 by removing nucleotides 4 through 180 (corresponding to the native transit peptide), optimized for expression in *Arabidopsis* or soybean (dicots) or corn (a monocot), and encoding a CDOL peptide from *Fragilariopsis cylindrus* (SEQ ID NO:8 minus amino acids 2 through 60).

Step 2: Use chemical synthesis to make a DNA construct that contains a constitutive promoter, 35S, fused with a SADL (SEQ ID NO:11, SEQ ID NO:12, SEQ ID NO:13, or SEQ ID NO:14) with the native transit peptide removed and a NOS terminator. Clone the SADL DNA construct into a binary vector that contains the CDOL DNA construct (Step1).

The SADL gene is as follows:
a. Derived from SEQ ID NO:11 by removing nucleotides 4 through 54, (corresponding to a putative transit peptide) optimized for expression in *Arabidopsis* or soybean (dicots) or corn (a monocot), and encoding a truncated SADL peptide from Guillardia *theta* (SEQ ID NO:17 minus amino acids 2 through 18); or
b. Derived from SEQ ID NO:12 by removing nucleotides 4 through 33 (corresponding to the native transit peptide), optimized for expression in *Arabidopsis* or soybean (dicots) or corn (a monocot), and encoding a truncated SADL peptide from *Candida tenuis* (SEQ ID NO:18 minus amino acids 2 through 11); or
c. Derived from SEQ ID NO:13 by removing nucleotides 4 through 12, (corresponding to the native transit peptide) optimized for expression in *Arabidopsis* or soybean (dicots) or corn (a monocot), and encoding a truncated SADL peptide from Cyanidioschyzon merolae (SEQ ID NO:19 minus amino acids 2 through 4); or
d. Derived from SEQ ID NO:14 by removing nucleotides 4 through 18 (corresponding to the native transit peptide), optimized for expression in *Arabidopsis* or soybean (dicots) or corn (a monocot), and encoding a truncated SADL peptide from *Thalassiosira oceanica* (SEQ ID NO:20 minus amino acids 2 through 6).

Step 3: Transform the DNA construct into *Agrobacterium tumefaciens*, select for antibiotic resistance, and confirm the presence of the DNA construct.

Step 4: Transform plant (*Arabidopsis*, soybean, corn, wheat, sugar beet, rice, camelina or canola), select for antibiotic resistance, and confirm the presence of the DNA constructs in the transgenic plant.

Example 17

Development of a Transgenic Plant that Constitutively Expresses CDOL without a Transit Peptide and Constitutively Expresses CS/PLP-DC Protein without Transit Peptide in Tandem with Independent Promoters Step 1: Use chemical synthesis to make a DNA construct that contains a constitutive promoter, 35S, fused with the CDOL gene (SEQ ID NO:1, SEQ ID NO:2, SEQ ID NO:3, or SEQ ID NO:4) with the native transit peptide removed and a NOS terminator. Clone the DNA construct into a binary vector, such as pCambia1300, pCambia2300 or pCambia3200.

The CDOL gene is as follows:
a. Derived from SEQ ID NO:1 by removing nucleotides 4 through 159 (corresponding to the native transit peptide), optimized for expression in *Arabidopsis* or soybean (dicots) or corn (a monocot), and encoding a CDOL peptide from *Chlamydomonas reinhardtii* (SEQ ID NO:5 minus amino acids 2 through 53); or
b. Derived from SEQ ID NO:2 by removing nucleotides 4 through 279 (corresponding to the native transit peptide), optimized for expression in *Arabidopsis* or soybean (dicots) or corn (a monocot), and encoding a CDOL peptide from Guillardia theta (SEQ ID NO:6 minus amino acids 2 through 93); or
c. Derived from SEQ ID NO:3 by removing nucleotides 4 through 126 (corresponding to the native transit peptide), optimized for expression in *Arabidopsis* or soybean (dicots) or corn (a monocot), and encoding a CDOL peptide from *Candida tenuis* (SEQ ID NO:7 minus amino acids 2 through 42); or
d. Derived from SEQ ID NO:4 by removing nucleotides 4 through 180 (corresponding to the native transit peptide), optimized for expression in *Arabidopsis* or soybean (dicots) or corn (a monocot), and encoding a CDOL peptide from *Fragilariopsis cylindrus* (SEQ ID NO:8 minus amino acids 2 through 60).

Step 2: Use chemical synthesis to make a DNA construct that contains a constitutive promoter, 35S, fused with the CS/PLP-DC (SEQ ID NO:9 or SEQ ID NO:10) with the native transit peptide removed and a NOS terminator. The nucleotide sequence for the plastid transit peptide (SEQ ID NO: 21) encodes the peptide SEQ ID NO: 22. Clone the CS/PLP-DC DNA construct into a binary vector that contains the CDOL DNA construct (Step1).

The CS/PLP-DC gene is as follows:
a. Derived from SEQ ID NO:9 by removing nucleotides 4 through 234, (corresponding to the native transit peptide) optimized for expression in *Arabidopsis* or soybean (dicots) or corn (a monocot), and encoding a CS/PLP-DC peptide from Micromonas *pusilla* (SEQ ID NO:15 minus amino acids 2 through 78); or
b. Derived from SEQ ID NO:10 by removing nucleotides 4 through 69 (corresponding to the native transit peptide), optimized for expression in *Arabidopsis* or soybean (dicots) or corn (a monocot), and encoding a CS/PLP-DC peptide from Ostreococcus tauri (SEQ ID NO:16 minus amino acids 2 through 23).

Step 3: Transform the DNA construct into *Agrobacterium tumefaciens*, select for antibiotic resistance, and confirm the presence of the DNA construct.

Step 4: Transform plant (*Arabidopsis*, soybean, corn, wheat, sugar beet, rice, camelina or canola), select for antibiotic resistance, and confirm the presence of the DNA constructs in the transgenic plant.

Example 18

Development of a Transgenic Plant that Constitutively Expresses CDOL without a Transit Peptide and Constitutively Expresses partCS/PLP-DC Protein without a Transit Peptide in Tandem with Independent Promoters Step 1: Use chemical synthesis to make a DNA construct that contains a constitutive promoter, 35S, fused with CDOL gene (SEQ ID NO:1, or SEQ ID NO:2, SEQ ID NO:3 or SEQ ID NO:4) with the native transit peptide removed and a NOS terminator. Clone the DNA construct into a binary vector, such as pCambia1300, pCambia2300 or pCambia3200.

The CDOL gene is as follows:
a. Derived from SEQ ID NO:1 by removing nucleotides 4 through 159 (corresponding to the native transit peptide), optimized for expression in *Arabidopsis* or soybean (dicots) or corn (a monocot), and encoding a CDOL peptide from *Chlamydomonas reinhardtii* (SEQ ID NO:5 minus amino acids 2 through 53); or
b. Derived from SEQ ID NO:2 by removing nucleotides 4 through 279 (corresponding to the native transit peptide), optimized for expression in *Arabidopsis* or soybean (dicots) or corn (a monocot), and encoding a CDOL peptide from Guillardia theta (SEQ ID NO:6 minus amino acids 2 through 93): or
c. Derived from SEQ ID NO:3 by removing nucleotides 4 through 126 (corresponding to the native transit peptide), optimized for expression in *Arabidopsis* or soybean (dicots) or corn (a monocot), and encoding a CDOL peptide from *Candida tenuis* (SEQ ID NO:7 minus amino acids 2 through 42); or
d. Derived from SEQ ID NO:4 by removing nucleotides 4 through 180 (corresponding to the native transit peptide), optimized for expression in *Arabidopsis* or soybean (dicots) or corn (a monocot), and encoding a CDOL peptide from *Fragilariopsis cylindrus* (SEQ ID NO:8 minus amino acids 2 through 60).

Step 2: Use chemical synthesis to make a DNA construct that contains a constitutive promoter, 35S, fused with the partCS/PLP-DC (SEQ ID NO:9 or SEQ ID NO:10) and a NOS terminator. Clone the partCS/LP-DC DNA construct into a binary vector that contains the CDOL DNA construct (Step1).

The partCS/PLP-DC gene is as follows:
a. Derived from SEQ ID NO:9 by removing nucleotides 4 through 1413, (corresponding to the native transit and cysteine synthetase peptides) optimized for expression in *Arabidopsis* or soybean (dicots) or corn (a monocot), and encoding a partCS/PLP-DC peptide from *Micromonas pusilla* (SEQ ID NO:15 minus amino acids 2 through 471); or
b. Derived from SEQ ID NO:10 by removing nucleotides 4 through 1068 (corresponding to the native transit and cysteine synthetase peptides), optimized for expression in *Arabidopsis* or soybean (dicots) or corn (a monocot), and encoding a partCS/PLP-DC peptide from *Ostreococcus tauri* (SEQ ID NO:16 minus amino acids 2 through 356).

Step 3: Transform the DNA construct into *Agrobacterium tumefaciens*, select for antibiotic resistance, and confirm the presence of the DNA construct.

Step 4: Transform plant (*Arabidopsis*, soybean, corn, wheat, sugar beet, rice, camelina or canola), select for antibiotic resistance, and confirm the presence of the DNA constructs in the transgenic plant.

Example 19

Development of a Transgenic Plant that Constitutively Expresses partCS/PLP-DC without a Transit Peptide Step 1: Use chemical synthesis to make a DNA construct that contains a constitutive promoter, 35S, fused with nucleotide sequence for partCS/PLP-DC (SEQ ID NO:9 or SEQ ID NO:10) and a NOS terminator. Clone the DNA construct into a binary vector, such as pCambia1300, pCambia2300, or pCambia3200.

The partCS/PLP-DC gene is as follows:
a. Derived from SEQ ID NO:9 by removing nucleotides 4 through 1413, (corresponding to a putative transit and cysteine synthetase peptides) optimized for expression in *Arabidopsis* or soybean (dicots) or corn (a monocot), and encoding a partCS/PLP-DC peptide from *Micromonas pusilla* (SEQ ID NO:15 minus amino acids 2 through 471); or
b. Derived from SEQ ID NO:10 by removing nucleotides 4 through 1068 (corresponding to a putative transit and cysteine synthetase peptides), optimized for expression in *Arabidopsis* or soybean (dicots) or corn (a monocot), and encoding a partCS/PLP-DC peptide from *Ostreococcus tauri* (SEQ ID NO:16 minus amino acids 2 through 356).

Step 2: Transform the DNA construct into *Agrobacterium tumefaciens*, select for antibiotic resistance, and confirm the presence of the DNA construct.

Step 3: Transform plant (*Arabidopsis*, soybean, corn, wheat, sugar beet, rice, camelina or canola), select for antibiotic resistance, and confirm the presence of the DNA constructs in the transgenic plant.

Example 20

Development of a Transgenic Plant that Constitutively Expresses partCS/PLP-DC with a Plant Plastid Transit Peptide Step 1: Use chemical synthesis to make a DNA construct that contains a constitutive promoter, 35S, fused with the nucleotide sequence for a plastid transit peptide (SEQ ID NO: 21), partCS/PLP-DC (SEQ ID NO:9 or SEQ ID NO:10) and a NOS terminator. Clone the DNA construct into a binary vector, such as pCambia1300, pCambia2300, or pCambia3200.

The nucleotide sequence for the plastid transit peptide (SEQ ID NO: 21) encodes the peptide SEQ ID NO: 22.

The partCS/PLP-DC gene is as follows:
a. Derived from SEQ ID NO:9 by removing nucleotides 1 through 1413 (corresponding to a putative transit and cysteine synthetase peptides) optimized for expression in *Arabidopsis* or soybean (dicots) or corn (a monocot), and encoding a partCS/PLP-DC peptide from *Micromonas pusilla* (SEQ ID NO:15 minus amino acids 1 through 471); or b. Derived from SEQ ID NO:10 by removing nucleotides 1 through 1068 (corresponding to the native transit and cysteine synthetase peptides), optimized for expression in *Arabidopsis* or soybean (dicots) or corn (a monocot), and encoding a partCS/PLP-DC peptide from Ostreococcus tauri (SEQ ID NO:16 minus amino acids 1 through 356).

Step 2: Transform the DNA construct into *Agrobacterium tumefaciens*, select for antibiotic resistance, and confirm the presence of the DNA construct.

Step 3: Transform plant (*Arabidopsis*, soybean, corn, wheat, sugar beet, rice, camelina or canola), select for antibiotic resistance, and confirm the presence of the DNA constructs in the transgenic plant.

Example 21

Development of a Transgenic Plant that Constitutively Expresses CS/PLP-DC without a Transit Peptide Step 1: Use chemical synthesis to make a DNA construct that contains a constitutive promoter, 35S, fused with nucleotide sequence for CS/PLP-DC (SEQ ID NO:9 or SEQ ID NO:10) with the native transit peptide removed and a NOS terminator. Clone the DNA construct into a binary vector, such as pCambia1300, pCambia2300, or pCambia3200.

The CS/PLP-DC gene is as follows:
a. Derived from SEQ ID NO:9 by removing nucleotides 4 through 234, (corresponding to the native transit peptide) optimized for expression in *Arabidopsis* or soybean (dicots) or corn (a monocot), and encoding a CS/PLP-DC peptide from Micromonas *pusilla* (SEQ ID NO:15 minus amino acids 2 through 78); or b. Derived from SEQ ID NO:10 without the native transit peptide by removing nucleotides 4 through 69 (corresponding to the native transit peptide), optimized for expression in *Arabidopsis* or soybean (dicots) or corn (a monocot), and encoding a CS/PLP-DC peptide from Ostreococcus tauri (SEQ ID NO:16 minus amino acids 2 through 23).

Step 2: Transform the DNA construct into *Agrobacterium tumefaciens*, select for antibiotic resistance, and confirm the presence of the DNA construct.

Step 3: Transform plant (*Arabidopsis*, soybean, corn, wheat, sugar beet, rice, camelina or canola), select for antibiotic resistance, and confirm the presence of the DNA constructs in the transgenic plant.

Example 22

Development of a Bacterial Strain that Expresses CDOL without a Native Transit Peptide Fused (without a Linker) to a SADL without a Native Transit Peptide Using Chemical Synthesis Step 1: Use chemical synthesis to make a DNA construct that contains a CDOL gene (SEQ ID NO:1, SEQ ID NO:2, SEQ ID NO:3, or SEQ ID NO:4) without the native transit peptide, and SADL gene (SEQ ID NO:11, SEQ ID NO:12, SEQ ID NO:13, or SEQ ID NO:14) without the native transit peptide all in-frame. Clone the DNA construct into a bacterial expression vector, such as pKK233-2, pGEX (GE Healthcare), pET (Novagen) and pMAL™ (New England biolabs) in a manner that the construct is operably functional.

The CDOL gene is as follows:

a. Derived from SEQ ID NO:1 by removing nucleotides 4 through 159 (corresponding to the native transit peptide) and without the stop codon, optimized for expression in *Arabidopsis* or soybean (dicots) or corn (a monocot), and encoding a CDOL peptide from *Chlamydomonas reinhardtii* (SEQ ID NO:5 minus amino acids 2 through 53); or b. Derived from SEQ ID NO:2 by removing nucleotides 4 through 279 (corresponding to the native transit peptide) and without the stop codon, optimized for expression in *Arabidopsis* or soybean (dicots) or corn (a monocot), and encoding a CDOL peptide from Guillardia theta (SEQ ID NO:6 minus amino acids 2 through 93); or c. Derived from SEQ ID NO:3 by removing nucleotides 4 through 126 (corresponding to the native transit peptide) and without the stop codon, optimized for expression in *Arabidopsis* or soybean (dicots) or corn (a monocot), and encoding a CDOL peptide from *Candida tenuis* (SEQ ID NO:7 minus amino acids 2 through 42); or d. Derived from SEQ ID NO:4 by removing nucleotides 4 through 180 (corresponding to the native transit peptide) and without the stop codon, optimized for expression in *Arabidopsis* or soybean (dicots) or corn (a monocot), and encoding a CDOL peptide from *Fragilariopsis cylindrus* (SEQ ID NO:8 minus amino acids 2 through 60).

The SADL gene is as follows:

a. Derived from SEQ ID NO:11 by removing nucleotides 1 through 54, (corresponding to the native transit peptide) optimized for expression in *Arabidopsis* or soybean (dicots) or corn (a monocot), and encoding a truncated SADL peptide from Guillardia theta (SEQ ID NO:17 minus amino acids 1 through 18); or b. Derived from SEQ ID NO:12, by removing nucleotides 1 through 33 (corresponding to the native transit peptide), optimized for expression in *Arabidopsis* or soybean (dicots) or corn (a monocot), and encoding a truncated SADL peptide from *Candida tenuis* (SEQ ID NO:18 minus amino acids 1 through 11); or c. Derived from SEQ ID NO:13, by removing nucleotides 1 through 12, (corresponding to the native transit peptide) optimized for expression in *Arabidopsis* or soybean (dicots) or corn (a monocot), and encoding a truncated SADL peptide from Cyanidioschyzon merolae (SEQ ID NO:19 minus amino acids 1 through 4); or d. Derived from SEQ ID NO:14, without the native transit peptide by removing nucleotides 1 through 18 (corresponding to the native transit peptide), optimized for expression in *Arabidopsis* or soybean (dicots) or corn (a monocot), and encoding a truncated SADL peptide from *Thalassiosira* oceanica (SEQ ID NO:20 minus amino acids 1 through 6).

Step 2: Transform the DNA construct into bacteria *Escherichia coli, B. subtilis*, select for antibiotic resistance, and confirm the presence of the DNA construct.

Example 23

Development of a Bacterial Strain that Express CDOL without Transit Peptide Fused with a Linker to SADL without a Native Transit Peptide Using Chemical Synthesis Step 1: Use chemical synthesis to make a DNA construct that contains a CDOL gene (SEQ ID NO:1, SEQ ID NO:2, SEQ ID NO:3, or SEQ ID NO:4) without the transit peptide, linker (SEQ ID NO:23), and SADL gene (SEQ ID NO:11, SEQ ID NO:12, SEQ ID NO:13, or SEQ ID NO:14) without the transit peptide all in-frame. Clone the DNA construct into a bacterial expression vector, such as pKK233-2, pGEX (GE Healthcare), pET (Novagen) and pMAL™ (New England biolabs) in a manner that the construct is operably functional.

The CDOL gene is as follows:
a. Derived from SEQ ID NO:1 by removing nucleotides 4 through 159 (corresponding to the native transit peptide) and without the stop codon, optimized for expression in *Arabidopsis* or soybean (dicots) or corn (a monocot), and encoding a CDOL peptide from *Chlamydomonas reinhardtii* (SEQ ID NO:5 minus amino acids 2 through 53); or
b. Derived from SEQ ID NO:2 by removing nucleotides 4 through 279 (corresponding to the native transit peptide) and without the stop codon, optimized for expression in *Arabidopsis* or soybean (dicots) or corn (a monocot), and encoding a CDOL peptide from Guillardia theta (SEQ ID NO:6 minus amino acids 2 through 93); or
c. Derived from SEQ ID NO:3 by removing nucleotides 4 through 126 (corresponding to the native transit peptide) and without the stop codon, optimized for expression in *Arabidopsis* or soybean (dicots) or corn (a monocot), and encoding a CDOL peptide from *Candida tenuis* (SEQ ID NO:7 minus amino acids 2 through 42); or
d. Derived from SEQ ID NO:4 by removing nucleotides 4 through 180 (corresponding to the native transit peptide) and without the stop codon, optimized for expression in *Arabidopsis* or soybean (dicots) or corn (a monocot), and encoding a CDOL peptide from *Fragilariopsis cylindrus* (SEQ ID NO:8 minus amino acids 2 through 60).

The SADL gene is as follows:
a. Derived from SEQ ID NO:11 by removing nucleotides 1 through 54, (corresponding to the native transit peptide) optimized for expression in *Arabidopsis* or soybean (dicots) or corn (a monocot), and encoding a truncated SADL peptide from Guillardia theta (SEQ ID NO:17 minus amino acids 1 through 18); or
b. Derived from SEQ ID NO:12, by removing nucleotides 1 through 33 (corresponding to the native transit peptide), optimized for expression in *Arabidopsis* or soybean (dicots) or corn (a monocot), and encoding a truncated SADL peptide from *Candida tenuis* (SEQ ID NO:18 minus amino acids 1 through 11); or
c. Derived from SEQ ID NO:13, by removing nucleotides 1 through 12, (corresponding to the native transit peptide) optimized for expression in *Arabidopsis* or soybean (dicots) or corn (a monocot), and encoding a truncated SADL peptide from Cyanidioschyzon merolae (SEQ ID NO:19 minus amino acids 1 through 4); or
d. Derived from SEQ ID NO:14, without the native transit peptide by removing nucleotides 1 through 18 (corresponding to the native transit peptide), optimized for expression in *Arabidopsis* or soybean (dicots) or corn (a monocot), and encoding a truncated SADL peptide from Thalassiosira oceanica (SEQ ID NO:20 minus amino acids 1 through 6).

Step 2: Transform the DNA construct into bacteria *Escherichia coli*, *B. subtilis*, select for antibiotic resistance, and confirm the presence of the DNA construct.

Example 24

Development of a Bacterial Strain that Express CDOL without Transit Peptide Fused with a Linker to partCS/PLP-DC without a Native Transit Peptide Using Chemical Synthesis Step 1: Use chemical synthesis to make a DNA construct with a CDOL gene (SEQ ID NO:1, SEQ ID NO:2, SEQ ID NO:3, or SEQ ID NO:4) without the transit peptide, linker (SEQ ID NO:23), and partCS/PLP-DC (SEQ ID NO:9 or SEQ ID NO:10) all in-frame. Clone the DNA construct into a bacterial expression vector, such as pKK233-2, pGEX (GE Healthcare), pET (Novagen) and pMAL™ (New England biolabs) in a manner that the construct is operably functional.

The CDOL gene is as follows:
a. Derived from SEQ ID NO:1 by removing nucleotides 4 through 159 (corresponding to the native transit peptide) and without the stop codon, optimized for expression in *Arabidopsis* or soybean (dicots) or corn (a monocot), and encoding a CDOL peptide from *Chlamydomonas reinhardtii* (SEQ ID NO:5 minus amino acids 2 through 53); or
b. Derived from SEQ ID NO:2 by removing nucleotides 4 through 279 (corresponding to the native transit peptide) and without the stop codon, optimized for expression in *Arabidopsis* or soybean (dicots) or corn (a monocot), and encoding a CDOL peptide from Guillardia theta (SEQ ID NO:6 minus amino acids 2 through 93); or
c. Derived from SEQ ID NO:3 by removing nucleotides 4 through 126 (corresponding to the native transit peptide) and without the stop codon, optimized for expression in *Arabidopsis* or soybean (dicots) or corn (a monocot), and encoding a CDOL peptide from *Candida tenuis* (SEQ ID NO:7 minus amino acids 2 through 42); or
d. Derived from SEQ ID NO:4 by removing nucleotides 4 through 180 (corresponding to the native transit peptide) and without the stop codon, optimized for expression in *Arabidopsis* or soybean (dicots) or corn (a monocot), and encoding a CDOL peptide from *Fragilariopsis cylindrus* (SEQ ID NO:8 minus amino acids 2 through 60).

The partCS/PLP-DC gene is as follows:
a. Derived from SEQ ID NO:9, by removing nucleotides 1 through 1413, (corresponding to the native transit and cysteine synthetase peptides) optimized for expression in *Arabidopsis* or soybean (dicots) or corn (a monocot), and encoding a partCS/PLP-DC peptide from Micromonas *pusilla* (SEQ ID NO:15 minus amino acids 1 through 471); or
b. Derived from SEQ ID NO:10, by removing nucleotides 1 through 1068 (corresponding to the native transit peptide and cysteine synthetase peptides), optimized for expression in *Arabidopsis* or soybean (dicots) or corn (a monocot), and encoding a partCS/PLP-DC peptide from Ostreococcus tauri (SEQ ID NO:16 minus amino acids 1 through 356).

Step 2: Transform the DNA construct into bacteria *Escherichia coli*, *B. subtilis*, select for antibiotic resistance, and confirm the presence of the DNA construct.

Example 25

Development of a Bacterial Strain that Express CDOL without Transit Peptide Fused with a Linker to CS/PLP-DC without a Native Transit Peptide Using Chemical Synthesis Step 1: Use chemical synthesis to make a DNA construct with a CDOL gene (SEQ ID NO:1, SEQ ID NO:2, SEQ ID NO:3, or SEQ ID NO:4) without the transit peptide, linker (SEQ ID NO:23), and CS/PLP-DC (SEQ ID NO:9 or SEQ ID NO:10) all in-frame. Clone the DNA construct into a bacterial expression vector, such as pKK233-2, pGEX (GE Healthcare), pET (Novagen) and pMAL™ (New England biolabs) in a manner that the construct is operably functional.

The CDOL gene is as follows:

a. Derived from SEQ ID NO:1 by removing nucleotides 4 through 159 (corresponding to the native transit peptide) and without the stop codon, optimized for expression in *Arabidopsis* or soybean (dicots) or corn (a monocot), and encoding a CDOL peptide from *Chlamydomonas reinhardtii* (SEQ ID NO:5 minus amino acids 2 through 53); or b. Derived from SEQ ID NO:2 by removing nucleotides 4 through 279 (corresponding to the native transit peptide) and without the stop codon, optimized for expression in *Arabidopsis* or soybean (dicots) or corn (a monocot), and encoding a CDOL peptide from Guillardia theta (SEQ ID NO:6 minus amino acids 2 through 93); or c. Derived from SEQ ID NO:3 by removing nucleotides 4 through 126 (corresponding to the native transit peptide) and without the stop codon, optimized for expression in *Arabidopsis* or soybean (dicots) or corn (a monocot), and encoding a CDOL peptide from *Candida tenuis* (SEQ ID NO:7 minus amino acids 2 through 42); or d. Derived from SEQ ID NO:4 by removing nucleotides 4 through 180 (corresponding to the native transit peptide) and without the stop codon, optimized for expression in *Arabidopsis* or soybean (dicots) or corn (a monocot), and encoding a CDOL peptide from *Fragilariopsis cylindrus* (SEQ ID NO:8 minus amino acids 2 through 60).

The CS/PLP-DC gene is as follows:

a. Derived from SEQ ID NO:9 by removing nucleotides 1 through 234, (corresponding to the native transit peptide) optimized for expression in *Arabidopsis* or soybean (dicots) or corn (a monocot), and encoding a CS/PLP-DC peptide from Micromonas *pusilla* (SEQ ID NO:15 minus amino acids 1 through 78); or b. Derived from SEQ ID NO:10 without the native transit peptide by removing nucleotides 1 through 69 (corresponding to the native transit peptide), optimized for expression in *Arabidopsis* or soybean (dicots) or corn (a monocot), and encoding a CS/PLP-DC peptide from Ostreococcus tauri (SEQ ID NO:16 minus amino acids 1 through 23).

Step 2: Transform the DNA construct into bacteria *Escherichia coli, B. subtilis*, select for antibiotic resistance, and confirm the presence of the DNA construct.

Example 26

Development of a Bacterial Strain that Expresses CS/PLP-DC without a Native Transit Peptide Using Chemical Synthesis Step 1: Use chemical synthesis to make a DNA construct with a CS/PLP-DC (SEQ ID NO:9 or SEQ ID NO:10). Clone the DNA construct into a bacterial expression vector, such as pKK233-2, pGEX (GE Healthcare), pET (Novagen) and pMAL™ (New England biolabs) in a manner that the construct is operably functional.

The CS/PLP-DC gene is as follows:

a. Derived from SEQ ID NO:9 by removing nucleotides 4 through 234, (corresponding to the native transit peptide) optimized for expression in *Arabidopsis* or soybean (dicots) or corn (a monocot), and encoding a CS/PLP-DC peptide from Micromonas *pusilla* (SEQ ID NO:15 minus amino acids 2 through 78); or b. Derived from SEQ ID NO:10 without the native transit peptide by removing nucleotides 4 through 69 (corresponding to the native transit peptide), optimized for expression in *Arabidopsis* or soybean (dicots) or corn (a monocot), and encoding a CS/PLP-DC peptide from Ostreococcus tauri (SEQ ID NO:16 minus amino acids 2 through 23).

Step 2: Transform the DNA construct into bacteria *Escherichia coli, B. subtilis*, select for antibiotic resistance, and confirm the presence of the DNA construct.

Example 27

Development of a Transgenic Plant that Expresses in the Seed CDOL without Transit Peptide Fused with a Linker to partCS/PLP-DC Using Chemical Synthesis Step 1: Use chemical synthesis to make a DNA construct that contains a seed-specific promoter, beta-conglycinin, fused with nucleotide sequence of a CDOL gene (SEQ ID NO:1, SEQ ID NO:2, SEQ ID NO:3, or SEQ ID NO:4) without the transit peptide, linker (SEQ ID NO:23), SADL gene (SEQ ID NO:11, SEQ ID NO:12, SEQ ID NO:13, or SEQ ID NO:14) without the transit peptide all in-frame and a beta-conglycinin terminator. Clone the DNA construct into a binary vector, such as pCambia1300, pCambia2300 or pCambia3200.

The CDOL gene is as follows:

a. Derived from SEQ ID NO:1 by removing nucleotides 4 through 159 (corresponding to the native transit peptide) and without the stop codon, optimized for expression in *Arabidopsis* or soybean (dicots) or corn (a monocot), and encoding a CDOL peptide from *Chlamydomonas reinhardtii* (SEQ ID NO:5 minus amino acids 2 through 53); or b. Derived from SEQ ID NO:2 by removing nucleotides 4 through 279 (corresponding to the native transit peptide) and without the stop codon, optimized for expression in *Arabidopsis* or soybean (dicots) or corn (a monocot), and encoding a CDOL peptide from Guillardia theta (SEQ ID NO:6 minus amino acids 2 through 93); or c. Derived from SEQ ID NO:3 by removing nucleotides 4 through 126 (corresponding to the native transit peptide) and without the stop codon, optimized for expression in *Arabidopsis* or soybean (dicots) or corn (a monocot), and encoding a CDOL peptide from *Candida tenuis* (SEQ ID NO:7 minus amino acids 2 through 42); or d. Derived from SEQ ID NO:4 by removing nucleotides 4 through 180 (corresponding to the native transit peptide) and without the stop codon, optimized for expression in *Arabidopsis* or soybean (dicots) or corn (a monocot), and encoding a CDOL peptide from *Fragilariopsis cylindrus* (SEQ ID NO:8 minus amino acids 2 through 60).

The partCS/PLP-DC gene is as follows:
a. Derived from SEQ ID NO:9 by removing nucleotides 1 through 1413 (corresponding to the native transit and cysteine synthetase peptides), optimized for expression in *Arabidopsis* or soybean (dicots) or corn (a monocot), and encoding a partCS/PLP-DC peptide from Micromonas *pusilla* (SEQ ID NO:15 minus amino acids 1 through 471); or
b. Derived from SEQ ID NO:10 truncated by removing nucleotides 1 through 1068 (corresponding to the native transit and cysteine synthetase peptides), optimized for expression in *Arabidopsis* or soybean (dicots) or corn (a monocot), and encoding a partCS/PLP-DC peptide from Ostreococcus tauri (SEQ ID NO:16 minus amino acids 1 through 356).

Step 2: Transform the DNA construct into *Agrobacterium tumefaciens*, select for antibiotic resistance, and confirm the presence of the DNA construct.

Step 3: Transform plant (*Arabidopsis*, soybean, corn, wheat, sugar beet, rice, camelina or canola), select for antibiotic resistance, and confirm the presence of the DNA constructs in the transgenic plant.

Example 28

Develop a Plant with Taurine

Figure 2:
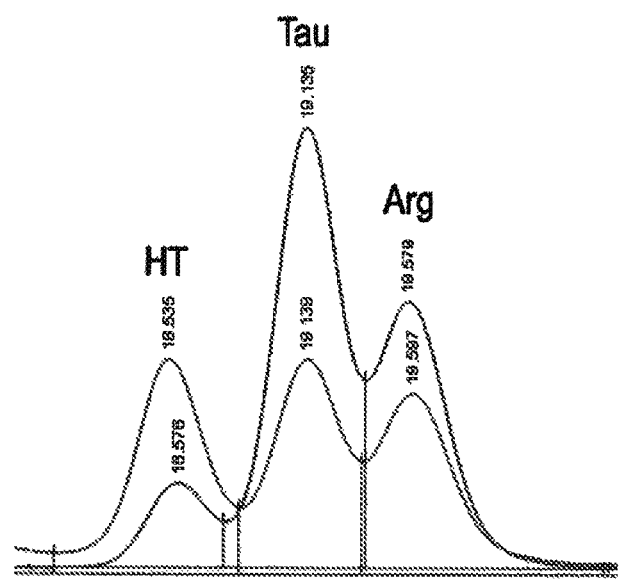
FIG. 2 shows the superposition of two chromatograms: one from the amino acid extract of a representative transgenic plant containing the CDOL-linker-partCS/PLP-DC (lower line at Tau) and the other is a reference, i.e., the amino acid standards (higher line at Tau). The numbers represent the retention times, and the peaks for hypotaurine (HT), taurine (Tau), and arginine (Arg) are labeled.

This example demonstrates the use of an CDOL fused to SADL with a linker (CDOL-linker-partCS/PLP-DC) (such as from Example #27) to produce hypotaurine and taurine in a seed. Transformed *Arabidopsis* plants were confirmed by selection and PCR analysis. Transgenic plants were grown in soil (Metro Mix 360) for 60 days. The growth conditions were maintained at 20-21° C., under cool white fluorescent lights (120 umol of photons per $m^2$ per s) with a 16-h light/8-h dark cycle. Plants were grown to maturity. Dried seeds were harvested. Free amino acids were extracted from the dry brown seeds to determine the level of taurine using high-performance liquid chromatography (HPLC). The results are shown in FIG. 2 which shows hypotaurine and taurine levels in the transgenic line were 6.95% and 5.2%, respectively, of the total extracted free amino acids.

Example 29

Develop Aquafeed Using Plant Tissue with Taurine

Grow plants from seed of transgenic plants that constitutively express CDOL fused to SADL with a linker (CDOL-linker-SADL) (such as from Example #10). Collect the seeds, grind to a powder and use as an additive in feed.

Example 30

Develop Bacteria with Taurine

Grow bacteria with CS/PLP-DC (such as from Example #26) and induce gene expression with the appropriate inducer as suggested the vector. Collect the cells and confirm that the cells express the CS/PLP-DC peptide (~96.6 kDa) using western blot analysis and that have increased taurine using HPLC analysis.

Example 31

Develop Aquafeed Using Bacterial Cells with Taurine

Grow bacteria with CS/PLP-DC (such as from Example #26) and induce gene expression with the appropriate inducer associated with the vector. Collect the cells and process for use as an additive to feed.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A prokaryotic cell comprising either:
   (a) two expression units, wherein
      (i) a first expression unit that comprises a first promoter operably linked to a first polynucleotide which encodes cysteine dioxygenase-like (CDOL) protein; and
      (ii) a second expression unit that comprises a second promoter operably linked to a second polynucleotide which encodes a portion of the cysteine synthetase/PLP decarboxylase (partCS/PLP-DC) protein, wherein the partCS/PLP-DC protein comprises amino acids 1 plus 472 through 985 of the amino acid sequence set forth in SEQ ID NO:15 or an amino acid sequence having at least 95% sequence identity thereto; or
   (b) a single expression unit which comprises a promoter operably linked to a first polynucleotide which encodes the CDOL protein operably linked to (i) a second polynucleotide which encodes the partCS/PLP-DC protein or (ii) a third polynucleotide which encodes cysteine synthetase/PLP decarboxylase (CS/PLP-DC) protein comprising the amino acid sequence set forth in SEQ ID NO: 1 or an amino acid sequence having at least 95% sequence identity thereto,
   wherein the two expression units or the single expression unit is expressed in the prokaryotic cell and wherein the prokaryotic cell produces taurine.

2. The prokaryotic cell of claim 1, wherein the first polynucleotide which encodes the CDOL protein comprises the nucleotide sequence set forth in SEQ ID NO:1.

3. The prokaryotic cell of claim 1, wherein the second polynucleotide which encodes the partCS/PLP-DC protein comprises nucleotides 1 through 3 plus 1414 through 2958 of the nucleotide sequence set forth in SEQ ID NO:9.

4. The prokaryotic cell of claim 1, wherein the third polynucleotide which encodes the CS/PLP-DC protein comprises the nucleotide sequence set forth in SEQ ID NO:9.

5. The prokaryotic cell of claim 1, wherein the CDOL protein comprises the amino acid sequence set forth in SEQ ID NO:5 or an amino acid sequence having at least 95% sequence identity thereto.

6. The prokaryotic cell of claim 1, wherein the second polynucleotide encodes the partCS/PLP-DC protein comprising amino acids 1 plus 472 through 985 of the amino acid sequence set forth in SEQ ID NO:15.

7. The prokaryotic cell of claim 1, wherein the third polynucleotide encodes the CS/PLP-DC protein comprising the amino acid sequence set forth in SEQ ID NO:15.

8. A method of producing hypotaurine or taurine, comprising growing the prokaryotic cell of claim 1 under conditions which permit expression of the first and second polynucleotides of the two expression units or expression of (i) the first and second polynucleotides of the single expression unit or (ii) the first and third polypeptides of the single expression unit, thereby producing taurine.

9. A method of producing hypotaurine or taurine, comprising growing the prokaryotic cell of claim 5 under conditions which permit expression of the first and second polynucleotides of the two expression units or expression of (i) the first and second polynucleotides of the single expression unit or (ii) the first and third polypeptides of the single expression unit, thereby producing taurine.

10. A method of producing hypotaurine or taurine, comprising growing the prokaryotic cell of claim 6 under conditions which permit expression of the first and second polynucleotides of the two expression units or expression of (i) the first and second polynucleotides of the single expression unit or (ii) the first and third polypeptides of the single expression unit, thereby producing taurine.

11. A method of producing hypotaurine or taurine, comprising growing the prokaryotic cell of claim 7 under conditions which permit expression of the first and second polynucleotides of the two expression units or expression of (i) the first and second polynucleotides of the single expression unit or (ii) the first and third polypeptides of the single expression unit, thereby producing taurine.

12. A prokaryotic cell comprising a single expression unit which comprises a promoter operatively linked to a polynucleotide which encodes cysteine synthetase/PLP decarboxylase (CS/PLP-DC) protein comprising the amino acid sequence set forth in SEQ ID NO:15 or an amino acid sequence having at least 95% sequence identity thereto,
wherein the single expression unit is expressed in the prokaryotic cell and wherein the prokaryotic cell produces taurine.

13. The prokaryotic cell of claim 12, wherein the CS/PLP-DC protein comprises the amino acid sequence set forth in SEQ ID NO:15.

14. The prokaryotic cell of claim 12, wherein the prokaryotic cell is *Bacillus, Salmonella, Lactococcus, Streptococcus, Brevibacterium*, coryneform bacteria, *Bacillus subtilis, Brevibacterium ammoniagene, Corynebacterium* crenatum, Corynebacterim pekinese, *Corynebacterium* glutamicumas, *Erwinia citreus, Erwinia herbicola, Escherichia coli, Gluconobacter oxydans, Propionibacterium freudenreicheii*, or *Propionibacterium denitrificans*.

15. A method of producing hypotaurine or taurine, comprising growing the prokaryotic cell of claim 12 under conditions which permit expression of the polynucleotide of the single expression unit, thereby producing taurine.

16. A method of producing hypotaurine or taurine, comprising growing the prokaryotic cell of claim 13 under conditions which permit expression of the polynucleotide, thereby producing taurine.

17. A prokaryotic cell comprising a single expression unit which comprises a promoter operatively linked to a polynucleotide which encodes a portion of the cysteine synthetase/PLP decarboxylase (CS/PLP-DC) protein wherein the partCS/PLP-DC protein comprises amino acids 1 plus 472 through 985 of the amino acid sequence set forth in SEQ ID NO:15 or an amino acid sequence having at least 95% sequence identity thereto,
wherein the single expression unit is expressed in the prokaryotic cell and wherein the prokaryotic cell produces taurine.

18. The prokaryotic cell of claim 17, wherein the polynucleotide encodes the partCS/PLP-DC protein comprising amino acids 1 plus 472 through 985 of the amino acid sequence set forth in SEQ ID NO:15.

19. A method of producing hypotaurine or taurine, comprising growing the prokaryotic cell of claim 17 under conditions which permit expression of the polynucleotide, thereby producing taurine.

20. A method of producing hypotaurine or taurine, comprising growing the prokaryotic cell of claim 18 under conditions which permit expression of the polynucleotide, thereby producing taurine.

* * * * *

SEQUENCE LISTING

<160> NUMBER OF SEQ ID NOS: 23

<210> SEQ ID NO 1
<211> LENGTH: 810
<212> TYPE: DNA
<213> ORGANISM: Chlamydomonas reinhardtii

<400> SEQUENCE: 1

| | | | | | | |
|---|---|---|---|---|---|---|
| atgtcttcta | tcatcgctat | gcctatcaac | gaggacggtg | tcgttgtggt | cgaccgcaag | 60 |
| ctgctgggca | acgaggtcga | gagcaaggcc | cgctgcgcgg | acaccgcctg | caccgcggct | 120 |
| gcgcccgccc | cgcccgccac | ggcggccgcg | cccacctcca | tgccggagct | gttgcaggcg | 180 |
| ttgcagcgcg | ccattgacga | ggagaaggcc | actggccagg | tcgccatcaa | cgctgtggac | 240 |
| cagacgcccg | agtccgctgc | gcggctgagc | gcccgcgtgc | aggctctact | ctcggcctac | 300 |
| accagctcca | actcgggcga | ctggcgacgc | tacgccatgt | tcaacgacat | ccactacgtg | 360 |
| cgcaacctgg | tggatgccaa | tgaggacttt | gaactaattg | ttctttgttg | gaagcgcggg | 420 |
| caagtcagcc | gcgtgcacaa | ccacgccaac | gcgcactgct | ggctggcggt | gctggacggc | 480 |
| gagatgcgcg | agacgcagtt | ccagcgcgcg | tccgcgccgc | ccggctgccc | cgcgcccgcg | 540 |
| gcctcggagc | acgatggcag | cactgtgtac | gtggagccca | cacaggtgtc | cgacatgcga | 600 |
| gtgggtgacg | ccggctacat | caacgactcc | atggcgctgc | acaacgtggg | gtgttgcatg | 660 |
| cccgccctgg | ccgctggcga | ggagggcccc | gagggcgggg | tgacgctgca | ctgctacgcc | 720 |
| cccccgattc | gccgcgtcaa | gatctatgag | gacagcaagg | tcacggagcg | cgtgcccggc | 780 |
| tactactcca | agggcggagt | gcgcgtttga | | | | 810 |

<210> SEQ ID NO 2
<211> LENGTH: 1104
<212> TYPE: DNA
<213> ORGANISM: Guillardia theta

<400> SEQUENCE: 2

| | | | | | | |
|---|---|---|---|---|---|---|
| atgaaggtgg | atgtcgttca | ctgtgctggg | cacaagcgca | agctctgctc | gctggggacg | 60 |
| ggcgaggttg | tgcatgtctt | gaactttcgg | gcacatccgg | acaagacgca | ggagttcgag | 120 |
| aggatcgcgc | agaggctggc | ccactgcttc | taccacatgg | agtcggggat | cagcgacgta | 180 |
| cgggtctgcc | atcccaagtg | cggagaggta | tgcttcgtgc | tcacgttcct | cagcaagagc | 240 |
| gacctcgaga | ggttccaggc | cgggcccgag | cgcgacgcga | cggaggcgct | gaagtcatgc | 300 |
| atcgagggg | ggatcccctc | gttcgcggtg | tcggggacgc | tgatgccgga | tacgcacact | 360 |
| ttctcctccc | tcctcacgtt | cctcaaggcc | aacatcaagg | ggagcaacta | caacgcgcac | 420 |
| gactgcgagg | ttgtgaagcg | ggagatggcg | aagtggttcc | gaggaaggaa | ggagtacgag | 480 |
| aggtacgtgt | actgggaccc | tgccgacccc | accaagtaca | cgaggaatct | ggtgtttgcc | 540 |
| aatgagcaca | tggacgtcct | gctcatgtgc | tggccgcccc | actcgaagag | cgcgatccat | 600 |
| gggcacgagg | acagcagctg | ctgggtggtg | ctggtggagg | gcgaggtgca | cgagatccag | 660 |
| tacaacgtgc | cgaaactgga | caagaagttc | atcgagacgc | agatgaagaa | cccgacgggg | 720 |
| gcgatcggga | ggtgctcgaa | gctgcgggtg | atccacgagg | tgaagcttag | cgaagacggc | 780 |
| ctgaccaaca | cgtacgccaa | cgacgacatc | gccgtccacc | gcatcgagaa | caggtccgac | 840 |
| cggccggcct | tcacactgca | cgtgtatgcg | cccgggctga | ggaagatgaa | gatcttcaag | 900 |
| gacagcggcg | aggtgttcgt | ctactcggtc | gcttccatcc | cctacatgtc | cgagcatggc | 960 |
| agtcgcacgg | ggagatgggg | gaaagacacg | gaccctgacg | gcatcctcga | catcgaggcc | 1020 |

```
tggaacaaga accagctcgg cagctctcct gtcatctcct ccatgcccaa ccccccagac    1080
atggaagttg gtccttcgat ctga                                          1104

<210> SEQ ID NO 3
<211> LENGTH: 738
<212> TYPE: DNA
<213> ORGANISM: Candida tenuis

<400> SEQUENCE: 3
atgttatcta cccaaattcc cgcccaagga cctttatcgt cctcccatag tgctaggacc     60
agtgccaggg ccactcccac ggtggaagac cacgccaccc ccgctccgt ccccgactat    120 gacgccgaag aaattcccga taacaacttt ggccgcttga tccgcagcct caaggccgcc    180
ttaggcccta acaaaggttt gtcttgcaaa gacatcgata ttgaacacat caaatgcctc    240
atggaacaat acgaggcacg tgacgacgac tggctcaagt atgcgttgca cgacccatcc    300
cgtccctaca ccagaaatgg tatcatcaac ctcaacggta tgccaacct cttgatattg    360 tgctggtctc caggaaaagg aagtgccatc cacgaccatg ccaacgctca ctgctgcatg    420
aagattctta agggaaacct catggagagt ttgtacgaca tgccacaaac agagggtcag    480
ccattggtgt gcaagaaaga accgtgttg aagaaccaag aagttggata cattgccgac    540
gatattgggt tgcacaagat ttcgaatcca gacctggaag tgtctgtgtc gttgcactta    600
tacacgcctc cgtacgcatc gatgtatggg tgtagcatgt atgaagctgg aaatgggaag    660
aaacaccatg ttgatatgag taagtattat agttggcagg acaggtggt gagtgtgctg    720 ggagggctgt cgtgttag                                                 738

<210> SEQ ID NO 4
<211> LENGTH: 765
<212> TYPE: DNA
<213> ORGANISM: Fragilariopsis cylindrus

<400> SEQUENCE: 4
atgattgtgg cggcgaacac ctgcaaaggc aaagtgattc tgaaagcgat tgcgggcgcg     60
cgcaacaccg cggcggcggc ggcgaccgcg gcgtggtgga caacaaaaa aattaaaaac    120 aaaaacaaca gcaacagcaa ccgcattgcg accaccaaca ccaacaccaa aattcgccat    180
attcaggatt ttattaacga aattccggat gcggtgtatc gccgcaaaat tgaaaaaatt    240
gaaccgggcg cggtggatga tccggtggcg cgcctgtttc gccagagcga actgagcccg    300
accgatgatt ggctgaaata tgcgattttt aacgaagata aaccgtatac cgcaacctg    360 attagcaccg atcatgaaac ctataccctg ctgctgctgt gctggaaccc ggaacaggaa    420
agcccgattc atgatcatcc gagcgatggc tgctggctgc aggtgctgga aggcagcatt    480
aaagaagtgc gctatgataa agaactgaaa accattgcgg aactggaata taccatggc    540 gaactgagct atattaccga taacattggc tatcataaaa ttagcagcaa caacaaaaaa    600
cgcgcggtga ccctgcatct gtatgcgccg ccgtttgata cctgccattg ctggtatagc    660
gataccgcga acccgagcga accgtgcatt ggccatacca ttcatcatag cgaatatggc    720
gtggtgctgt tgaaagaaga agatgcgggc gatgatattg cggcg                   765

<210> SEQ ID NO 5
<211> LENGTH: 269
<212> TYPE: PRT
<213> ORGANISM: Chlamydomonas reinhardtii
```

<400> SEQUENCE: 5

```
Met Ser Ser Ile Ile Ala Met Pro Ile Asn Glu Asp Gly Val Val
1               5                   10                  15

Val Asp Arg Lys Leu Leu Gly Asn Glu Val Glu Ser Lys Ala Arg Cys
                20                  25                  30

Ala Asp Thr Ala Cys Thr Ala Ala Pro Ala Pro Ala Thr Ala
            35                  40                  45

Ala Ala Pro Thr Ser Met Pro Glu Leu Leu Gln Ala Leu Gln Arg Ala
        50                  55                  60

Ile Asp Glu Glu Lys Ala Thr Gly Gln Val Ala Ile Asn Ala Val Asp
65                  70                  75                  80

Gln Thr Pro Glu Ser Ala Ala Arg Leu Ser Ala Arg Val Gln Ala Leu
                85                  90                  95

Leu Ser Ala Tyr Thr Ser Ser Asn Ser Gly Asp Trp Arg Tyr Ala
                100                 105                 110

Met Phe Asn Asp Ile His Tyr Val Arg Asn Leu Val Asp Ala Asn Glu
            115                 120                 125

Asp Phe Glu Leu Ile Val Leu Cys Trp Lys Arg Gly Gln Val Ser Arg
    130                 135                 140

Val His Asn His Ala Asn Ala His Cys Trp Leu Ala Val Leu Asp Gly
145                 150                 155                 160

Glu Met Arg Glu Thr Gln Phe Gln Arg Ala Ser Ala Pro Pro Gly Cys
                165                 170                 175

Pro Ala Pro Ala Ala Ser Glu His Asp Gly Ser Thr Val Tyr Val Glu
            180                 185                 190

Pro Thr Gln Val Ser Asp Met Arg Val Gly Asp Ala Gly Tyr Ile Asn
        195                 200                 205

Asp Ser Met Ala Leu His Asn Val Gly Cys Cys Met Pro Ala Leu Ala
210                 215                 220

Ala Gly Glu Glu Gly Pro Glu Gly Gly Val Thr Leu His Cys Tyr Ala
225                 230                 235                 240

Pro Pro Ile Arg Arg Val Lys Ile Tyr Glu Asp Ser Lys Val Thr Glu
                245                 250                 255

Arg Val Pro Gly Tyr Tyr Ser Lys Gly Val Arg Val
            260                 265
```

<210> SEQ ID NO 6
<211> LENGTH: 367
<212> TYPE: PRT
<213> ORGANISM: Guillardia theta

<400> SEQUENCE: 6

```
Met Lys Val Asp Val Val His Cys Ala Gly His Lys Arg Lys Leu Cys
1               5                   10                  15

Ser Leu Gly Thr Gly Glu Val Val His Val Leu Asn Phe Arg Ala His
                20                  25                  30

Pro Asp Lys Thr Gln Glu Phe Glu Arg Ile Ala Gln Arg Leu Ala His
            35                  40                  45

Cys Phe Tyr His Met Glu Ser Gly Ile Ser Asp Val Arg Val Cys His
        50                  55                  60

Pro Lys Cys Gly Glu Val Cys Phe Val Leu Thr Phe Leu Ser Lys Ser
65                  70                  75                  80

Asp Leu Glu Arg Phe Gln Ala Gly Pro Glu Arg Asp Ala Thr Glu Ala
                85                  90                  95
```

```
Leu Lys Ser Cys Ile Glu Gly Gly Ile Pro Ser Phe Ala Val Ser Gly
            100                 105                 110

Thr Leu Met Pro Asp Thr His Thr Phe Ser Ser Leu Leu Thr Phe Leu
        115                 120                 125

Lys Ala Asn Ile Lys Gly Ser Asn Tyr Asn Ala His Asp Cys Glu Val
    130                 135                 140

Val Lys Arg Glu Met Ala Lys Trp Phe Pro Arg Lys Glu Glu Tyr Glu
145                 150                 155                 160

Arg Tyr Val Tyr Trp Asp Pro Ala Asp Pro Thr Lys Tyr Thr Arg Asn
                165                 170                 175

Leu Val Phe Ala Asn Glu His Met Asp Val Leu Leu Met Cys Trp Pro
            180                 185                 190

Pro His Ser Lys Ser Ala Ile His Gly His Glu Asp Ser Ser Cys Trp
        195                 200                 205

Val Val Leu Val Glu Gly Glu Val His Glu Ile Gln Tyr Asn Val Pro
    210                 215                 220

Lys Leu Asp Lys Lys Phe Ile Glu Thr Gln Met Lys Asn Pro Thr Gly
225                 230                 235                 240

Ala Ile Gly Arg Cys Ser Lys Leu Arg Val Ile His Glu Val Lys Leu
                245                 250                 255

Ser Glu Asp Gly Leu Thr Asn Thr Tyr Ala Asn Asp Ile Ala Val
            260                 265                 270

His Arg Ile Glu Asn Arg Ser Asp Arg Pro Ala Phe Thr Leu His Val
        275                 280                 285

Tyr Ala Pro Gly Leu Arg Lys Met Lys Ile Phe Lys Asp Ser Gly Glu
    290                 295                 300

Val Phe Val Tyr Ser Val Ala Ser Ile Pro Tyr Met Ser Glu His Gly
305                 310                 315                 320

Ser Arg Thr Gly Arg Trp Gly Lys Asp Thr Asp Pro Asp Gly Ile Leu
                325                 330                 335

Asp Ile Glu Ala Trp Asn Lys Asn Gln Leu Gly Ser Ser Pro Val Ile
            340                 345                 350

Ser Ser Met Pro Asn Pro Pro Asp Met Glu Val Gly Pro Ser Ile
        355                 360                 365

<210> SEQ ID NO 7
<211> LENGTH: 245
<212> TYPE: PRT
<213> ORGANISM: Candida tenuis

<400> SEQUENCE: 7

Met Leu Ser Thr Gln Ile Pro Ala Gln Gly Pro Leu Ser Ser His
1               5                   10                  15

Ser Ala Arg Thr Ser Ala Arg Ala Thr Pro Thr Val Glu Asp His Ala
                20                  25                  30

Thr Pro Arg Ser Val Pro Asp Tyr Asp Ala Glu Glu Ile Pro Asp Asn
            35                  40                  45

Asn Phe Gly Arg Leu Ile Arg Ser Leu Lys Ala Ala Leu Gly Pro Asn
        50                  55                  60

Lys Gly Leu Ser Cys Lys Asp Ile Asp Ile Glu His Ile Lys Cys Leu
65                  70                  75                  80

Met Glu Gln Tyr Glu Ala Arg Asp Asp Asp Trp Leu Lys Tyr Ala Leu
                85                  90                  95

His Asp Pro Ser Arg Pro Tyr Thr Arg Asn Gly Ile Ile Asn Leu Asn
            100                 105                 110
```

```
Gly Asn Ala Asn Leu Leu Ile Leu Cys Trp Ser Pro Gly Lys Gly Ser
            115                 120                 125
Ala Ile His Asp His Ala Asn Ala His Cys Cys Met Lys Ile Leu Lys
        130                 135                 140
Gly Asn Leu Met Glu Ser Leu Tyr Asp Met Pro Gln Thr Glu Gly Gln
145                 150                 155                 160
Pro Leu Val Cys Lys Lys Glu Thr Val Leu Lys Asn Gln Glu Val Gly
                165                 170                 175
Tyr Ile Ala Asp Asp Ile Gly Leu His Lys Ile Ser Asn Pro Asp Leu
            180                 185                 190
Glu Val Ser Val Ser Leu His Leu Tyr Thr Pro Pro Tyr Ala Ser Met
        195                 200                 205
Tyr Gly Cys Ser Met Tyr Glu Ala Gly Asn Gly Lys Lys His His Val
    210                 215                 220
Asp Met Ser Lys Tyr Tyr Ser Trp Gln Gly Gln Val Val Ser Val Leu
225                 230                 235                 240
Gly Gly Leu Ser Cys
            245

<210> SEQ ID NO 8
<211> LENGTH: 255
<212> TYPE: PRT
<213> ORGANISM: Fragilariopsis cylindrus

<400> SEQUENCE: 8

Met Ile Val Ala Ala Asn Thr Cys Lys Gly Lys Val Ile Leu Lys Ala
1               5                   10                  15
Ile Ala Gly Ala Arg Asn Thr Ala Ala Ala Ala Thr Ala Ala Ala Trp
            20                  25                  30
Trp Asn Asn Lys Lys Ile Lys Asn Lys Asn Asn Ser Asn Ser Asn Arg
        35                  40                  45
Ile Ala Thr Thr Asn Thr Asn Thr Lys Ile Arg His Ile Gln Asp Phe
    50                  55                  60
Ile Asn Glu Ile Pro Asp Ala Val Tyr Arg Arg Lys Ile Glu Lys Ile
65                  70                  75                  80
Glu Pro Gly Ala Val Asp Asp Pro Val Ala Arg Leu Phe Arg Gln Ser
                85                  90                  95
Glu Leu Ser Pro Thr Asp Asp Trp Leu Lys Tyr Ala Ile Phe Asn Glu
            100                 105                 110
Asp Lys Pro Tyr Thr Arg Asn Leu Ile Ser Thr Asp His Glu Thr Tyr
        115                 120                 125
Thr Leu Leu Leu Leu Cys Trp Asn Pro Glu Gln Glu Ser Pro Ile His
    130                 135                 140
Asp His Pro Ser Asp Gly Cys Trp Leu Gln Val Leu Glu Gly Ser Ile
145                 150                 155                 160
Lys Glu Val Arg Tyr Asp Lys Glu Leu Lys Thr Ile Ala Glu Leu Glu
                165                 170                 175
Tyr Asn His Gly Glu Leu Ser Tyr Ile Thr Asp Asn Ile Gly Tyr His
            180                 185                 190
Lys Ile Ser Ser Asn Asn Lys Lys Arg Ala Val Thr Leu His Leu Tyr
        195                 200                 205
Ala Pro Pro Phe Asp Thr Cys His Cys Trp Tyr Ser Asp Thr Ala Asn
    210                 215                 220
Pro Ser Glu Pro Cys Ile Gly His Thr Ile His His Ser Glu Tyr Gly
```

|   | 225 |   |   | 230 |   |   | 235 |   |   | 240 |   |

Val Val Leu Val Lys Glu Glu Asp Ala Gly Asp Asp Ile Ala Ala
                245                 250                 255

<210> SEQ ID NO 9
<211> LENGTH: 2958
<212> TYPE: DNA
<213> ORGANISM: Micromonas pusilla

<400> SEQUENCE: 9

```
atgtccgcgg cgacgggatc attatcccta cccctactcg ggcatctcgc gacctcgcgt    60
aacgcacgcg cgcgtcggaa ccgcgccgcc gcggccatcc ccggcgtctc cctcgggaaa   120
tcgacctcgg ttttcactcc gcgaggtcct aagcgcatcg cgcgcgtcgt cacctcgaag   180
gcgggccccgc attcgaaccc tccgagggcg atatcgaccg tcgacgacgt cctcgcgttc   240
accgtgccca ccgacgagcc cgcggccgag accgcctccc ccgccgacag cgactgcgaa   300
ggcgagttct gcgacatgaa ggagagctcg tgcacgacga gggacctcat cggcagcacg   360
ccgctgctcg atctgagcgc gtactccctg aaccccaccg tgaagatcct cgcgaagtgc   420
gagtacctca acccgtccgg gtccatcaaa accgcatcg cgacgcacat cctggacaag   480
gcgatcaaga gcggcgatct caagcccggg atgaccgtcg tcgcggcgac gtccgggaac   540
accggcgccg cgatcgcgat ggcgtgcgcg ttgcgcgggt acgactacat cgtcatcacc   600
aacgagaaga cgtccaagga aaggtggac gcgatgagag cgtacggcgg cgaggtgatc   660
gtctccccgt ccggggtgtc cccggacgac ccacagcact accagaacat cgagaacaag   720
ctgtgcgagg agaaccccgg gacgtactac ggcgtggatc agtataacaa cccgtacaac   780
gcggacgcgt acgaggcgac gctcgggccg gagatttggc gtcagagcgt gggcgcggtg   840
acgcacttca tcgtcggcgg cagcaccggc ggcacggtca cggcacgggt gaggtacttg   900
aagcaagaga acccggacgt gaggatcgtc ctcgcggacc cgagagggag cgtgttctgg   960
gaccacgtcg tcaacggcgt cgccgccgac gacgtcaagg tgtccaagtc gtgggagacg  1020
gagggcgtcg gcaaggattc catccccggg tgcctcgacg tctcgatcgt ggacgggatg  1080
gtgcgcgcga cggacgagca ggcgttcggc gtgtgccgcg agctcgcgag cagcgacggc  1140
ctcctcgtcg gcggcagcag cggtctgaac ctccacgcct cgcgcgtgtt atccggcgac  1200
gtcgcggacg acagcgtcat cgtcacggtg ttcccggaca cggcgtgaa gtacctgtcg  1260
aagatttaca cgacgactg gctcgactcg aagaagatgg gcggcgcaaa gaactcggac  1320
gggaacgcgg agagagccgc ggagtgcgag gtgtactggc gcccggacgc gctctcgttc  1380
gcggagcgaa aggcggcggc ggacgccgcc gccgccgccg ccgtcgaggg cgacaacctc  1440
tggcccgagg acgagaccga gcgcgagctc aagttcctgg aggaactcgc gccgaagctg  1500
acgcagtacc acagagactc catcaagggc gacgagcgcg tgcacagcaa gctccagtcc  1560
ccggaggagc tcgcggcgac gttcgccgcc gggggcgc ccatcgacct cgcggaggg    1620
gacgccccgg cgacggagga gcaactcgcg ctcgcggtgc aggcggtcat ggacaactcg  1680
gtccgctcct cgcacccgat gttcttgaac cagctgtacg ccggcgtcga cgtcgtcgcg  1740
ctcgcggggg agtggaccgc gagcgcgttg aacgccaacg tgcacacgtt tgaagtcgcg  1800
ccggtgctca cggagattga aaagccgtc ctcgcgaaaa ccgcgcggat gtggctgaac  1860
aagcccgggt ctaagacgac gccgccgcac gacggtctgc tcgtcccccgg cgggtccctg  1920
gcgaacatgt actcgatgat cctcgcgcgc gatcgcgcgg agccggaggc gaagaccaag  1980
```

```
ggcgcgagcg gcaacctcgt cgcgttttgc tcggagcagt cgcactactc gtacaaaaag    2040
tccgcgatgg tcatgggcct cgggatggac aacatgatca aggtgaagtg cgaccagtcc    2100
ggcgcgatga tcccggcgga gctcgagaag gcggttcagg aggccaagtc ccggggcaag    2160
gtgccgttct acgtcggcac caccgcgggg tccaccgtgc tcggcgcctt tgacgactac    2220
gaaggctgcg cggacgtctg cgaaaagcac gacatgtgga tgcacgtcga cggcgcgtgg    2280
ggcggcgccg cggcgctgtc cccgacgaga aggcacaatc tccagggcgc gaacagagcg    2340
gactcgttct gctggaaccc gcacaagatg ctcgggttgc cgctccagtg ctccatcttc    2400
gtgacgaagc aacccggggc gctgtccaag gcgaacgccg cgcaggcgga ctacttgttc    2460
cagccggaca agaacaacgc cgccgcggac ctcggcgacc gcacgattca gtgcggacgc    2520
aaggcggacg ccctcaagat ctggctcgcg tggaaggcgc gcggagacga aggctgggcg    2580
aatctcgtgg accgctcctt tggcctcgcg gagtacgtcg aggcgtcggt gcgcgagcgg    2640
tgcgaaaaag acggctcgtt cgtcctcgcc gcgcccgcgc agtgcgcgaa catcgggttc    2700
tggtacgtgc cccgcgcct gaggccgttc gatgtcgagt ccgcgaccgc ggaccagctc    2760
acggagattg ggttcgtcgc cccgaagctg aaggaccgga tgcaacggac cggggacgcg    2820
atgatcgggt tccagccgat cgactcgatg aaccttccaa acttttttccg actcgtgctt    2880 ccaaactcga ggcacctgtc gaagaacgcg ctcgacgcta tgctcgatcg catggacgac    2940
atgggcaaag acctgtga                                                  2958
```

<210> SEQ ID NO 10
<211> LENGTH: 2792
<212> TYPE: DNA
<213> ORGANISM: Ostreococcus tauri

<400> SEQUENCE: 10

```
atgcggacat acacccgatc ttccgagggt ccccgcccat tccacgagag cgcgccgtcg     60
ccagtgcgcg cctccccagt acgcgcgcc gttcacatcg ccgacgcgag cgccggtgct    120
gtcacttccg atcactaccg gcgcgctcgc tcgaacggcg ccgcgcgcgc cgtgcgcggc    180
gccgacgaga cgtcgtcttc aggtttgat tcaacagagg cgtcgctcga gtccgtcgac    240
gacgccctcg agagcgatct ccagcgacgc cgacgacctg gaggagctcc tgaacttaga    300
ttacccggtg gacatgccgg agttcgagaa cgcgctgccg acgatgttca cgaacgggaa    360
gacggtggac gatgagaagc actggcggtc gacgcacgcg cgaatcgcaa acggagcggt    420
ggtgccacag cagctcatcg gtgggacgcc gatgatcgat cttagtgagt ttagtgcgaa    480
cccaaaggtg aagatctatg ggaagtgcga gtacatgaat ccgagtggga gcattaaaga    540
tcggattgcg caggagattt tgactcgggc gctggacg ggcgagttga aacccgggat    600
gacggtcgtg gcggcaacga gtgggaacac cggggcggcg atcgcgatgg cgtgcgcgat    660
tcgtgggttt gattacatcg tgatcacgaa taagaagacg agtaaggaga gattgacgc    720 catgaaggcg tacgggggcc aagtcatcgt cgcggagagt ggggtcccgg cagatcatcc    780
ggatcattat cagaacatcg agacgacgat gtgcgcgcag aacccgaact attacggcgt    840
aaatcagtac gataatccgt acaacgcgga tgcgtacgag aagactcttg gtcccgagat    900
ttggtcgcaa accaaggggg cagtgacgca cttcatcgcg ggcggttcca caggaggcac    960
catcactggt accggtcgct acttgaagag cgtagatcca acgatcaaaa tcatgttagc   1020
tgatcccaag ggtagcgttt tgtgggacta tttcgtcaat gacgtgcccg aagaggatct   1080
tgtggcgaag agttgggaag tcgagggcgt cggcaaggac tccattccgg gtgttttgca   1140
```

```
gacagaatac atcgacggtg ccgtgaaagg ttgcgacgcg agctcattcc gaatttgccg   1200
aatggtggcc gaatcttcgg gcatcttgct cggcggtagc tccggtctga acctgcacgc   1260
cgctcgagtg ctctcgagcc agatcaagga gggtgttata gtcacggttt tgtgcgacag   1320
cggtgtcaag tatttgtcaa agatcttcaa cgacgaatgg ctcgaatcga agaatttgaa   1380
tcagccattg tcggatgtca agaacttcca agtcgcttgg aaaaaggacc agtctgaggc   1440
gagtgacgac gaagacgcag accacggtct gtggagtcgc gacgatgagg agaaggagct   1500
tcgctttcta gacgaaatcg cgacgcacat ggttgagtac taccgcaact ccgcgcgcgc   1560
cgccgacccg gtcagtacgt acaactctcc gctcgccctt cacgaaaagt tcaaggaggt   1620
gggtattccg ttggccatcg gtacgggtga ggagccggtc tcgatgagct tactcaccac   1680
cgcgatgaac acggtgatcc agaacagcgc tcgcacctcg cacccaatgt taggaggaac   1740
gcgcggagga agagacggag gaagtagagg agatcgtcgt cgatggcccg ccgggaggga   1800
tgaggcggat gggtgagttg tcgtgggagc tcggggcggc gggtgaggag gaggaggagg   1860
aagagcaggg gcaggagggc gaggaaatct ctcgagagga ggtgctggcg ctctcggtgg   1920
agctcatcga atccatcgct tccgggaagg aaccgctcga tgcggcgcgt cttgggagct   1980
tgctttggac tttgagcaac gcgctgttgg aggatttgac ggacagggac gatttacgcg   2040
ttccggggaa ctcgctcgag acgtttccgg tggagctggt gcgaaacgtc atgggcgccg   2100
tcgaaaccct ggtcgttgcg ctgacgttcg agccggaaga tgcggtgacg caacgaagtg   2160
ggcacgcaat tccggccatc ggcacacatc gcgtcgctgc ggcggagatc atcgccgtgc   2220
tcttgcaaat cgggtgccaa gacattgacg agcgcatcgc aaagctcaag ctgccgaacg   2280
acggtcagtt cgtcctcgtg tcgctcgtac gcatgttttt caagtattct tggagttcgg   2340
cgctgcacgc gaccgtggtg agactgatct tggccgcgct ggtgagccca cacgagccgc   2400
tctgggcacc catgtttgag ggcggggacg agagtcttca gggctctctg gcagcgtcca   2460
tgaagacggc gctcgcgacg aagcccatct ccacgagaga cggtaacgtc gggagcgtga   2520
ttattctcgc caacgctctg cacgagctcg aaacttgcga tgacgtcgag cgccagagcg   2580
tgcggacgac gttgcaggag gatgcaacgt ggcgagccgc cattgacggt gaggatagcc   2640
cgttggcgaa cctcaacaac gaacaggctg gcggactttg tggaccaaag ccgcagaagt   2700
cgcctgtttt catggactcc ggcatgggcg ccaacgtcat cagcagccaa gagctgctca   2760
ggatgttgca gcacatctcg cttggtcaat ga                                2792

<210> SEQ ID NO 11
<211> LENGTH: 1629
<212> TYPE: DNA
<213> ORGANISM: Guillardia theta

<400> SEQUENCE: 11
atggtgcccc ccgccttgca tgaagggttc tgcagccctc gaggcaggac ttgttgctct     60
caggtgggac acgtggagtt gttggagagc tgggaaacgc agggggaacaa gctgagatgc   120 gagcaagacc tcctgctggc caaggttccc tctcgcttcc accaccttga ggaagtggcc   180
gagctggatg atatcttcag ggaggtgtat cctctgatcc ggcagtacga gacggagaac   240
gcgctagcag acgagcacaa ggtgctggag ttcaggacgc cagcggagct gaaggaggag   300
gtggacgtgg ggctgcctga ggagggatct gtggagaaat ttgtcgaggg atgcagaagc   360
tctatgaagt acagcgtccg aacgagtcac ccgcgcttca tgaaccagct ctatgctggc   420
```

| | |
|---|---|
| agcgacccgg cagggcaggt ggcagagctg ctcagtgctg tgctgaacac caccatccac | 480 |
| acgtacgggg cagctccctt cttctccgtg ctggagcggc aggtgatcga gaagctgggg | 540 |
| aggatgctgg ggtttcagga gcatgtcgac ggcgtctttg cccccggagg ctcgtacgcg | 600 |
| aacatggtgg cgctgatagt tgcgaggaac cagcacttcc ctcatgtgcg ggagcatggc | 660 |
| tggaggagcg acgacaaacc tgttatcttc acttcttccc atgctcacta ctctgtcgcc | 720 |
| aaggctgcca tgatcacggg gatggggtcg aatcaagtgg tcgctgtgcc tacgacgag | 780 |
| cagggaagaa tgcagcctgc agcgctggag gaggagatta tgcgagcaaa ggagagcgga | 840 |
| cggaagcctt tctacgtgag ctgcacggca gggacgacag tgactggggc gtttgacccg | 900 |
| attgacgaga tctgtcagat atgtagaagg catgagatgt ggctgcacac ggatggcgcg | 960 |
| tgggaggag ctgcaatatt ctcggaggag cacagaaatc ttctacgagg agttgagggc | 1020 |
| gtcgatagct tctgcttgaa tccgcacaag atgctggggg tcccgatgca gtgctccgtg | 1080 |
| ctcatcctca caaccacga ggggcgctcg agaggagcaa cagaggaaga gagcttggat | 1140 |
| ctcgggcaga agtcgctgca gtgcggaagg aaacctgatt gcctaaagct ctggctctgc | 1200 |
| tggaagcgac atggaacccg cgggtttgca aggagggtag atcgcgcgta taccttctcg | 1260 |
| cagaagttcg cagaaatggt cagaagggac cccaggttct acctgctgat ggacccgatc | 1320 |
| tcctgcaacg tctgcttctt ctacctccct ccctccctcc ggcagcagct ggtggacaga | 1380 |
| aacctcaacg acttggaaaa ggaggaggcg cagcggcagc tcaaggagtt ccatgctcga | 1440 |
| ctcggtcagg ttactcagat catctacagg aggatgcaga agacggcaa gatgctcatc | 1500 |
| aacttcagcc ctcttaaaga cagagatctg cctcacttct tccgagccgt catgatccag | 1560 |
| cagagagtaa cggaagacga tcttgttttc atcctcgatc attttgaaca tctgggaaag | 1620 |
| gacctctag | 1629 |

<210> SEQ ID NO 12
<211> LENGTH: 1515
<212> TYPE: DNA
<213> ORGANISM: Candida tenuis

<400> SEQUENCE: 12

| | |
|---|---|
| atgtctcttc aaacaccttt agaaactaat agagcaaccg agctcgatcg gttgttggca | 60 |
| cttgtgacac ccaagatcct ccagcatatc gaggagtcgg accccagttc tctgaacttc | 120 |
| aaacaaaacg ccctcggaca atacagatca ccagctgagg tgaagagcca tttgctcag | 180 |
| tttaacagcg actttgagcc catcaagaac gatgagcaaa actccagca cttgatcaac | 240 |
| tcggtgttgg atgtgctggt gaatacatgg aatccaggtt ttttggataa actctacgcg | 300 |
| tccaataatc ccattggcgt gatttcagac ctcattttat cggtattaaa caccaattca | 360 |
| cacgtttta cggtgtcgcc ggtgctctca gtgctcgaga actacgtggc ccgcgagtac | 420 |
| gggcggcttt ttttaagga ccaccaggac acctgtggtg ggttgacctt cagcggaggg | 480 |
| tcttggtcca acatcacatc gttgcagatg gcgcggcgt tgctctatcc tgacaccaag | 540 |
| atccagggaa atggcctgca ccggttcgcg gtgtacacat cgaaacactg ccattactcg | 600 |
| gtggaaaaag ccgctattct tctcgggctc gggtctggca gtgtgttcaa agttgctgtc | 660 |
| aacgacgacg ggacaatgca ccacgagagc ctcgaggcag caatcaccga ctctattgcc | 720 |
| caagggttca cgccgttata tatcaatgcc accgccggta ctacagtatt tgggtcgttc | 780 |
| gatgcgtttg cacccatttc ccgcatcgcc caaaagtacc gcgtgtggtt ccacatcgac | 840 |
| ggatcgtggg gcggtaacgt ggtgtttttcg cgccgccacc gccaccgcct cgacgggtgc | 900 |

-continued

```
cacacggccg actccatcac tgttaacccc cacaaaatgc tagggGtgcc aaccacatgc    960
tcatttcttc tcgtgccaca tgtgggtaag ttccagcagg ccatgtcact agacgccccg   1020
tacctcttcc acggcagaga aagtgatgag gagaactttg atctcgcgga cggtactatg   1080
gggtgcggcc gccgcgctga ctcgttcaag ttgtacatgg cctggaagta ctatggcacc   1140
cgcggcttcg agcagagggt cgatcacgcg tacgacacgg tgcggtactt tttgcaggcg   1200
acccgccaac atcccaactt cgcagtagtg ggagatcccg cgtgtttgca agtgtgcttt   1260
tactaccgtc ccaaatccta tgagggagat gatctcaccc ccgtcactag gtatatttca   1320
cgagaattgc acacccaggg tcgataccct gttgacttct cacctcaccc acaggcgggg   1380
gcccaggatg aacagggtga gtttttttcgg gtggtattta actcgcccat ccttacggat   1440
gccattattg atgatcttgt gactgctatt gtcaaagctg gggaagcgtt cgaacgcgac   1500
cagaggaaaa tctaa                                                    1515

<210> SEQ ID NO 13
<211> LENGTH: 1833
<212> TYPE: DNA
<213> ORGANISM: Cyanidioschyzon merolae

<400> SEQUENCE: 13
atggaaaccc ggaatgctcc cggtagtgcg accaacaaac taaaagaagt gggttttggg     60
ggtgagatag agtttgcgcg agagctccag gaactgctcg ggatcgtcga gcgaaaactg    120
ggactctgca cgtcaagcga cgcgggcagt gaaaatggtg tggaacggac acccgaggcg    180
cagttgccgc tcgtgtacgt accaccaagt gctatttggc gacagcttga tcactatgta    240
caatgtgtta tcagcgggga gagtgcaggt tcgcgcgact tgctggaaca gtttctcgaa    300
gaccttcttc ggtattcggt acggacgaag cacgccttct ttttgcaccg tctctacggc    360
ggctcggatc cagtaggaca aatagctgac ctcatctgct cggtgttaaa caactctgcg    420
gatacgtttt ccgctgcgcc gtatctggtg cttctcgaac gacgggttat tgaagcgctg    480
agttcgtgca tcggctggaa gacaccgctg cagggtgatg gtatcttctg tcctggcggc    540
agctatgcga accttattgc actgacgaca gcgcgccacg tgtttcaaat gaatgccagg    600
cgaccgcaga caaagcgtac ccagcgccat cactgcaacg agcggcgaat ggggatcttc    660
acgtcggtcc aaggccacta cagcgttcga cggaatgcgg ccatgctcgg ttctgtgat    720 gcacccggtg aggactgctc ggatgtcgtg ctggtgcccT gtgacagcca aggccgcatg    780
gacccggagg cgttgcgtcg actcattcac tgctttcgca cacccggcc gctttccagc    840 gtattcgtga acgtgacagc gggtacgact gttttgagtg cgttcgaccc tctgcccgaa    900
atctggacag ttctggcaga ggcatttcca ttgaattccg tagagtcagc gtcagcagag    960
ctggaacagc gccttgaggc agacaccatg attcgggagc gcttgcctca gccgacgttt   1020
tgggtgcacg tggacggagc cttaggcggc tcttTcttat tttcggagag atttcgtccg   1080
gtggcgctgg ctgggcttga aaaatacgca aattcgttTg tgctgaatgc tcataagcta   1140
ctcaatgcac cgctgcagtg ctcgattctg ttagttcggg agcgcggttT gcttcaggcc   1200
gcgcacgctg cgcgagcacc gtatctgttt cacgacgacc tcgataccga tgcgcagtac   1260
gatattggcg acatgacgct gacgtgtagc cgccgctctg atgcgctcaa gttctggctg   1320
atgtggatgt ggcgtggcag tgctggtttc ggggcccgcg tggaagccgc tgctcgcaac   1380
gcacgcgcta ttgctgaggc catggcgaag cgaccgtgct tcctcctggt acactggccg   1440
```

| | |
|---|---:|
| cttgatcggt cttatcctgc gacgaatgtt tgcttttatt acctgccatc ggacatgcga | 1500 |
| gaaagcattc ggaacctggc agacatcaag gcggaaacag ccgctcagct gctgggtagc | 1560 |
| atcagcgtcc ggctgtgtcg agcgctgcag gtcagcggca aggccttgct gaactactgc | 1620 |
| acgctcgaag gcacagattt gccgattttt ttgcgccttg ccctgcatgg tcttcacgta | 1680 |
| tacgaagagc aggaaattca agatctcctg aaccgcattg aagactgtgg cgatcacgca | 1740 |
| atccgtcccg gtacaccagc gagcatcagc ggcaacgtca gcggcggagt gtcgcccgta | 1800 |
| ggcgacgacg gcgctcataa tgccgtcctc tag | 1833 |

<210> SEQ ID NO 14
<211> LENGTH: 2052
<212> TYPE: DNA
<213> ORGANISM: Thalassiosira oceanica

<400> SEQUENCE: 14

| | |
|---|---:|
| atgggacgga ggaagtcaaa catgtcacgt tcaccttctt ctctgctctg tccaccgtgg | 60 |
| gccgacgggg tcgtaacccc gctacactgg ggagcgctga tcgcgattgc tgctacaatt | 120 |
| ttttctttgg gtacgctggt gggttacaac ttgggaagaa aaggcgcgg gcggccaacg | 180 |
| aaaacgaaag ggagcgcaaa gcacgatggg gttcggccca cgggtcgctt gccgaagaga | 240 |
| aagaacatac acagcctcga tgggtcaact atggtcctaa atggctcgct agaactaatg | 300 |
| gcgtctaagt ggggaggga cgagttccaa atccgcggg aagtggccgt ggtggagtat | 360 |
| ctatcgccag aggaaatgtc gcggatgctc ttcaaatcag tgaccgaaca cagctctgac | 420 |
| agcacactga gcttggatga gacgatagac gacctctcgc cgaaatcgag tgccacagac | 480 |
| ctaactagtc tagtgccaac tttcgacaaa agccgaagca ttccgacgga acccgaaaag | 540 |
| ttcatcgagc tgcttggtct aattcagaag tacagcgtga acacttcgca tccctacttt | 600 |
| ttcaatcaac tgttcggctc gctagatccc attgcactgg cggcagaaat cgtggccctt | 660 |
| tcggtcaaca cgtctgttta cacgtacgag actgctccag tctttagtct aatcgaacgt | 720 |
| gaggtcatgg gccaaattgg gaagttggtt tcgggccaa catcaggtaa acaaatatca | 780 |
| ttcgaatccg acgacaagtt cgagggcgaa ggattgatga ttccaggtgg ctcattggca | 840 |
| aacttaacag ccatgcatgc tgcaagacat cgttggaaag tgatgaatgg tttcatcaaa | 900 |
| caagccaccg aggacaccga gcaaatgctg ggtacggact ggtcaacatt cggcgaagaa | 960 |
| aagaagtcag atgacgtctt tccaacaact gctaagatgc aaggagaaga caccgaaaca | 1020 |
| ggggagaccc tgtgcgacta catccgatcg gtgccagacc tggtagcatt tgtctcgagt | 1080 |
| gaggcgcatt attccttttc caagtcagca cgtgtgctgg ccttcgaga ggatgatcta | 1140 |
| gtgatcattc ctacccaccc cgacggaaga atgaatgtac atgagctgtc aaagcgaata | 1200 |
| gaagaaatag agttagaatc ggcatcgcat atggacgcaa gaataagggt gccattcttc | 1260 |
| gttgcatgta cggcaggtag tacggtccgc ggttcatttg acgagattga agagatagtc | 1320 |
| aaagtctgcc gcaggtacga agctcgggcc aaatcatcag aagcacgctc gatctgggtc | 1380 |
| cacgttgacg gtgcttgggg gggctctgct atgttttcct cgcggcggca tattcgcgac | 1440 |
| ataactcaca tggatgagat ccgccacgcg gactcgttca cgttcaaccc tcacaagatg | 1500 |
| ctgggagccc ctcagcaaac aacggcattc atcgtacgac accgccacgc gctcaagcgc | 1560 |
| gccaactctg ccggggccaa atatctcttt gacccacgaa agaatggagc tgagtacgat | 1620 |
| ctaggagact tgtcgtatac gtgcggtaga cgcacggatg ccgttaagct gtgggcgatg | 1680 |
| tggaaatact acggaaagtc cggccttggc gaacgagtag accagaaggt tgatgaactg | 1740 |

-continued

```
cagcttttg tagatgagtt gcggggccgt ccatcttttg ctttggcatg tgcgccctgg    1800
ccgttcaacg tcaatttttc tacttccctc caaggatacg agcgattctg gaggctcgcg    1860
gacatgtcaa atgtttcggt gcaacttaag ttgcgtttgc acgaggcggg cgagatgata    1920
attccctacc agcctctgac taaccagaaa gccgactgct tccgacttgt gttggctggc    1980
aagaaagatt tcggtcttgg agacatgcgc cacatactag acacaatgga gaggtatggg    2040
agggacctat ag                                                        2052

<210> SEQ ID NO 15
<211> LENGTH: 985
<212> TYPE: PRT
<213> ORGANISM: Micromonas pusilla

<400> SEQUENCE: 15

Met Ser Ala Ala Thr Gly Ser Leu Ser Leu Pro Leu Leu Gly His Leu
1               5                   10                  15

Ala Thr Ser Arg Asn Ala Arg Ala Arg Arg Asn Arg Ala Ala Ala Ala
            20                  25                  30

Ile Pro Gly Val Ser Leu Gly Lys Ser Thr Ser Val Phe Thr Pro Arg
        35                  40                  45

Gly Pro Lys Arg Ile Ala Arg Val Val Thr Ser Lys Ala Gly Pro His
    50                  55                  60

Ser Asn Pro Pro Arg Ala Ile Ser Thr Val Asp Asp Val Leu Ala Phe
65                  70                  75                  80

Thr Val Pro Thr Asp Glu Pro Ala Ala Glu Thr Ala Ser Pro Ala Asp
                85                  90                  95

Ser Asp Cys Glu Gly Glu Phe Cys Asp Met Lys Glu Ser Ser Cys Thr
            100                 105                 110

Thr Arg Asp Leu Ile Gly Ser Thr Pro Leu Leu Asp Leu Ser Ala Tyr
        115                 120                 125

Ser Leu Asn Pro Thr Val Lys Ile Leu Ala Lys Cys Glu Tyr Leu Asn
    130                 135                 140

Pro Ser Gly Ser Ile Lys Asp Arg Ile Ala Thr His Ile Leu Asp Lys
145                 150                 155                 160

Ala Ile Lys Ser Gly Asp Leu Lys Pro Gly Met Thr Val Val Ala Ala
                165                 170                 175

Thr Ser Gly Asn Thr Gly Ala Ala Ile Ala Met Ala Cys Ala Leu Arg
            180                 185                 190

Gly Tyr Asp Tyr Ile Val Ile Thr Asn Glu Lys Thr Ser Lys Glu Lys
        195                 200                 205

Val Asp Ala Met Arg Ala Tyr Gly Gly Glu Val Ile Val Ser Pro Ser
    210                 215                 220

Gly Val Ser Pro Asp Asp Pro Gln His Tyr Gln Asn Ile Glu Asn Lys
225                 230                 235                 240

Leu Cys Glu Glu Asn Pro Gly Tyr Tyr Gly Val Asp Gln Tyr Asn
                245                 250                 255

Asn Pro Tyr Asn Ala Asp Ala Tyr Glu Ala Thr Leu Gly Pro Glu Ile
            260                 265                 270

Trp Arg Gln Ser Val Gly Ala Val Thr His Phe Ile Val Gly Gly Ser
        275                 280                 285

Thr Gly Gly Thr Val Ser Gly Thr Gly Arg Tyr Leu Lys Gln Glu Asn
    290                 295                 300

Pro Asp Val Arg Ile Val Leu Ala Asp Pro Arg Gly Ser Val Phe Trp
```

-continued

```
            305                 310                 315                 320
        Asp His Val Val Asn Gly Val Ala Ala Asp Val Lys Val Ser Lys
                        325                 330                 335
        Ser Trp Glu Thr Glu Gly Val Gly Lys Asp Ser Ile Pro Gly Cys Leu
                        340                 345                 350
        Asp Val Ser Ile Val Asp Gly Met Val Arg Ala Thr Asp Glu Gln Ala
                        355                 360                 365
        Phe Gly Val Cys Arg Glu Leu Ala Ser Ser Asp Gly Leu Leu Val Gly
                        370                 375                 380
        Gly Ser Ser Gly Leu Asn Leu His Ala Ser Arg Val Leu Ser Gly Asp
        385                 390                 395                 400
        Val Ala Asp Asp Ser Val Ile Val Thr Val Phe Pro Asp Asn Gly Val
                        405                 410                 415
        Lys Tyr Leu Ser Lys Ile Tyr Asn Asp Asp Trp Leu Asp Ser Lys Lys
                        420                 425                 430
        Met Gly Gly Ala Lys Asn Ser Asp Gly Asn Ala Glu Arg Ala Ala Glu
                        435                 440                 445
        Cys Glu Val Tyr Trp Arg Pro Asp Ala Leu Ser Phe Ala Glu Arg Lys
                        450                 455                 460
        Ala Ala Ala Asp Ala Ala Ala Ala Ala Val Glu Gly Asp Asn Leu
        465                 470                 475                 480
        Trp Pro Glu Asp Glu Thr Glu Arg Glu Leu Lys Phe Leu Glu Glu Leu
                        485                 490                 495
        Ala Pro Lys Leu Thr Gln Tyr His Arg Asp Ser Ile Lys Gly Asp Glu
                        500                 505                 510
        Arg Val His Ser Lys Leu Gln Ser Pro Glu Glu Leu Ala Ala Thr Phe
                        515                 520                 525
        Ala Ala Ala Gly Ala Pro Ile Asp Leu Ala Glu Gly Asp Ala Pro Ala
                        530                 535                 540
        Thr Glu Glu Gln Leu Ala Leu Ala Val Gln Ala Val Met Asp Asn Ser
        545                 550                 555                 560
        Val Arg Ser Ser His Pro Met Phe Leu Asn Gln Leu Tyr Ala Gly Val
                        565                 570                 575
        Asp Val Val Ala Leu Ala Gly Glu Trp Thr Ala Ser Ala Leu Asn Ala
                        580                 585                 590
        Asn Val His Thr Phe Glu Val Ala Pro Val Leu Thr Glu Ile Glu Lys
                        595                 600                 605
        Ala Val Leu Ala Lys Thr Ala Arg Met Trp Leu Asn Lys Pro Gly Ser
                        610                 615                 620
        Lys Thr Thr Pro Pro His Asp Gly Leu Leu Val Pro Gly Gly Ser Leu
        625                 630                 635                 640
        Ala Asn Met Tyr Ser Met Ile Leu Ala Arg Asp Arg Ala Glu Pro Glu
                        645                 650                 655
        Ala Lys Thr Lys Gly Ala Ser Gly Asn Leu Val Ala Phe Cys Ser Glu
                        660                 665                 670
        Gln Ser His Tyr Ser Tyr Lys Lys Ser Ala Met Val Met Gly Leu Gly
                        675                 680                 685
        Met Asp Asn Met Ile Lys Val Lys Cys Asp Gln Ser Gly Ala Met Ile
                        690                 695                 700
        Pro Ala Glu Leu Glu Lys Ala Val Gln Glu Ala Lys Ser Arg Gly Lys
        705                 710                 715                 720
        Val Pro Phe Tyr Val Gly Thr Thr Ala Gly Ser Thr Val Leu Gly Ala
                        725                 730                 735
```

```
Phe Asp Asp Tyr Glu Gly Cys Ala Asp Val Cys Glu Lys His Asp Met
                740                 745                 750

Trp Met His Val Asp Gly Ala Trp Gly Ala Ala Ala Leu Ser Pro
        755                 760                 765

Thr Arg Arg His Asn Leu Gln Gly Ala Asn Arg Ala Asp Ser Phe Cys
770                 775                 780

Trp Asn Pro His Lys Met Leu Gly Leu Pro Leu Gln Cys Ser Ile Phe
785                 790                 795                 800

Val Thr Lys Gln Pro Gly Ala Leu Ser Lys Ala Asn Ala Ala Gln Ala
                805                 810                 815

Asp Tyr Leu Phe Gln Pro Asp Lys Asn Asn Ala Ala Asp Leu Gly
                820                 825                 830

Asp Arg Thr Ile Gln Cys Gly Arg Lys Ala Asp Ala Leu Lys Ile Trp
                835                 840                 845

Leu Ala Trp Lys Ala Arg Gly Asp Glu Gly Trp Ala Asn Leu Val Asp
850                 855                 860

Arg Ser Phe Gly Leu Ala Glu Tyr Val Glu Ala Ser Val Arg Glu Arg
865                 870                 875                 880

Cys Glu Lys Asp Gly Ser Phe Val Leu Ala Ala Pro Ala Gln Cys Ala
                885                 890                 895

Asn Ile Gly Phe Trp Tyr Val Pro Pro Arg Leu Arg Pro Phe Asp Val
                900                 905                 910

Glu Ser Ala Thr Ala Asp Gln Leu Thr Glu Ile Gly Phe Val Ala Pro
                915                 920                 925

Lys Leu Lys Asp Arg Met Gln Arg Thr Gly Asp Ala Met Ile Gly Phe
                930                 935                 940

Gln Pro Ile Asp Ser Met Asn Leu Pro Asn Phe Phe Arg Leu Val Leu
945                 950                 955                 960

Pro Asn Ser Arg His Leu Ser Lys Asn Ala Leu Asp Ala Met Leu Asp
                965                 970                 975

Arg Met Asp Asp Met Gly Lys Asp Leu
                980                 985

<210> SEQ ID NO 16
<211> LENGTH: 908
<212> TYPE: PRT
<213> ORGANISM: Ostreococcus tauri

<400> SEQUENCE: 16

Met Arg Thr Tyr Thr Arg Ser Ser Glu Gly Pro Arg Pro Phe His Glu
1               5                   10                  15

Ser Ala Pro Ser Pro Val Arg Ala Ser Pro Val Arg Arg Ala Val His
                20                  25                  30

Ile Ala Asp Ala Ser Ala Gly Ala Val Thr Ser Asp His Tyr Arg Arg
                35                  40                  45

Ala Arg Ser Asn Gly Ala Ala Arg Ala Val Arg Gly Ala Asp Glu Thr
            50                  55                  60

Ser Ser Ser Gly Phe Asp Ser Thr Glu Ala Ser Leu Glu Ser Val Asp
65              70                  75                  80

Asp Ala Leu Glu Ser Asp Leu Gln Arg Arg Arg Pro Gly Gly Ala
                85                  90                  95

Pro Glu Leu Arg Leu Pro Gly Gly His Ala Gly Val Arg Glu Arg Ala
                100                 105                 110

Ala Asp Asp Lys His Trp Arg Ser Thr His Ala Arg Ile Ala Asn Gly
```

```
            115                 120                 125
Ala Val Val Pro Gln Gln Leu Ile Gly Gly Thr Pro Met Ile Asp Leu
130                 135                 140
Ser Glu Phe Ser Ala Asn Pro Lys Val Lys Ile Tyr Gly Lys Cys Glu
145                 150                 155                 160
Tyr Met Asn Pro Ser Gly Ser Ile Lys Asp Arg Ile Ala Gln Glu Ile
                165                 170                 175
Leu Thr Arg Ala Leu Glu Thr Gly Glu Leu Lys Pro Gly Met Thr Val
            180                 185                 190
Val Ala Ala Thr Ser Gly Asn Thr Gly Ala Ala Ile Ala Met Ala Cys
        195                 200                 205
Ala Ile Arg Gly Phe Asp Tyr Ile Val Ile Thr Asn Lys Lys Thr Ser
    210                 215                 220
Lys Glu Lys Ile Asp Ala Met Lys Ala Tyr Gly Gly Gln Val Ile Val
225                 230                 235                 240
Ala Glu Ser Gly Val Pro Ala Asp His Pro Asp His Tyr Gln Asn Ile
                245                 250                 255
Glu Thr Thr Met Cys Ala Gln Asn Pro Asn Tyr Tyr Gly Val Asn Gln
            260                 265                 270
Tyr Asp Asn Pro Tyr Asn Ala Asp Ala Tyr Glu Lys Thr Leu Gly Pro
        275                 280                 285
Glu Ile Trp Ser Gln Thr Lys Gly Ala Val Thr His Phe Ile Ala Gly
    290                 295                 300
Gly Ser Thr Gly Gly Thr Ile Thr Gly Thr Gly Arg Tyr Leu Lys Ser
305                 310                 315                 320
Val Asp Pro Thr Ile Lys Ile Met Leu Ala Asp Pro Lys Gly Ser Val
                325                 330                 335
Leu Trp Asp Tyr Phe Val Asn Asp Val Pro Glu Glu Asp Leu Val Ala
            340                 345                 350
Lys Ser Trp Glu Val Glu Gly Val Gly Lys Asp Ser Ile Pro Gly Val
        355                 360                 365
Leu Gln Thr Glu Tyr Ile Asp Gly Ala Val Lys Gly Cys Asp Ala Ser
    370                 375                 380
Ser Phe Arg Ile Cys Arg Met Val Ala Glu Ser Ser Gly Ile Leu Leu
385                 390                 395                 400
Gly Gly Ser Ser Gly Leu Asn Leu His Ala Ala Arg Val Leu Ser Ser
                405                 410                 415
Gln Ile Lys Glu Gly Val Ile Val Thr Val Leu Cys Asp Ser Gly Val
            420                 425                 430
Lys Tyr Leu Ser Lys Ile Phe Asn Asp Glu Trp Leu Glu Ser Lys Asn
        435                 440                 445
Leu Asn Gln Pro Leu Ser Asp Val Lys Asn Phe Gln Val Ala Trp Lys
    450                 455                 460
Lys Asp Gln Ser Glu Ala Ser Asp Asp Glu Asp Ala Asp His Gly Leu
465                 470                 475                 480
Trp Ser Arg Asp Asp Glu Glu Lys Glu Leu Arg Phe Leu Asp Glu Ile
                485                 490                 495
Ala Thr His Met Val Glu Tyr Tyr Arg Asn Ser Ala Arg Ala Ala Asp
            500                 505                 510
Pro Val Ser Thr Tyr Asn Ser Pro Leu Ala Leu His Glu Lys Phe Lys
        515                 520                 525
Glu Val Gly Ile Pro Leu Ala Ile Gly Thr Gly Glu Glu Pro Val Ser
    530                 535                 540
```

Met Ser Leu Leu Thr Thr Ala Met Asn Thr Val Ile Gln Asn Ser Ala
545                 550                 555                 560

Arg Thr Ser His Pro Met Leu Gly Gly Thr Arg Gly Gly Arg Asp Gly
            565                 570                 575

Gly Arg Met Arg Arg Met Gly Glu Leu Ser Trp Glu Leu Gly Ala Ala
        580                 585                 590

Gly Glu Glu Glu Glu Glu Glu Gln Gly Gln Glu Gly Glu Glu Ile
    595                 600                 605

Ser Arg Glu Glu Val Leu Ala Leu Ser Val Glu Leu Ile Glu Ser Ile
610                 615                 620

Ala Ser Gly Lys Glu Pro Leu Asp Ala Ala Arg Leu Gly Ser Leu Leu
625                 630                 635                 640

Trp Thr Leu Ser Asn Ala Leu Leu Glu Asp Leu Thr Asp Arg Asp Asp
            645                 650                 655

Leu Arg Val Pro Gly Asn Ser Leu Glu Thr Phe Pro Val Glu Leu Val
        660                 665                 670

Arg Asn Val Met Gly Ala Val Glu Thr Leu Val Val Ala Leu Thr Phe
    675                 680                 685

Glu Pro Glu Asp Ala Val Thr Gln Arg Ser Gly His Ala Ile Pro Ala
690                 695                 700

Ile Gly Thr His Arg Val Ala Ala Ala Glu Ile Ile Ala Val Leu Leu
705                 710                 715                 720

Gln Ile Gly Cys Gln Asp Ile Asp Glu Arg Ile Ala Lys Leu Lys Leu
            725                 730                 735

Pro Asn Asp Gly Gln Phe Val Leu Val Ser Leu Val Arg Met Phe Phe
        740                 745                 750

Lys Tyr Ser Trp Ser Ser Ala Leu His Ala Thr Val Val Arg Leu Ile
    755                 760                 765

Leu Ala Ala Leu Val Ser Pro His Glu Pro Leu Trp Ala Pro Met Phe
770                 775                 780

Glu Gly Gly Asp Glu Ser Leu Gln Gly Ser Leu Ala Ala Ser Met Lys
785                 790                 795                 800

Thr Ala Leu Ala Thr Lys Pro Ile Ser Thr Arg Asp Gly Asn Val Gly
            805                 810                 815

Ser Val Ile Ile Leu Ala Asn Ala Leu His Glu Leu Glu Thr Cys Asp
        820                 825                 830

Asp Val Glu Arg Gln Ser Val Arg Thr Thr Leu Gln Glu Asp Ala Thr
    835                 840                 845

Trp Arg Ala Ala Ile Asp Gly Glu Asp Ser Pro Leu Ala Asn Leu Asn
850                 855                 860

Asn Glu Gln Ala Gly Gly Leu Cys Gly Pro Lys Pro Gln Lys Ser Pro
865                 870                 875                 880

Val Phe Met Asp Ser Gly Met Gly Ala Asn Val Ile Ser Ser Gln Glu
            885                 890                 895

Leu Leu Arg Met Leu Gln His Ile Ser Leu Gly Gln
        900                 905

<210> SEQ ID NO 17
<211> LENGTH: 542
<212> TYPE: PRT
<213> ORGANISM: Guillardia theta

<400> SEQUENCE: 17

Met Val Pro Pro Ala Leu His Glu Gly Phe Cys Ser Pro Arg Gly Arg

-continued

```
  1               5                   10                  15
Thr Cys Cys Ser Gln Val Gly His Val Glu Leu Leu Glu Ser Trp Glu
                 20                  25                  30

Thr Gln Gly Asn Lys Leu Arg Cys Glu Gln Asp Leu Leu Leu Ala Lys
                 35                  40                  45

Val Pro Ser Arg Phe His Leu Glu Glu Val Ala Glu Leu Asp Asp
                 50                  55                  60

Ile Phe Arg Glu Val Tyr Pro Leu Ile Arg Gln Tyr Glu Thr Glu Asn
 65                  70                  75                  80

Ala Leu Ala Asp Glu His Lys Val Leu Glu Phe Arg Thr Pro Ala Glu
                 85                  90                  95

Leu Lys Glu Glu Val Asp Val Gly Leu Pro Glu Glu Gly Ser Val Glu
                100                 105                 110

Lys Phe Val Glu Gly Cys Arg Ser Ser Met Lys Tyr Ser Val Arg Thr
                115                 120                 125

Ser His Pro Arg Phe Met Asn Gln Leu Tyr Ala Gly Ser Asp Pro Ala
                130                 135                 140

Gly Gln Val Ala Glu Leu Leu Ser Ala Val Leu Asn Thr Thr Ile His
145                 150                 155                 160

Thr Tyr Gly Ala Ala Pro Phe Phe Ser Val Leu Glu Arg Gln Val Ile
                165                 170                 175

Glu Lys Leu Gly Arg Met Leu Gly Phe Gln Glu His Val Asp Gly Val
                180                 185                 190

Phe Ala Pro Gly Gly Ser Tyr Ala Asn Met Val Ala Leu Ile Val Ala
                195                 200                 205

Arg Asn Gln His Phe Pro His Val Arg Glu His Gly Trp Arg Ser Asp
                210                 215                 220

Asp Lys Pro Val Ile Phe Thr Ser Ser His Ala His Tyr Ser Val Ala
225                 230                 235                 240

Lys Ala Ala Met Ile Thr Gly Met Gly Ser Asn Gln Val Val Ala Val
                245                 250                 255

Pro Thr Asp Glu Gln Gly Arg Met Gln Pro Ala Ala Leu Glu Glu Glu
                260                 265                 270

Ile Met Arg Ala Lys Glu Ser Gly Arg Lys Pro Phe Tyr Val Ser Cys
                275                 280                 285

Thr Ala Gly Thr Thr Val Thr Gly Ala Phe Asp Pro Ile Asp Glu Ile
                290                 295                 300

Cys Gln Ile Cys Arg Arg His Glu Met Trp Leu His Thr Asp Gly Ala
305                 310                 315                 320

Trp Gly Gly Ala Ala Ile Phe Ser Glu Glu His Arg Asn Leu Leu Arg
                325                 330                 335

Gly Val Glu Gly Val Asp Ser Phe Cys Leu Asn Pro His Lys Met Leu
                340                 345                 350

Gly Val Pro Met Gln Cys Ser Val Leu Ile Leu Asn Asn His Glu Gly
                355                 360                 365

Arg Ser Arg Gly Ala Thr Glu Glu Ser Leu Asp Leu Gly Gln Lys
                370                 375                 380

Ser Leu Gln Cys Gly Arg Lys Pro Asp Cys Leu Lys Leu Trp Leu Cys
385                 390                 395                 400

Trp Lys Arg His Gly Thr Arg Gly Phe Ala Arg Arg Val Asp Arg Ala
                405                 410                 415

Tyr Thr Phe Ser Gln Lys Phe Ala Glu Met Val Arg Arg Asp Pro Arg
                420                 425                 430
```

```
Phe Tyr Leu Leu Met Asp Pro Ile Ser Cys Asn Val Cys Phe Phe Tyr
            435                 440                 445

Leu Pro Pro Ser Leu Arg Gln Gln Leu Val Asp Arg Asn Leu Asn Asp
    450                 455                 460

Leu Glu Lys Glu Glu Ala Gln Arg Gln Leu Lys Glu Phe His Ala Arg
465                 470                 475                 480

Leu Gly Gln Val Thr Gln Ile Ile Tyr Arg Arg Met Gln Lys Asp Gly
                485                 490                 495

Lys Met Leu Ile Asn Phe Ser Pro Leu Lys Asp Arg Asp Leu Pro His
            500                 505                 510

Phe Phe Arg Ala Val Met Ile Gln Gln Arg Val Thr Glu Asp Asp Leu
            515                 520                 525

Val Phe Ile Leu Asp His Phe Glu His Leu Gly Lys Asp Leu
            530                 535                 540

<210> SEQ ID NO 18
<211> LENGTH: 504
<212> TYPE: PRT
<213> ORGANISM: Candida tenuis

<400> SEQUENCE: 18

Met Ser Leu Gln Thr Pro Leu Glu Thr Asn Arg Ala Thr Glu Leu Asp
1               5                   10                  15

Arg Leu Leu Ala Leu Val Thr Pro Lys Ile Leu Gln His Ile Glu Glu
                20                  25                  30

Ser Asp Pro Ser Ser Leu Asn Phe Lys Gln Asn Ala Leu Gly Gln Tyr
            35                  40                  45

Arg Ser Pro Ala Glu Val Lys Ser His Phe Ala Gln Phe Asn Ser Asp
        50                  55                  60

Phe Glu Pro Ile Lys Asn Asp Glu Gln Lys Leu Gln His Leu Ile Asn
65                  70                  75                  80

Ser Val Leu Asp Val Leu Val Asn Thr Trp Asn Pro Gly Phe Leu Asp
                85                  90                  95

Lys Leu Tyr Ala Ser Asn Asn Pro Ile Gly Val Ile Ser Asp Leu Ile
            100                 105                 110

Leu Ser Val Leu Asn Thr Asn Ser His Val Phe Thr Val Ser Pro Val
        115                 120                 125

Leu Ser Val Leu Glu Asn Tyr Val Ala Arg Glu Tyr Gly Arg Leu Phe
    130                 135                 140

Phe Lys Asp His Gln Asp Thr Cys Gly Gly Leu Thr Phe Ser Gly Gly
145                 150                 155                 160

Ser Trp Ser Asn Ile Thr Ser Leu Gln Met Ala Arg Ala Leu Leu Tyr
                165                 170                 175

Pro Asp Thr Lys Ile Gln Gly Asn Gly Leu His Arg Phe Ala Val Tyr
            180                 185                 190

Thr Ser Lys His Cys His Tyr Ser Val Glu Lys Ala Ala Ile Leu Leu
        195                 200                 205

Gly Leu Gly Ser Gly Ser Val Phe Lys Val Ala Val Asn Asp Asp Gly
    210                 215                 220

Thr Met His His Glu Ser Leu Glu Ala Ala Ile Thr Asp Ser Ile Ala
225                 230                 235                 240

Gln Gly Phe Thr Pro Leu Tyr Ile Asn Ala Thr Ala Gly Thr Thr Val
                245                 250                 255

Phe Gly Ser Phe Asp Ala Phe Ala Pro Ile Ser Arg Ile Ala Gln Lys
```

```
            260                 265                 270
Tyr Arg Val Trp Phe His Ile Asp Gly Ser Trp Gly Gly Asn Val Val
        275                 280                 285

Phe Ser Arg Arg His Arg His Arg Leu Asp Gly Cys His Thr Ala Asp
    290                 295                 300

Ser Ile Thr Val Asn Pro His Lys Met Leu Gly Val Pro Thr Thr Cys
305                 310                 315                 320

Ser Phe Leu Leu Val Pro His Val Gly Lys Phe Gln Gln Ala Met Ser
            325                 330                 335

Leu Asp Ala Pro Tyr Leu Phe His Gly Arg Glu Ser Asp Glu Glu Asn
        340                 345                 350

Phe Asp Leu Ala Asp Gly Thr Met Gly Cys Gly Arg Arg Ala Asp Ser
    355                 360                 365

Phe Lys Leu Tyr Met Ala Trp Lys Tyr Tyr Gly Thr Arg Gly Phe Glu
370                 375                 380

Gln Arg Val Asp His Ala Tyr Asp Thr Val Arg Tyr Phe Leu Gln Ala
385                 390                 395                 400

Thr Arg Gln His Pro Asn Phe Ala Val Val Gly Asp Pro Ala Cys Leu
            405                 410                 415

Gln Val Cys Phe Tyr Tyr Arg Pro Lys Ser Tyr Glu Gly Asp Asp Leu
        420                 425                 430

Thr Pro Val Thr Arg Tyr Ile Ser Arg Glu Leu His Thr Gln Gly Arg
    435                 440                 445

Tyr Leu Val Asp Phe Ser Pro His Pro Gln Ala Gly Ala Gln Asp Glu
450                 455                 460

Gln Gly Glu Phe Phe Arg Val Val Phe Asn Ser Pro Ile Leu Thr Asp
465                 470                 475                 480

Ala Ile Ile Asp Asp Leu Val Thr Ala Ile Val Lys Ala Gly Glu Ala
            485                 490                 495

Phe Glu Arg Asp Gln Arg Lys Ile
        500

<210> SEQ ID NO 19
<211> LENGTH: 610
<212> TYPE: PRT
<213> ORGANISM: Cyanidioschyzon merolae

<400> SEQUENCE: 19

Met Glu Thr Arg Asn Ala Pro Gly Ser Ala Thr Asn Lys Leu Lys Glu
1               5                   10                  15

Val Gly Phe Gly Gly Glu Ile Glu Phe Ala Arg Glu Leu Gln Glu Leu
            20                  25                  30

Leu Gly Ile Val Glu Arg Lys Leu Gly Leu Cys Thr Ser Ser Asp Ala
        35                  40                  45

Gly Ser Glu Asn Gly Val Glu Arg Thr Pro Glu Ala Gln Leu Pro Leu
    50                  55                  60

Val Tyr Val Pro Pro Ser Ala Ile Trp Arg Gln Leu Asp His Tyr Val
65                  70                  75                  80

Gln Cys Val Ile Ser Gly Glu Ser Ala Gly Ser Arg Asp Leu Leu Glu
            85                  90                  95

Gln Phe Leu Glu Asp Leu Leu Arg Tyr Ser Val Arg Thr Lys His Ala
        100                 105                 110

Phe Phe Leu His Arg Leu Tyr Gly Gly Ser Asp Pro Val Gly Gln Ile
    115                 120                 125
```

-continued

```
Ala Asp Leu Ile Cys Ser Val Leu Asn Asn Ser Ala Asp Thr Phe Ser
130                 135                 140

Ala Ala Pro Tyr Leu Val Leu Leu Glu Arg Arg Val Ile Glu Ala Leu
145                 150                 155                 160

Ser Ser Cys Ile Gly Trp Lys Thr Pro Leu Gln Gly Asp Gly Ile Phe
                165                 170                 175

Cys Pro Gly Gly Ser Tyr Ala Asn Leu Ile Ala Leu Thr Thr Ala Arg
                180                 185                 190

His Val Phe Gln Met Asn Ala Arg Arg Pro Gln Thr Lys Arg Thr Gln
            195                 200                 205

Arg His His Cys Asn Glu Arg Arg Met Gly Ile Phe Thr Ser Val Gln
210                 215                 220

Gly His Tyr Ser Val Arg Arg Asn Ala Ala Met Leu Gly Phe Cys Asp
225                 230                 235                 240

Ala Pro Gly Glu Asp Cys Ser Asp Val Val Leu Val Pro Cys Asp Glu
                245                 250                 255

Gln Gly Arg Met Asp Pro Glu Ala Leu Arg Arg Leu Ile His Cys Phe
                260                 265                 270

Arg Asn Thr Arg Pro Leu Ser Ser Val Phe Val Asn Val Thr Ala Gly
            275                 280                 285

Thr Thr Val Leu Ser Ala Phe Asp Pro Leu Pro Glu Ile Trp Thr Val
290                 295                 300

Leu Ala Glu Ala Phe Pro Leu Asn Ser Val Glu Ser Ala Ser Ala Glu
305                 310                 315                 320

Leu Glu Gln Arg Leu Glu Ala Asp Thr Met Ile Arg Glu Arg Leu Pro
                325                 330                 335

Gln Pro Thr Phe Trp Val His Val Asp Gly Ala Leu Gly Gly Ser Phe
                340                 345                 350

Leu Phe Ser Glu Arg Phe Arg Pro Val Ala Leu Ala Gly Leu Glu Lys
            355                 360                 365

Tyr Ala Asn Ser Phe Val Leu Asn Ala His Lys Leu Leu Asn Ala Pro
370                 375                 380

Leu Gln Cys Ser Ile Leu Leu Val Arg Glu Arg Gly Leu Leu Gln Ala
385                 390                 395                 400

Ala His Ala Ala Arg Ala Pro Tyr Leu Phe His Asp Asp Leu Asp Thr
                405                 410                 415

Asp Ala Gln Tyr Asp Ile Gly Asp Met Thr Leu Thr Cys Ser Arg Arg
                420                 425                 430

Ser Asp Ala Leu Lys Phe Trp Leu Met Trp Met Trp Arg Gly Ser Ala
            435                 440                 445

Gly Phe Gly Ala Arg Val Glu Ala Ala Ala Arg Asn Ala Arg Ala Ile
450                 455                 460

Ala Glu Ala Met Ala Lys Arg Pro Cys Phe Leu Leu Val His Trp Pro
465                 470                 475                 480

Leu Asp Arg Ser Tyr Pro Ala Thr Asn Val Cys Phe Tyr Tyr Leu Pro
                485                 490                 495

Ser Asp Met Arg Glu Ser Ile Arg Asn Leu Ala Asp Ile Lys Ala Glu
                500                 505                 510

Thr Ala Ala Gln Leu Leu Gly Ser Ile Ser Val Arg Leu Cys Arg Ala
            515                 520                 525

Leu Gln Val Ser Gly Lys Ala Leu Leu Asn Tyr Cys Thr Leu Glu Gly
530                 535                 540

Thr Asp Leu Pro Ile Phe Leu Arg Leu Ala Leu His Gly Leu His Val
```

```
545                 550                 555                 560
Tyr Glu Glu Gln Glu Ile Gln Asp Leu Leu Asn Arg Ile Glu Asp Cys
                565                 570                 575

Gly Asp His Ala Ile Arg Pro Gly Thr Pro Ala Ser Ile Ser Gly Asn
            580                 585                 590

Val Ser Gly Val Ser Pro Val Gly Asp Asp Gly Ala His Asn Ala
        595                 600                 605

Val Leu
    610

<210> SEQ ID NO 20
<211> LENGTH: 683
<212> TYPE: PRT
<213> ORGANISM: Thalassiosira oceanica

<400> SEQUENCE: 20

Met Gly Arg Arg Lys Ser Asn Met Ser Arg Ser Pro Ser Ser Leu Leu
1               5                   10                  15

Cys Pro Pro Trp Ala Asp Gly Val Val Thr Pro Leu His Trp Gly Ala
            20                  25                  30

Leu Ile Ala Ile Ala Ala Thr Ile Phe Ser Leu Gly Thr Leu Val Gly
        35                  40                  45

Tyr Asn Leu Gly Arg Arg Arg Gly Arg Pro Thr Lys Thr Lys Gly
    50                  55                  60

Ser Ala Lys His Asp Gly Val Arg Ala Thr Gly Arg Leu Pro Lys Arg
65              70                  75                  80

Lys Asn Ile His Ser Leu Asp Gly Ser Thr Met Val Leu Asn Gly Ser
                85                  90                  95

Leu Glu Leu Met Ala Ser Lys Trp Gly Gly Asp Glu Phe Gln Asn Pro
            100                 105                 110

Arg Glu Val Ala Val Val Glu Tyr Leu Ser Pro Glu Glu Met Ser Arg
        115                 120                 125

Met Leu Phe Lys Ser Val Thr Glu His Ser Ser Asp Ser Thr Leu Ser
    130                 135                 140

Leu Asp Glu Ser Asp Arg Asp Leu Ser Pro Lys Ser Ser Ala Thr Asp
145                 150                 155                 160

Leu Thr Ser Leu Val Pro Thr Phe Asp Lys Ser Arg Ser Ile Pro Thr
                165                 170                 175

Glu Pro Glu Lys Phe Ile Glu Leu Leu Gly Leu Ile Gln Lys Tyr Ser
            180                 185                 190

Val Asn Thr Ser His Pro Tyr Phe Asn Gln Leu Phe Gly Ser Leu
        195                 200                 205

Asp Pro Ile Ala Leu Ala Ala Glu Ile Val Ala Leu Ser Val Asn Thr
    210                 215                 220

Ser Val Tyr Thr Tyr Glu Thr Ala Pro Val Phe Ser Leu Ile Glu Arg
225                 230                 235                 240

Glu Val Met Gly Gln Ile Gly Lys Leu Val Phe Gly Pro Thr Ser Gly
                245                 250                 255

Lys Gln Ile Ser Phe Glu Ser Asp Asp Lys Phe Glu Gly Gly Leu
            260                 265                 270

Met Ile Pro Gly Gly Ser Leu Ala Asn Leu Thr Ala Met His Ala Ala
        275                 280                 285

Arg His Arg Trp Lys Val Met Asn Gly Phe Ile Lys Gln Ala Thr Glu
    290                 295                 300
```

```
Asp Thr Glu Gln Met Leu Gly Thr Asp Trp Ser Thr Phe Gly Glu
305                 310                 315                 320

Lys Lys Ser Asp Asp Val Phe Pro Thr Thr Ala Lys Met Gln Gly Glu
                325                 330                 335

Asp Thr Glu Thr Gly Glu Thr Leu Cys Asp Tyr Ile Arg Ser Val Pro
            340                 345                 350

Asp Leu Val Ala Phe Val Ser Ser Glu Ala His Tyr Ser Phe Ser Lys
            355                 360                 365

Ser Ala Arg Val Leu Gly Leu Arg Glu Asp Asp Leu Val Ile Ile Pro
        370                 375                 380

Thr His Pro Asp Gly Arg Met Asn Val His Glu Leu Ser Lys Arg Ile
385                 390                 395                 400

Glu Glu Ile Glu Leu Glu Ser Ala Ser His Met Asp Ala Arg Ile Arg
                405                 410                 415

Val Pro Phe Phe Val Ala Cys Thr Ala Gly Ser Thr Val Arg Gly Ser
            420                 425                 430

Phe Asp Glu Ile Glu Ile Val Lys Val Cys Arg Arg Tyr Glu Ala
        435                 440                 445

Arg Ala Lys Ser Ser Glu Ala Arg Ser Ile Trp Val His Val Asp Gly
450                 455                 460

Ala Trp Gly Gly Ser Ala Met Phe Ser Ser Arg Arg His Ile Arg Asp
465                 470                 475                 480

Ile Thr His Met Asp Glu Ile Arg His Ala Asp Ser Phe Thr Phe Asn
                485                 490                 495

Pro His Lys Met Leu Gly Ala Pro Gln Gln Thr Thr Ala Phe Ile Val
                500                 505                 510

Arg His Arg His Ala Leu Lys Arg Ala Asn Ser Ala Gly Ala Lys Tyr
                515                 520                 525

Leu Phe Asp Pro Arg Lys Asn Gly Ala Glu Tyr Asp Leu Gly Asp Leu
            530                 535                 540

Ser Tyr Thr Cys Gly Arg Arg Thr Asp Ala Val Lys Leu Trp Ala Met
545                 550                 555                 560

Trp Lys Tyr Tyr Gly Lys Ser Gly Leu Gly Glu Arg Val Asp Gln Lys
                565                 570                 575

Val Asp Glu Leu Gln Leu Phe Val Asp Glu Leu Arg Gly Arg Pro Ser
            580                 585                 590

Phe Ala Leu Ala Cys Ala Pro Trp Pro Phe Asn Val Asn Phe Ser Thr
            595                 600                 605

Ser Leu Gln Gly Tyr Glu Arg Phe Trp Arg Leu Ala Asp Met Ser Asn
        610                 615                 620

Val Ser Val Gln Leu Lys Leu Arg Leu His Glu Ala Gly Glu Met Ile
625                 630                 635                 640

Ile Pro Tyr Gln Pro Leu Thr Asn Gln Lys Ala Asp Cys Phe Arg Leu
                645                 650                 655

Val Leu Ala Gly Lys Lys Asp Phe Gly Leu Gly Asp Met Arg His Ile
            660                 665                 670

Leu Asp Thr Met Glu Arg Tyr Gly Arg Asp Leu
        675                 680
```

<210> SEQ ID NO 21
<211> LENGTH: 177
<212> TYPE: DNA
<213> ORGANISM: Arabidopsis thaliana

<400> SEQUENCE: 21

```
atggctgctt atggtcaaat ctcctcggga atgactgtag atcctcaggt tctctcttcc      60
tccagaaaca ttggagtttc cctatcacct ctccggagaa cactaatcgg cgccggagtt     120
aggtctacta gtatctctct ccgtcaatgt tctctctccg ttagatcgat taaaatc        177
```

<210> SEQ ID NO 22
<211> LENGTH: 59
<212> TYPE: PRT
<213> ORGANISM: Arabidopsis thaliana

<400> SEQUENCE: 22

```
Met Ala Ala Tyr Gly Gln Ile Ser Ser Gly Met Thr Val Asp Pro Gln
1               5                   10                  15

Val Leu Ser Ser Ser Arg Asn Ile Gly Val Ser Leu Ser Pro Leu Arg
            20                  25                  30

Arg Thr Leu Ile Gly Ala Gly Val Arg Ser Thr Ser Ile Ser Leu Arg
        35                  40                  45

Gln Cys Ser Leu Ser Val Arg Ser Ile Lys Ile
    50                  55
```

<210> SEQ ID NO 23
<211> LENGTH: 39
<212> TYPE: DNA
<213> ORGANISM: Artificial Sequence
<220> FEATURE:
<223> OTHER INFORMATION: Synthetic Construct

<400> SEQUENCE: 23

```
agtactgaag gcgaagttaa cgcggaagaa gaaggcttt                             39
```